(12) United States Patent
Kelley et al.

(10) Patent No.: US 6,630,464 B1
(45) Date of Patent: Oct. 7, 2003

(54) CYCLIN DEPENDENT KINASE (CDK)4 INHIBITORS AND THEIR USE FOR TREATING CANCER

(75) Inventors: Michael J. Kelley, Chapel Hill, NC (US); Kazuhiko Nakagawa, Osaka (JP); Barry Roy Dent, Wellington (NZ)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/403,659

(22) PCT Filed: Apr. 28, 1998

(86) PCT No.: PCT/US98/08602

§ 371 (c)(1),
(2), (4) Date: Feb. 18, 2000

(87) PCT Pub. No.: WO98/49146

PCT Pub. Date: Nov. 5, 1998

*Related U.S. Application Data*

(60) Provisional application No. 60/044,256, filed on Apr. 28, 1997.

(51) Int. Cl.$^7$ ............................................. A61K 31/54
(52) U.S. Cl. .................................. 514/222.5; 514/222.8
(58) Field of Search ....................................... 514/222.5

(56) References Cited

PUBLICATIONS

Sadans et al., Indian J. Chem., Sect. B (1990), 29B(6), 598–9 Abstract Only.*

Reddy et al., Indian J. of Chemistry, vol. 24B, Dec., 1985, pp. 1295–1297.*

* cited by examiner

*Primary Examiner*—Jerome D. Goldberg
(74) *Attorney, Agent, or Firm*—Klarquist Sparkman, LLP

(57) ABSTRACT

Certain derivatives of acridones and benzothiadiazines have been found to have anti-cancer properties by virtue of their specific inhibition of the cyclin D dependant kinase CDK4. These molecules inhibit CDK4 activity more than they inhibit the activity of other such kinases (e.g. CDC2 and CDK2). This specificity results in an improved therapeutic index when used as drugs to treat susceptible cancers.

12 Claims, 47 Drawing Sheets

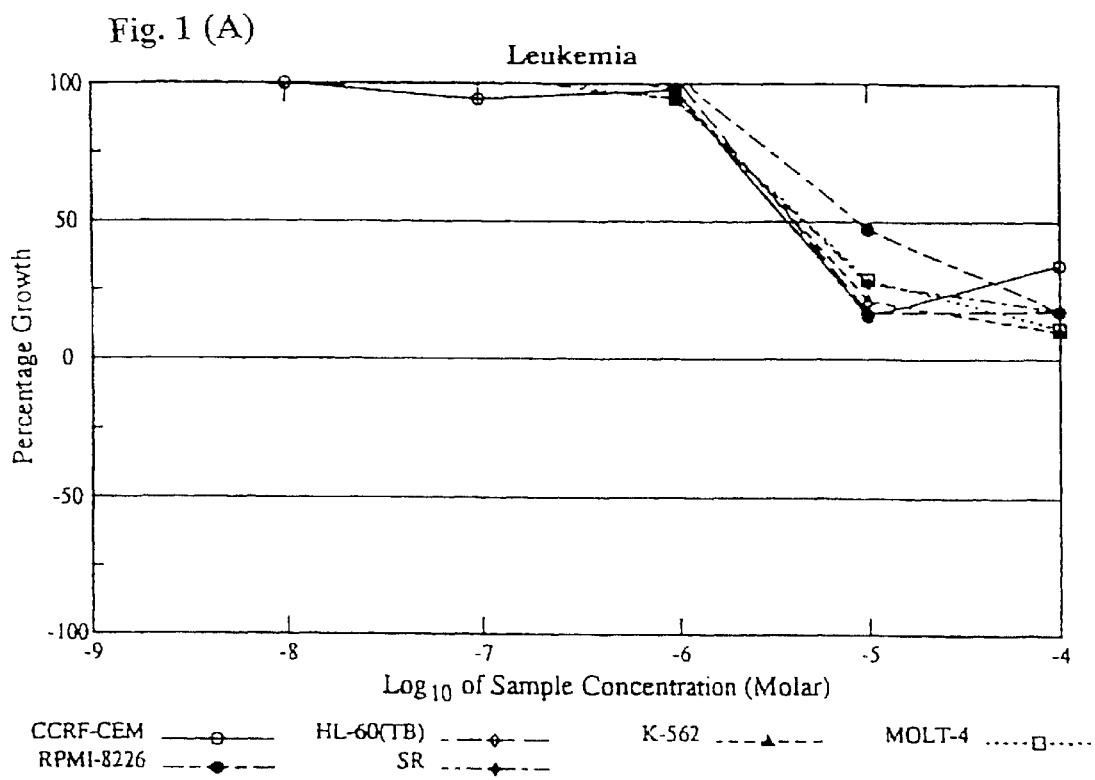
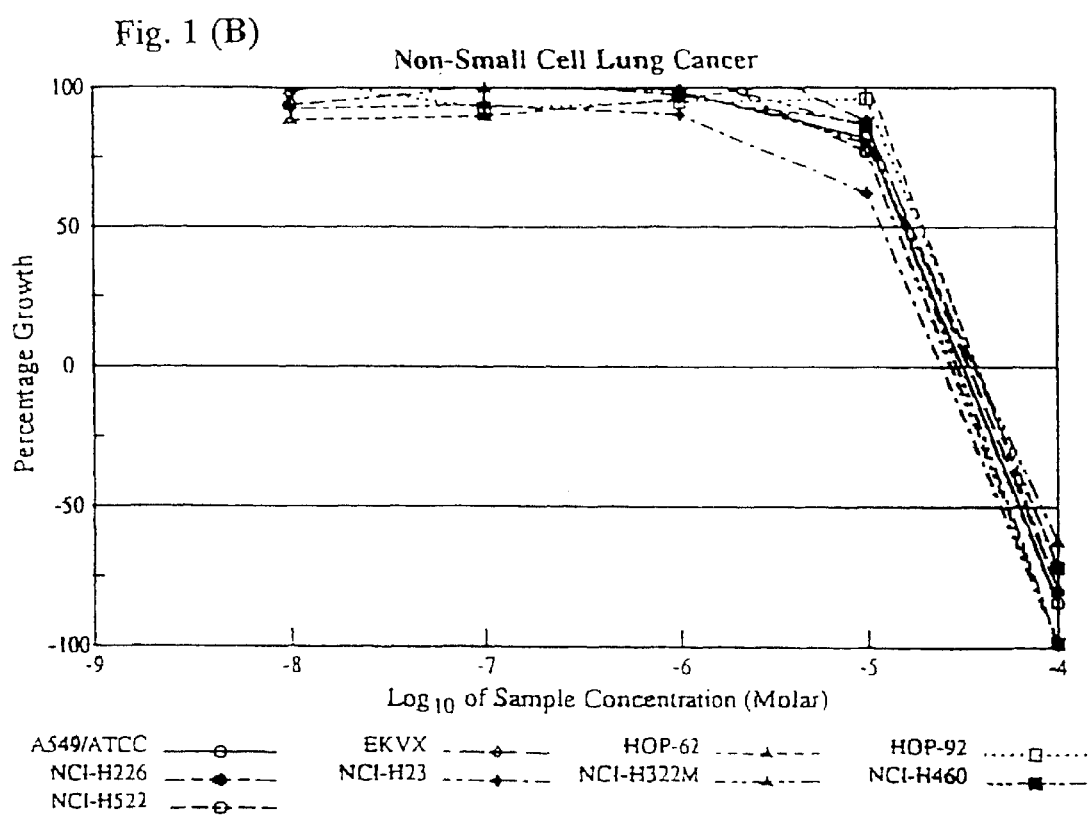

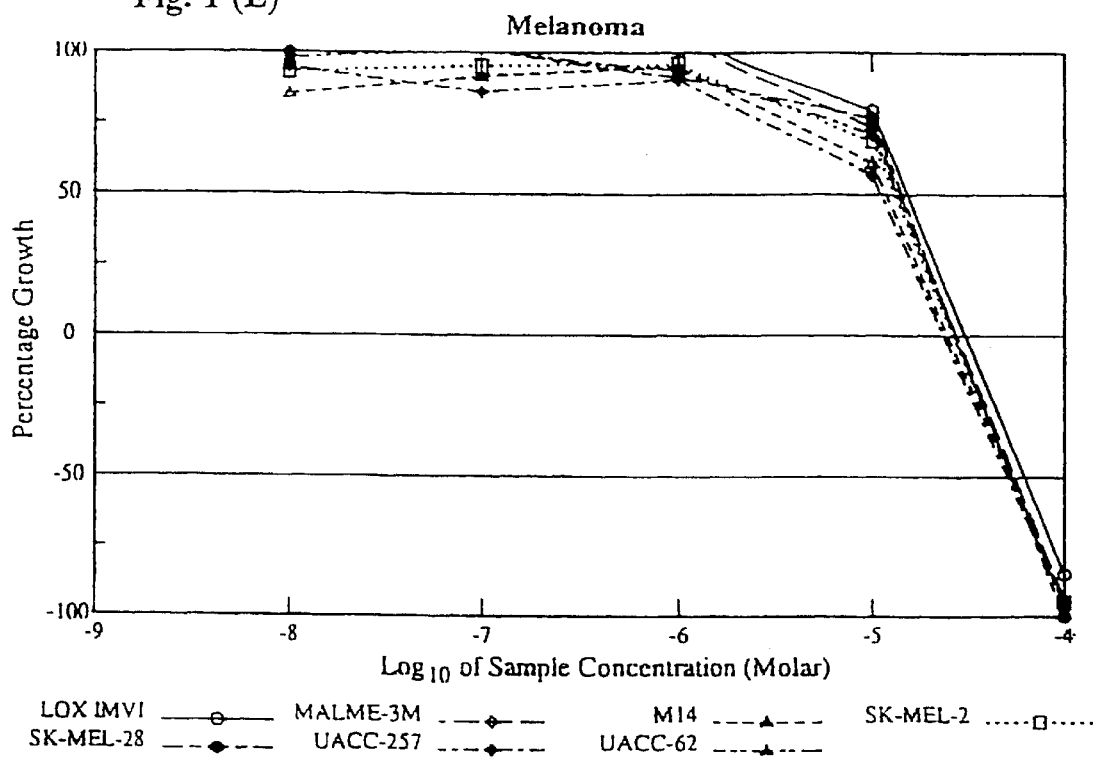
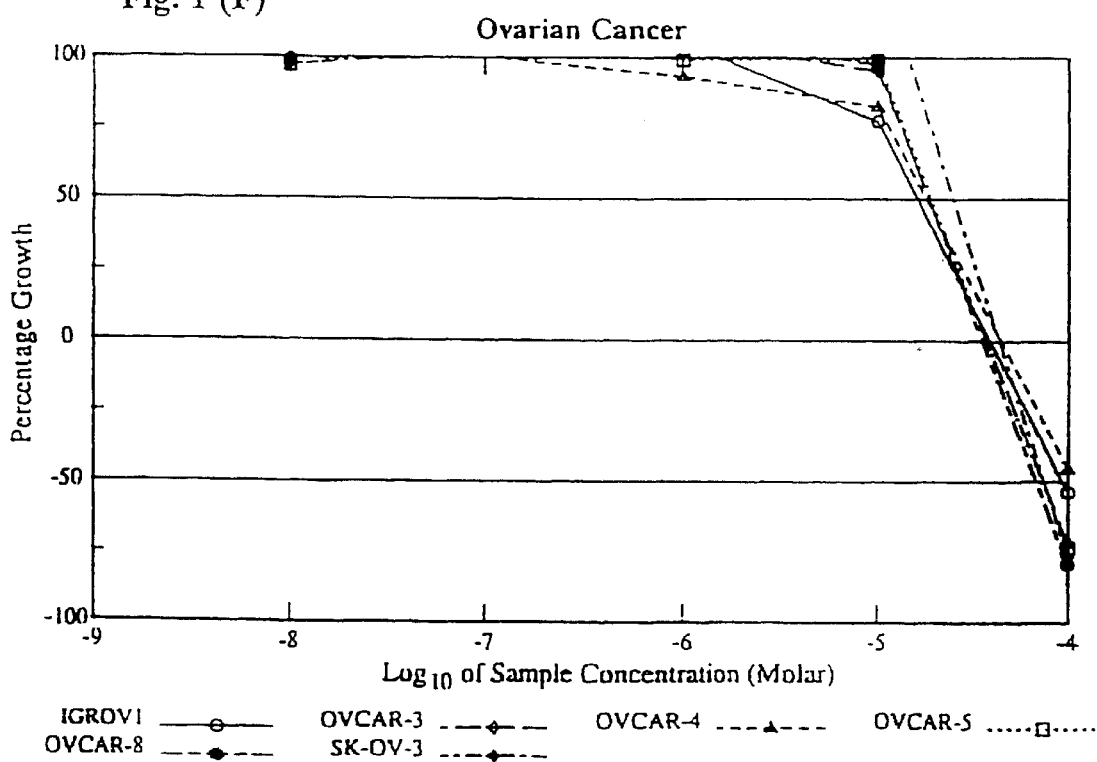

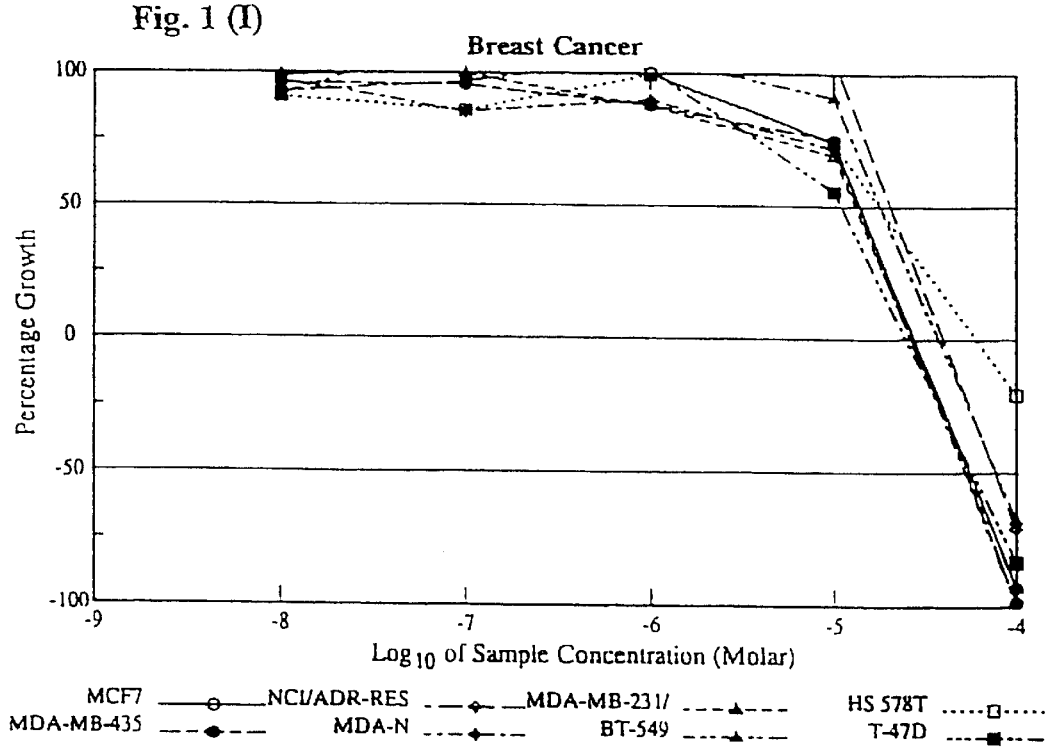

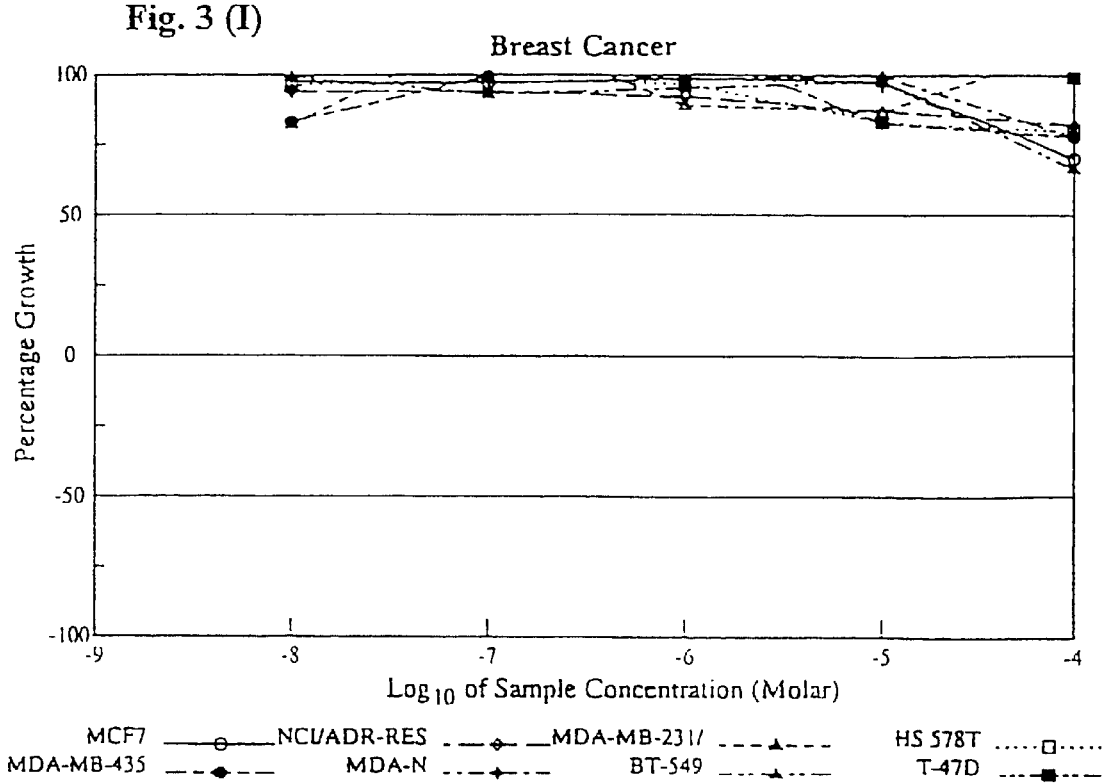

Fig. 4(C)

| Panel/Cell Line | Log₁₀ LC50 | LC50 |
|---|---|---|
| Leukemia | | |
| CCRF-CEM | > -4.00 | |
| HL-60(TB) | > -4.00 | |
| K-562 | > -4.00 | |
| MOLT-4 | > -4.00 | |
| SR | > -4.00 | |
| Non-Small Cell Lung Cancer | | |
| A549/ATCC | > -4.00 | |
| EKVX | > -4.00 | |
| HOP-62 | > -4.00 | |
| HOP-92 | > -4.00 | |
| NCI-H226 | > -4.00 | |
| NCI-H23 | > -4.00 | |
| NCI-H322M | > -4.00 | |
| NCI-H460 | > -4.00 | |
| NCI-H522 | > -4.00 | |
| Colon Cancer | | |
| COLO 205 | > -4.00 | |
| HCC-2998 | > -4.00 | |
| HCT-116 | > -4.00 | |
| HCT-15 | > -4.00 | |
| HT29 | > -4.00 | |
| KM12 | > -4.00 | |
| SW-620 | > -4.00 | |
| CNS Cancer | | |
| SF-268 | > -4.00 | |
| SF-295 | > -4.00 | |
| SF-539 | > -4.00 | |
| SNB-19 | > -4.00 | |
| U251 | > -4.00 | |
| Melanoma | | |
| LOX IMVI | > -4.00 | |
| M14 | > -4.00 | |
| SK-MEL-2 | > -4.00 | |
| SK-MEL-28 | > -4.00 | |
| SK-MEL-5 | > -4.00 | |
| UACC-257 | > -4.00 | |
| UACC-62 | > -4.00 | |
| Ovarian Cancer | | |
| IGROV1 | > -4.00 | |
| OVCAR-3 | > -4.00 | |
| OVCAR-4 | > -4.00 | |
| OVCAR-5 | > -4.00 | |
| OVCAR-8 | > -4.00 | |
| SK-OV-3 | > -4.00 | |
| Renal Cancer | | |
| 786-0 | > -4.00 | |
| A498 | > -4.00 | |
| ACHN | > -4.00 | |
| CAKI-1 | -4.10 | |
| RXF 393 | > -4.00 | |
| SN12C | > -4.00 | |
| TK-10 | > -4.00 | |
| UO-31 | > -4.00 | |
| Prostate Cancer | | |
| PC-3 | > -4.00 | |
| DU-145 | > -4.00 | |
| Breast Cancer | | |
| MCF7 | > -4.00 | |
| NCI/ADR-RES | > -4.00 | |
| MDA-MB-231/ATCC | > -4.00 | |
| HS 578T | > -4.00 | |
| MDA-MB-435 | > -4.00 | |
| MDA-N | > -4.00 | |
| BT-549 | > -4.00 | |
| T-47D | > -4.00 | |
| MG_MID | -4.00 | |
| Delta | 0.10 | |
| Range | 0.10 | |

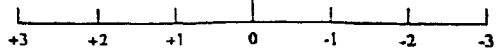

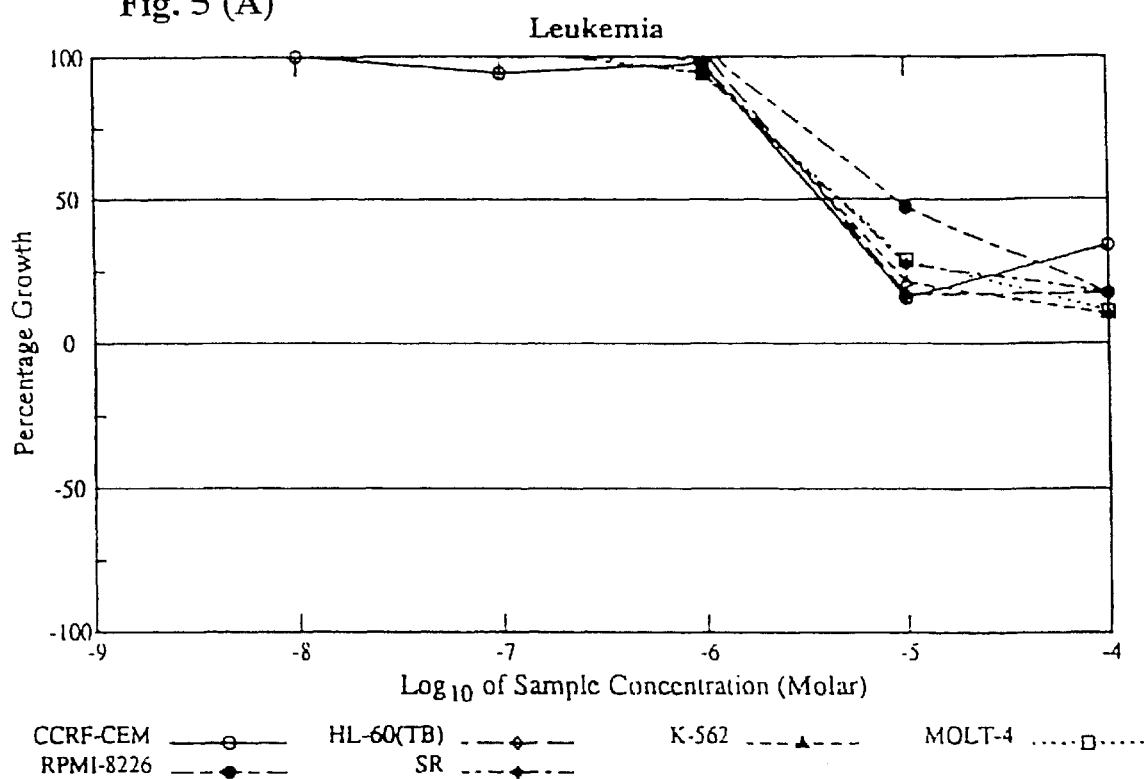
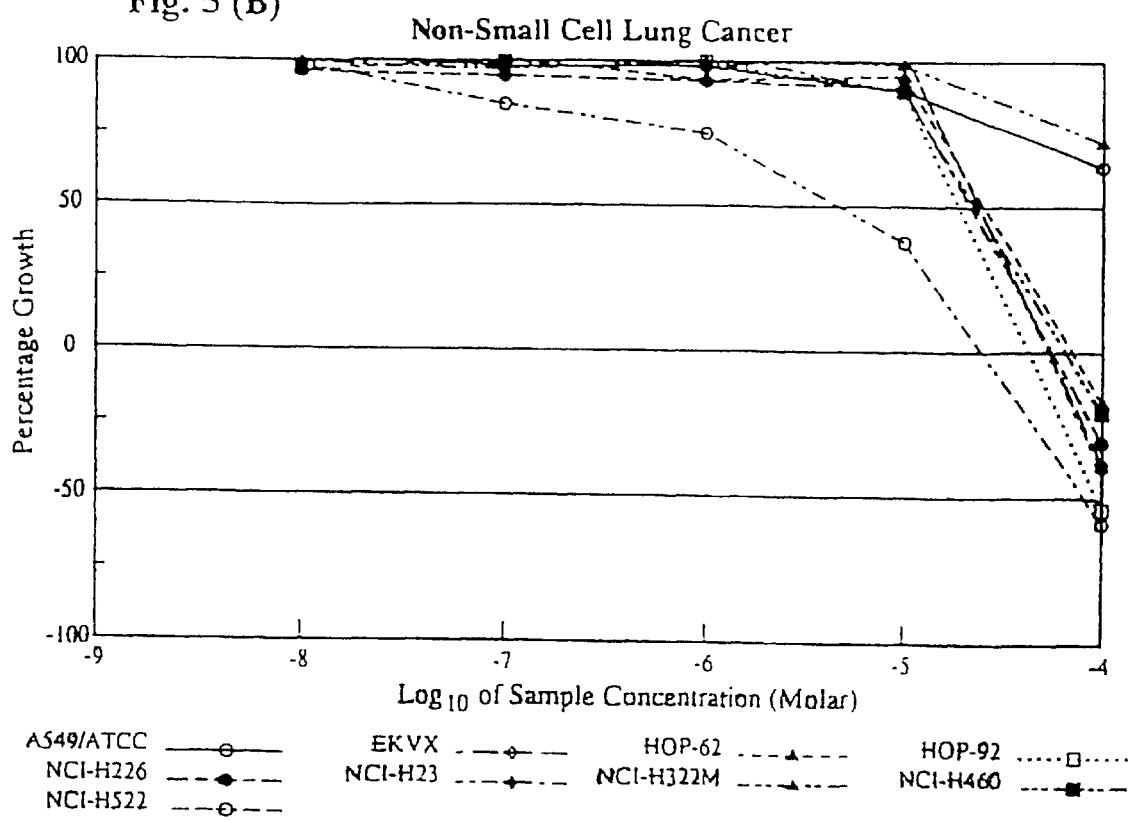

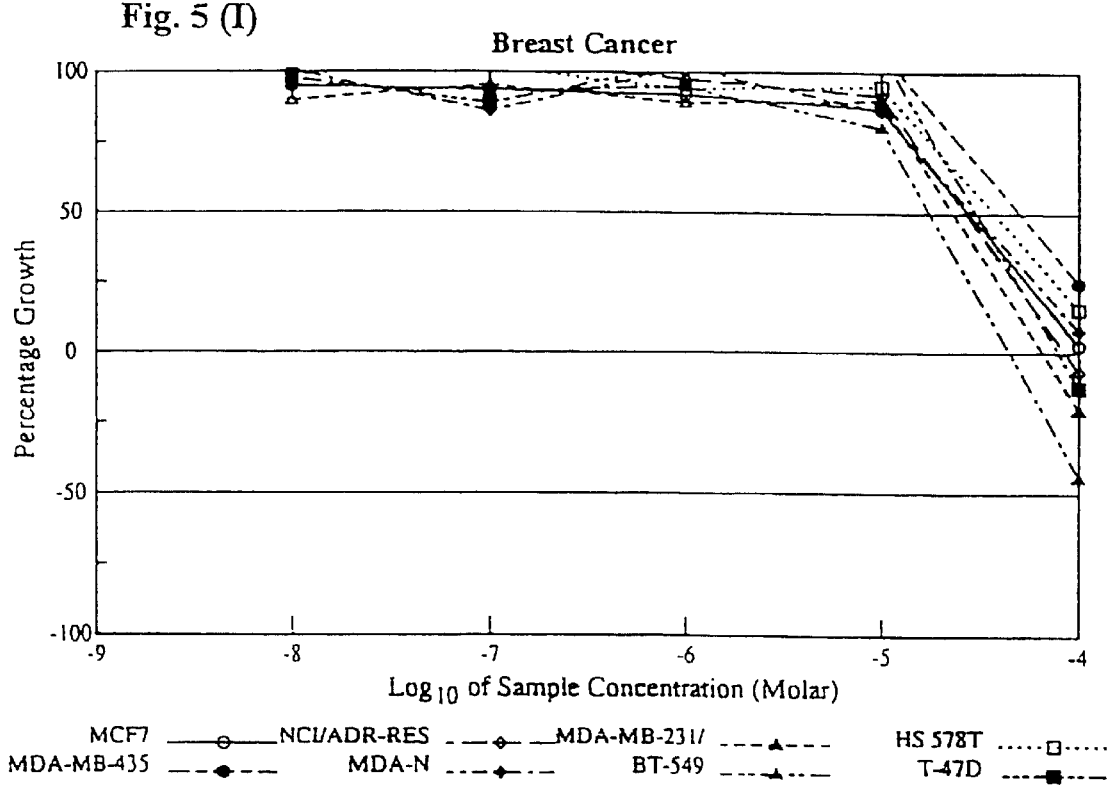

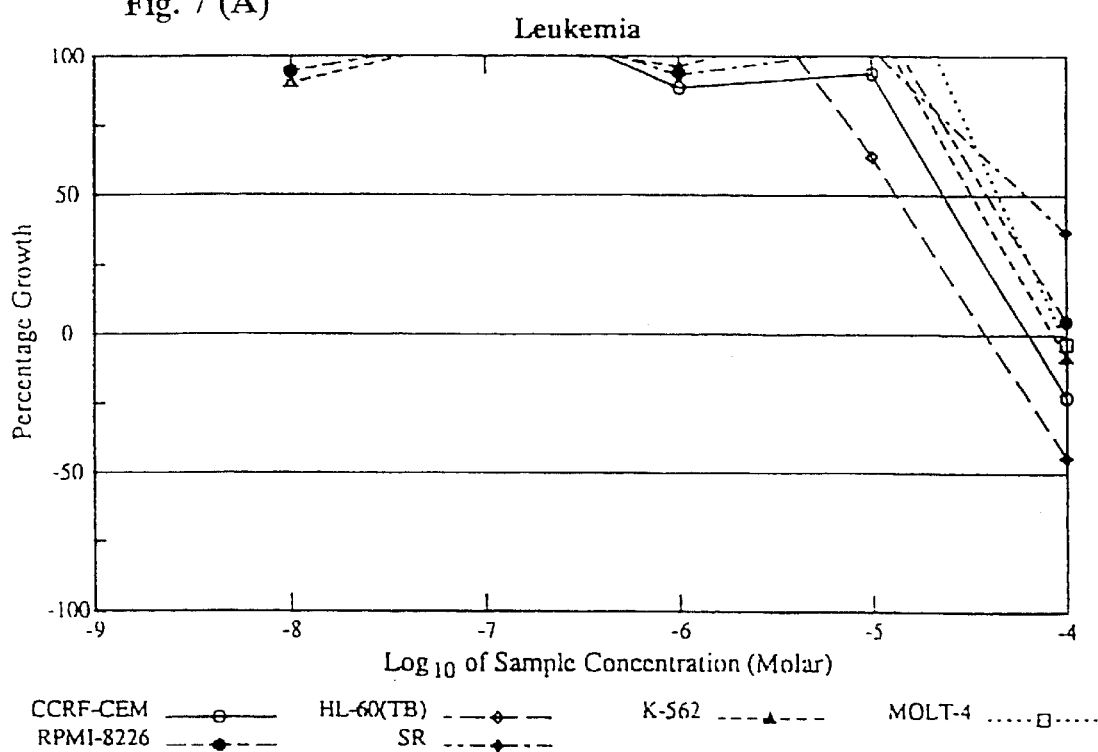
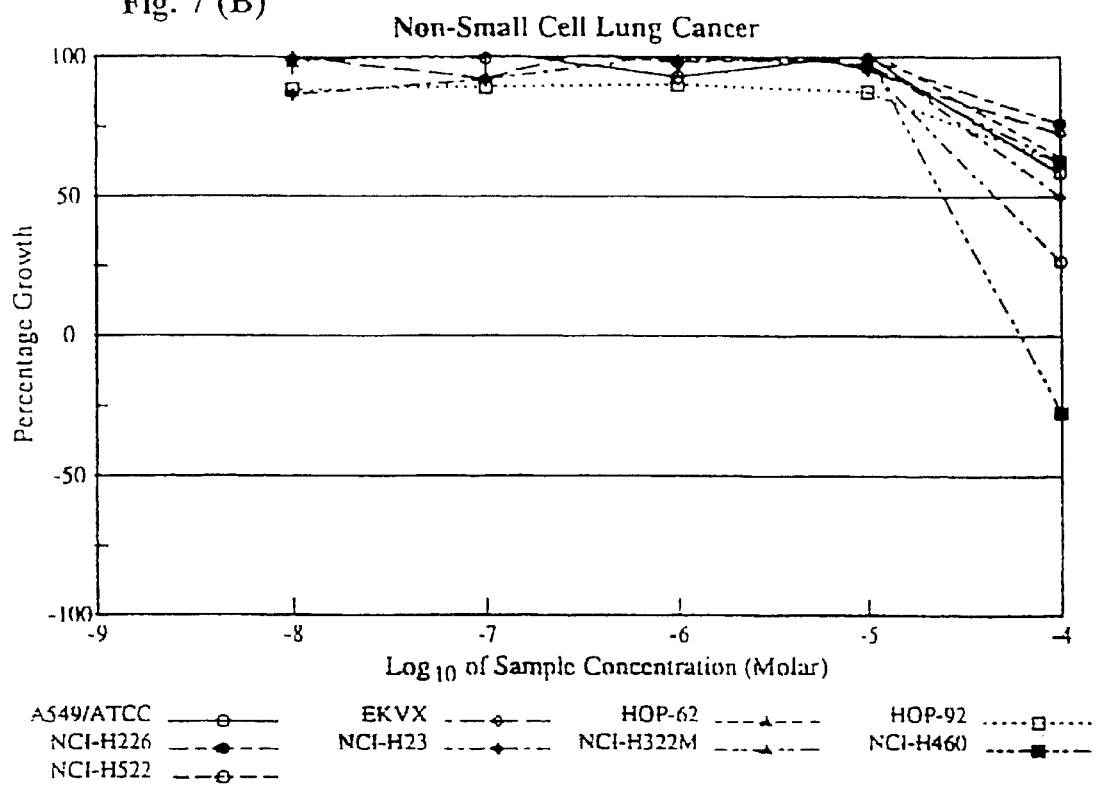

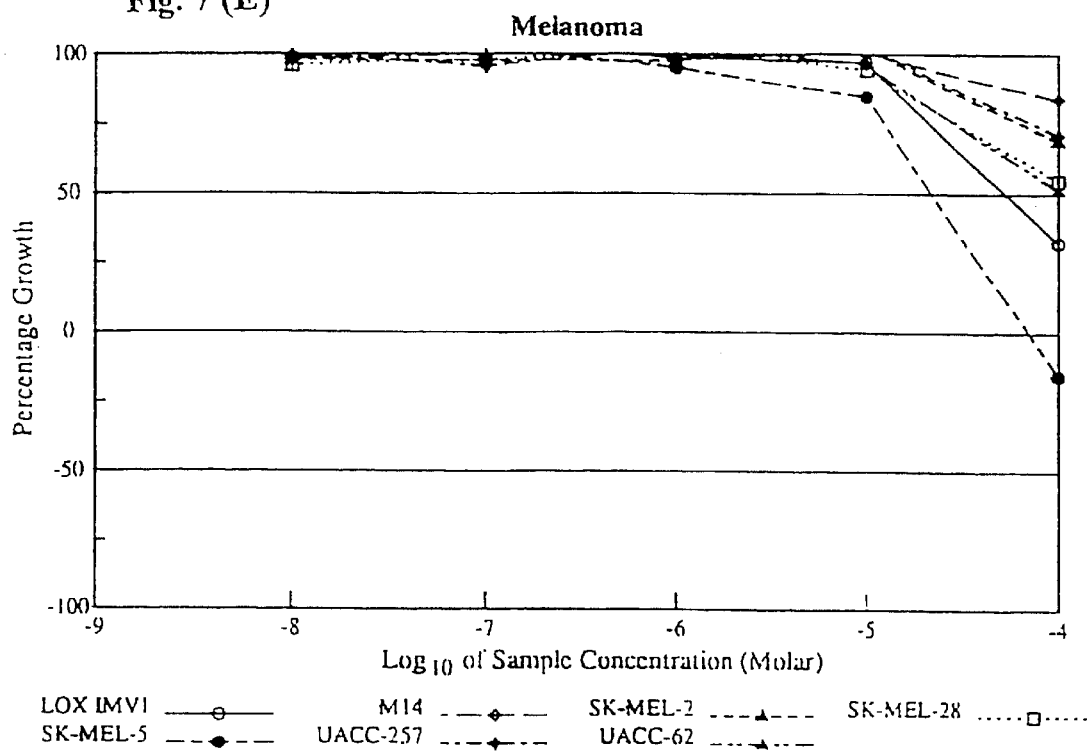
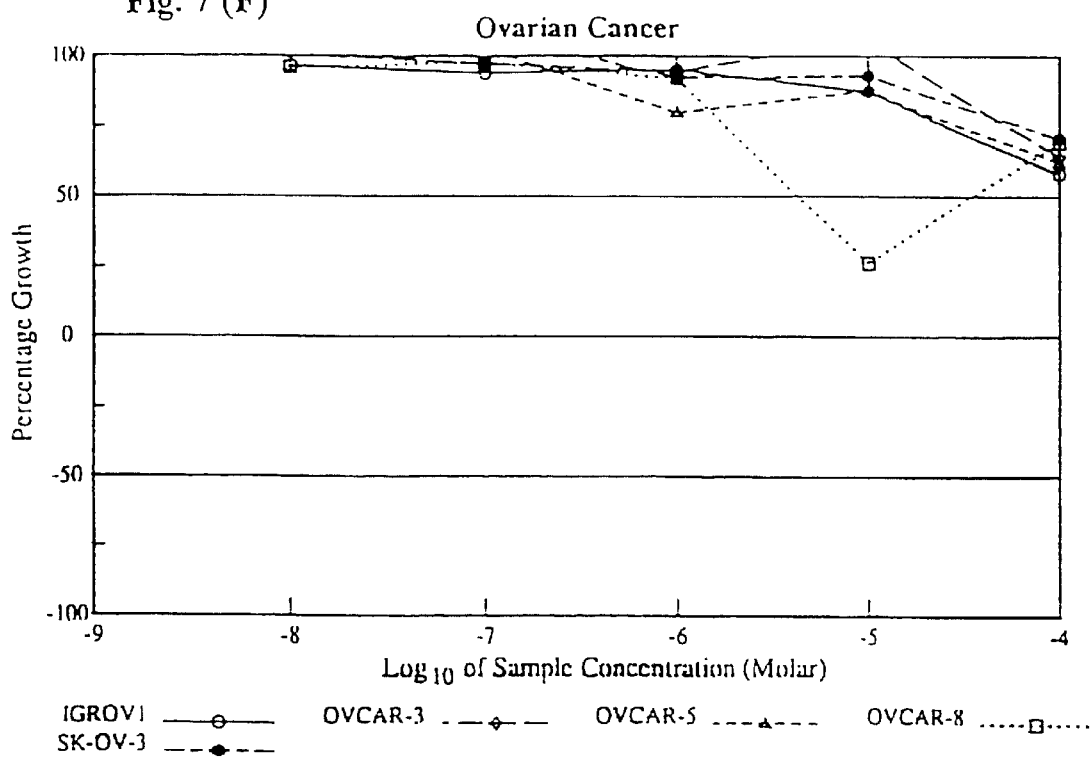

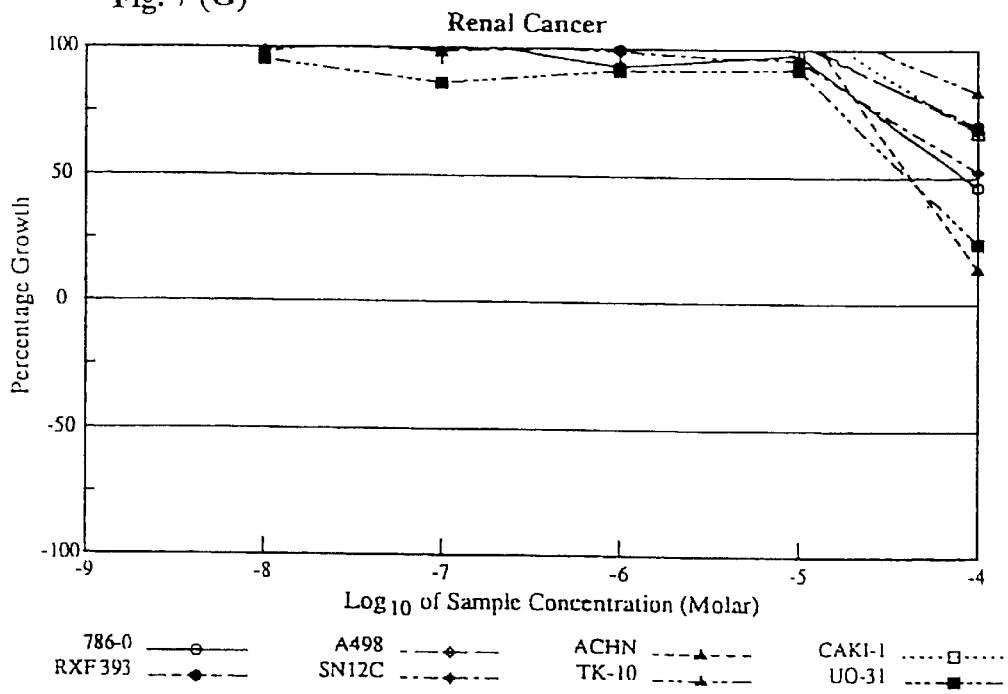
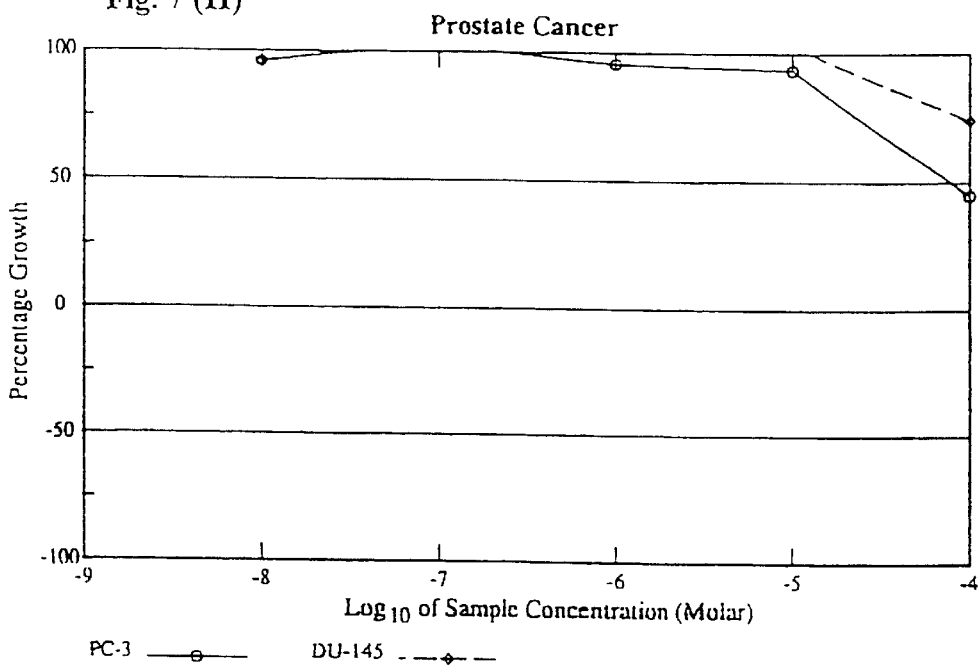

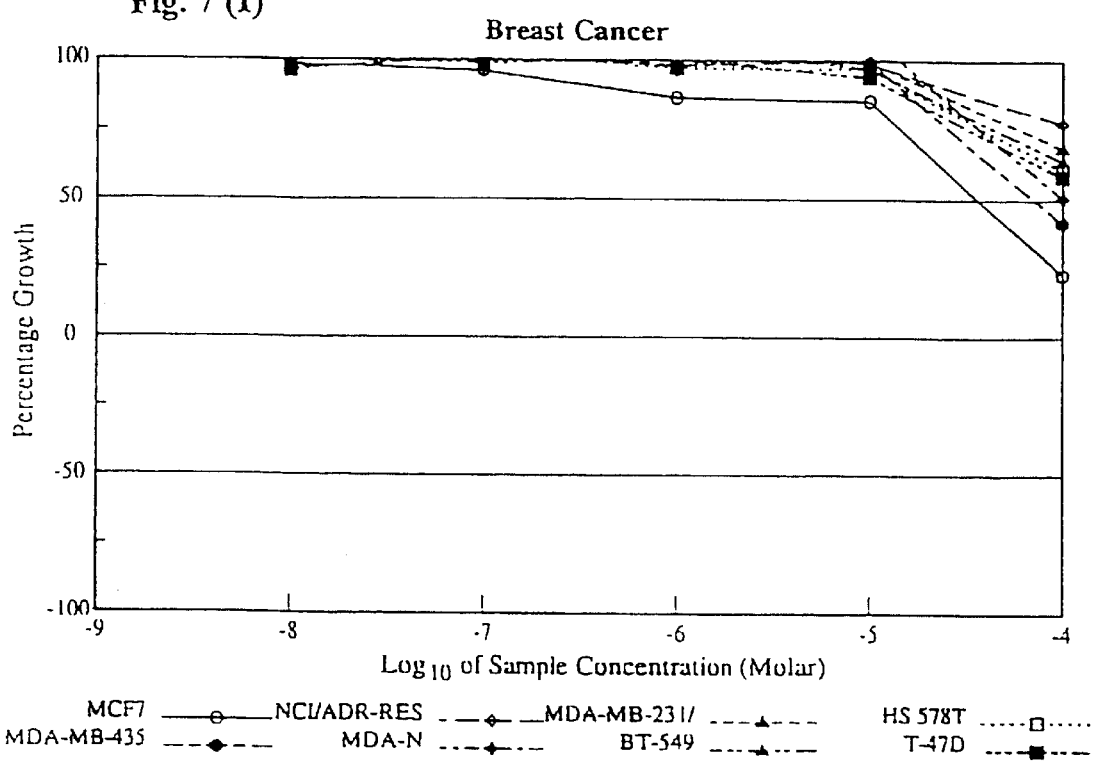

Fig. 8(C)

| Panel/Cell Line | Log₁₀ LC50 | LC50 |
|---|---|---|
| Leukemia | | |
|   CCRF-CEM | > -4.00 | |
|   HL-60(TB) | > -4.00 | |
|   K-562 | > -4.00 | |
|   MOLT-4 | > -4.00 | |
|   RPMI-8226 | > -4.00 | |
|   SR | > -4.00 | |
| Non-Small Cell Lung Cancer | | |
|   A549/ATCC | > -4.00 | |
|   EKVX | > -4.00 | |
|   HOP-62 | > -4.00 | |
|   HOP-92 | > -4.00 | |
|   NCI-H226 | > -4.00 | |
|   NCI-H23 | > -4.00 | |
|   NCI-H322M | > -4.00 | |
|   NCI-H460 | > -4.00 | |
|   NCI-H522 | > -4.00 | |
| Colon Cancer | | |
|   COLO 205 | > -4.00 | |
|   HCC-2998 | > -4.00 | |
|   HCT-116 | > -4.00 | |
|   HCT-15 | > -4.00 | |
|   HT29 | > -4.00 | |
|   KM12 | > -4.00 | |
|   SW-620 | > -4.00 | |
| CNS Cancer | | |
|   SF-268 | > -4.00 | |
|   SF-295 | > -4.00 | |
|   SF-539 | > -4.00 | |
|   SNB-19 | > -4.00 | |
|   SNB-75 | > -4.00 | |
|   U251 | > -4.00 | |
| Melanoma | | |
|   LOX IMVI | > -4.00 | |
|   M14 | > -4.00 | |
|   SK-MEL-2 | > -4.00 | |
|   SK-MEL-28 | > -4.00 | |
|   SK-MEL-5 | > -4.00 | |
|   UACC-257 | > -4.00 | |
|   UACC-62 | > -4.00 | |
| Ovarian Cancer | | |
|   IGROV1 | > -4.00 | |
|   OVCAR-3 | > -4.00 | |
|   OVCAR-5 | > -4.00 | |
|   OVCAR-8 | > -4.00 | |
|   SK-OV-3 | > -4.00 | |
| Renal Cancer | | |
|   786-0 | > -4.00 | |
|   A498 | > -4.00 | |
|   ACHN | > -4.00 | |
|   CAKI-1 | > -4.00 | |
|   RXF 393 | > -4.00 | |
|   SN12C | > -4.00 | |
|   TK-10 | > -4.00 | |
|   UO-31 | > -4.00 | |
| Prostate Cancer | | |
|   PC-3 | > -4.00 | |
|   DU-145 | > -4.00 | |
| Breast Cancer | | |
|   MCF7 | > -4.00 | |
|   NCI/ADR-RES | > -4.00 | |
|   MDA-MB-231/ATCC | > -4.00 | |
|   HS 578T | > -4.00 | |
|   MDA-MB-435 | > -4.00 | |
|   MDA-N | > -4.00 | |
|   BT-549 | > -4.00 | |
|   T-47D | > -4.00 | |
| MG_MID | -4.00 | |
| Delta | 0.00 | |
| Range | 0.00 | 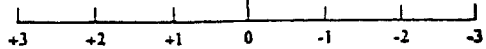 |

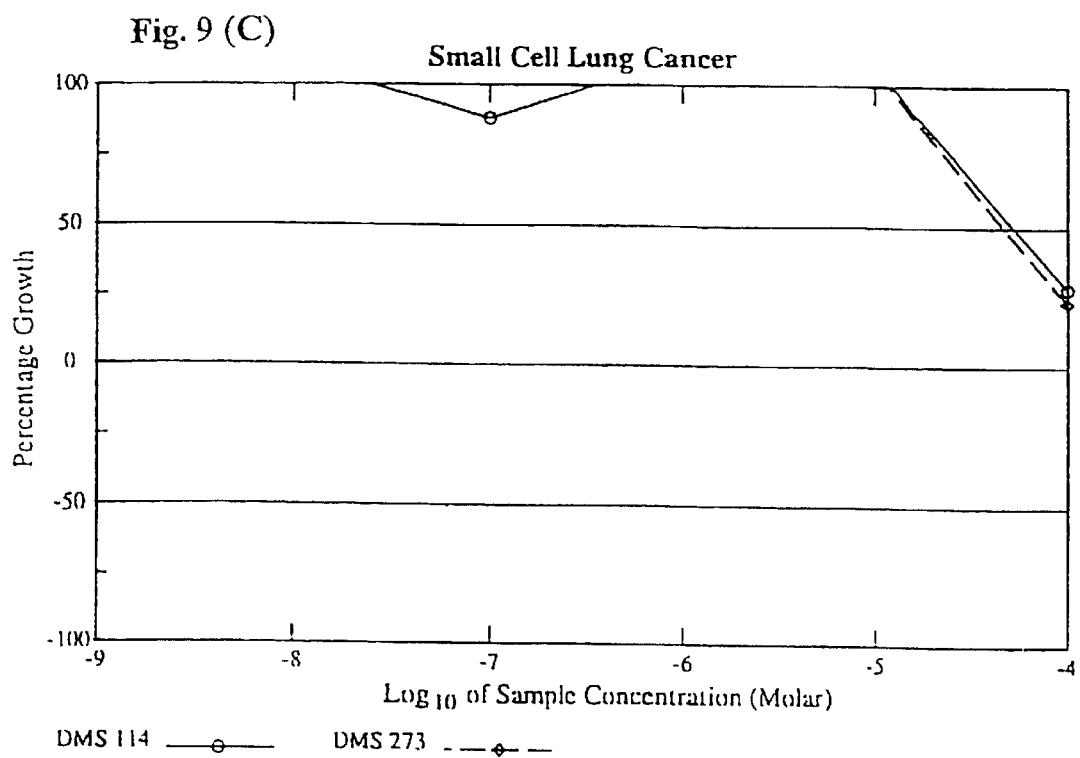
Fig. 9 (C) Small Cell Lung Cancer
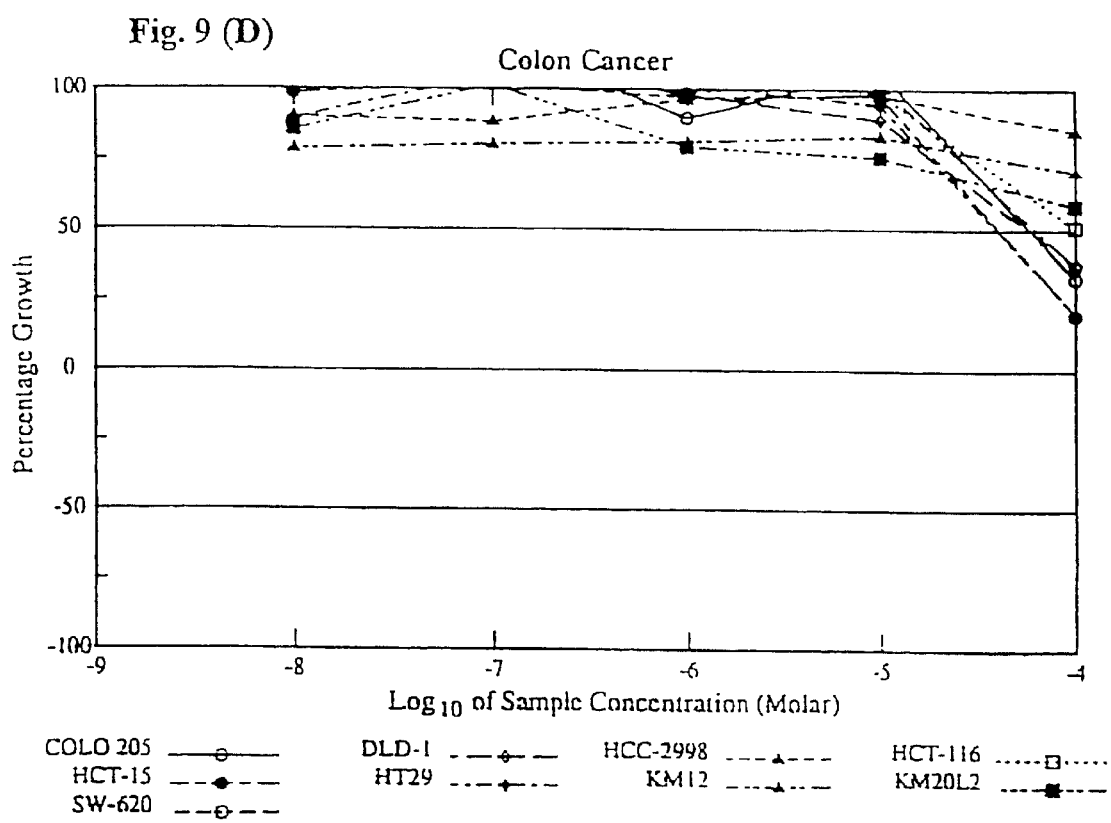
Fig. 9 (D) Colon Cancer

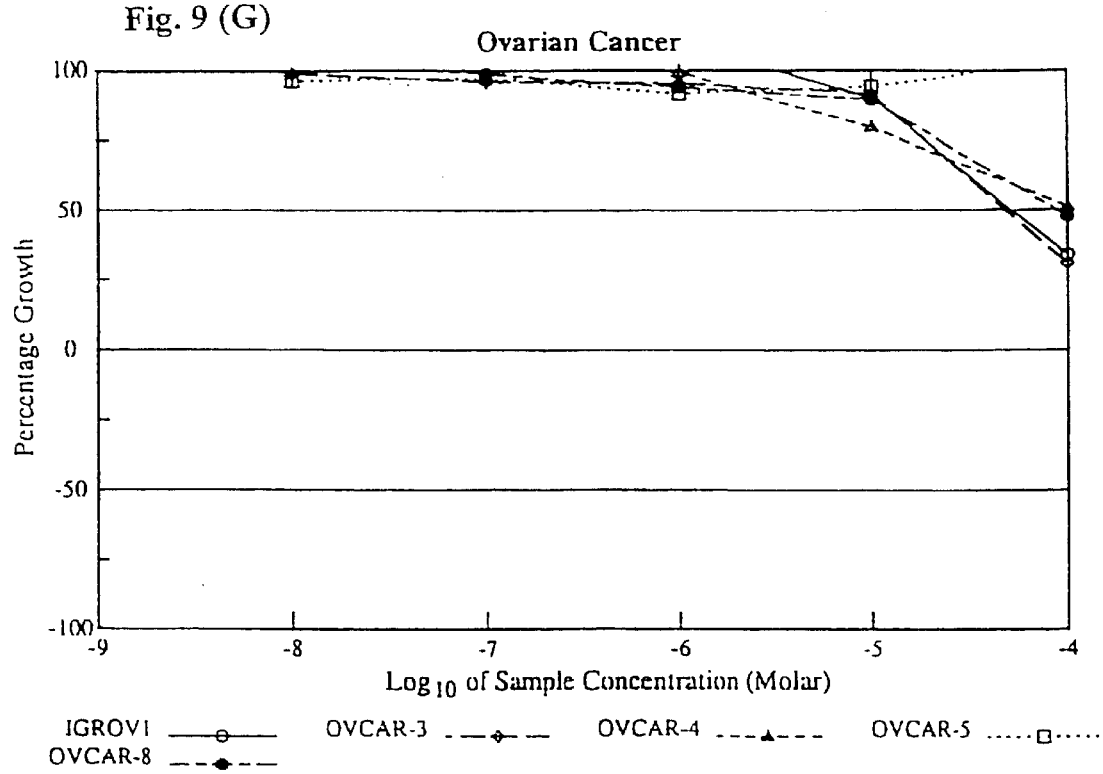
Fig. 9 (G) Ovarian Cancer
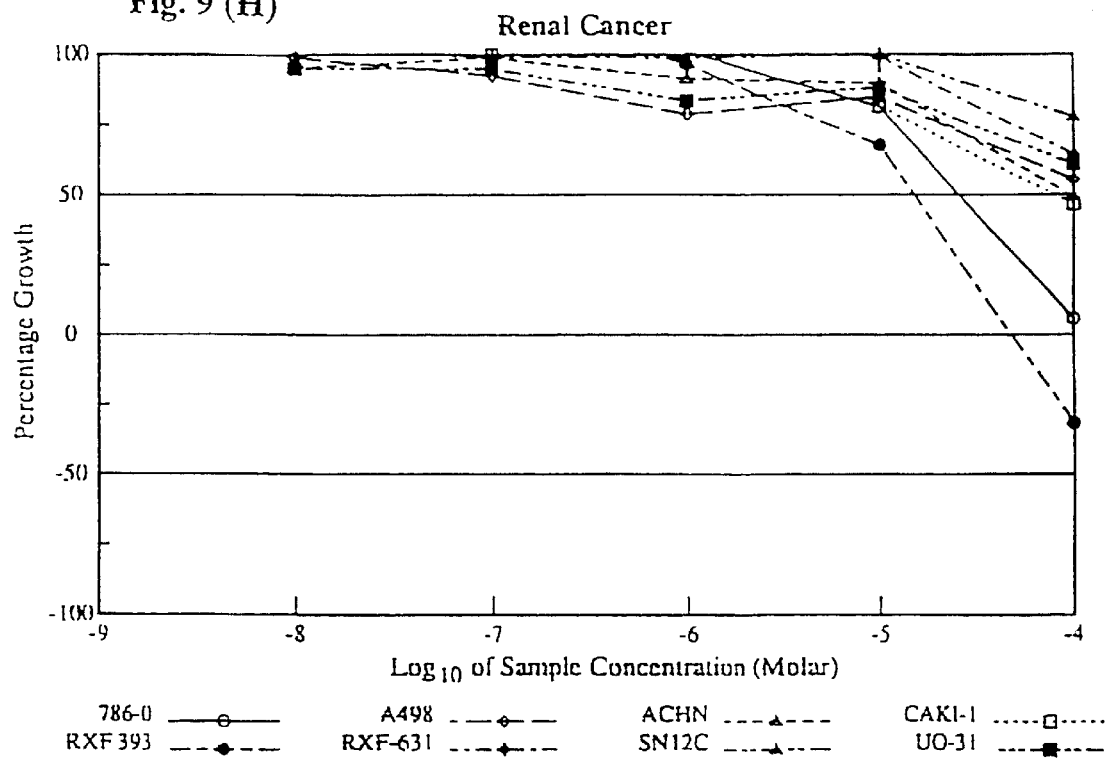
Fig. 9 (H) Renal Cancer

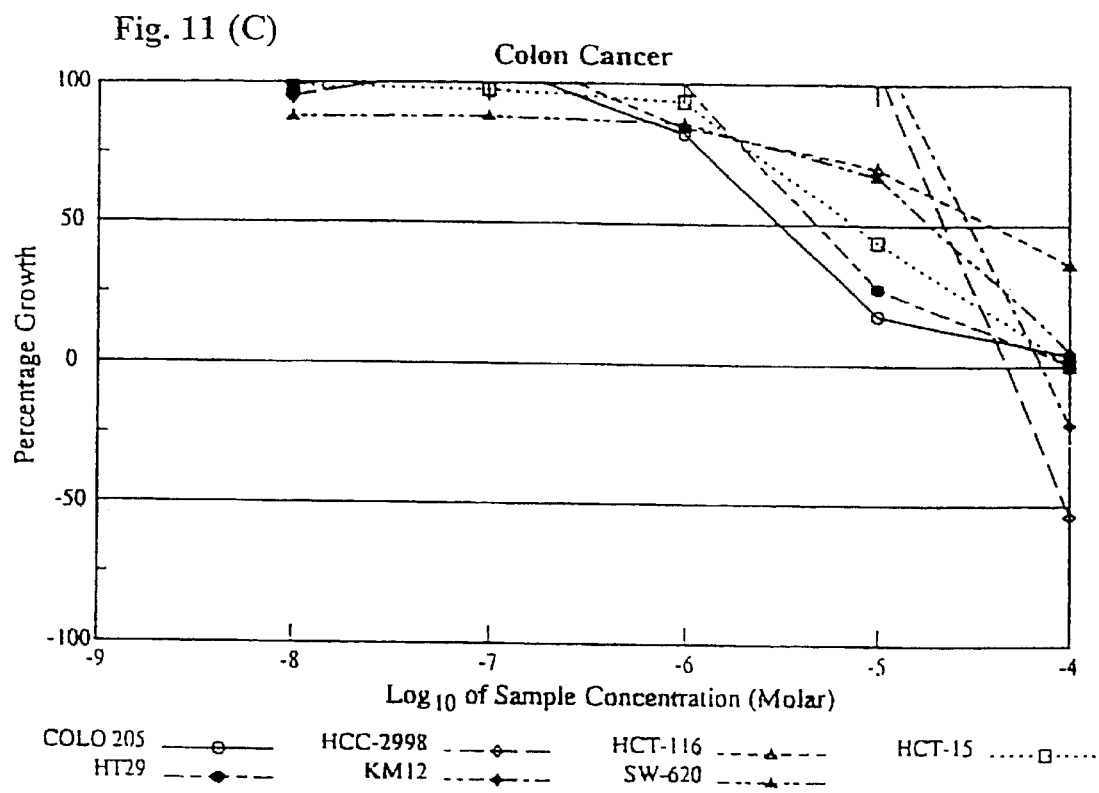
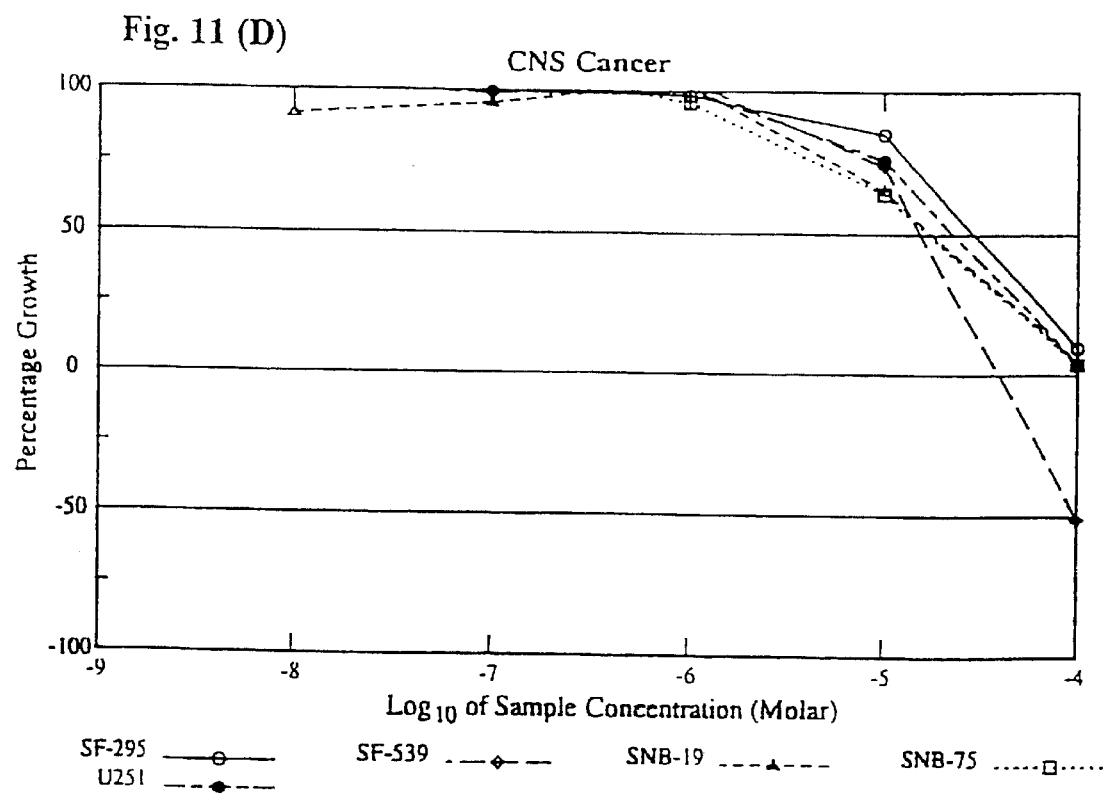

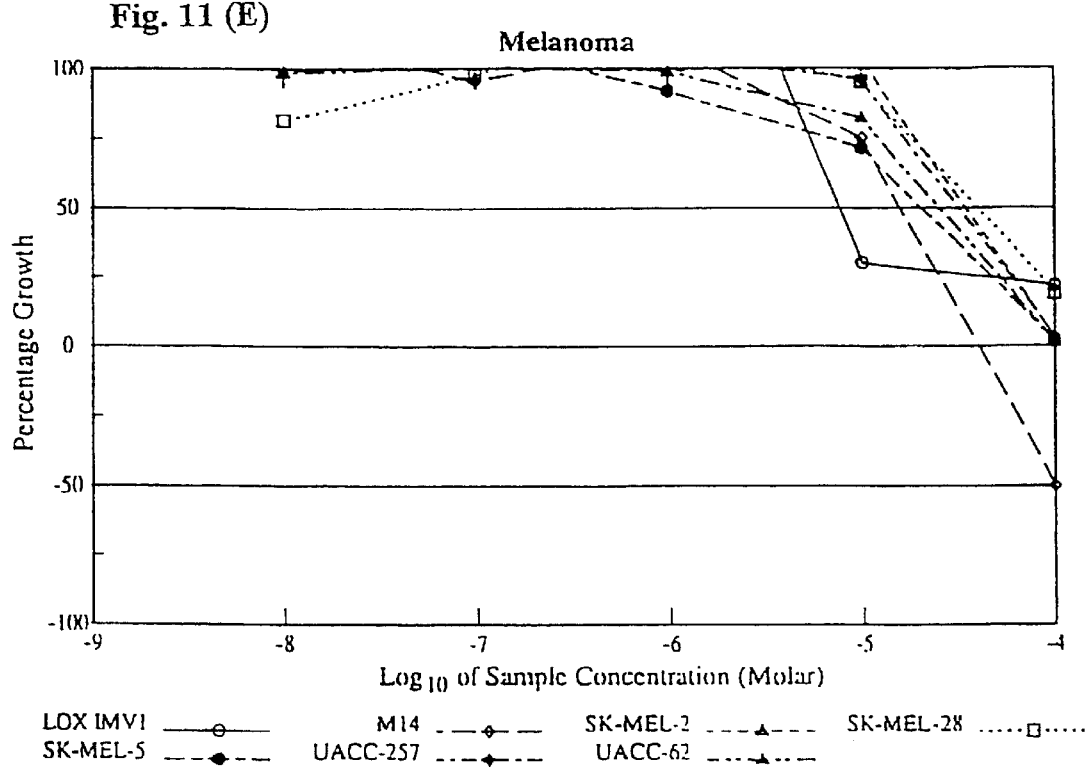
Fig. 11 (E) Melanoma
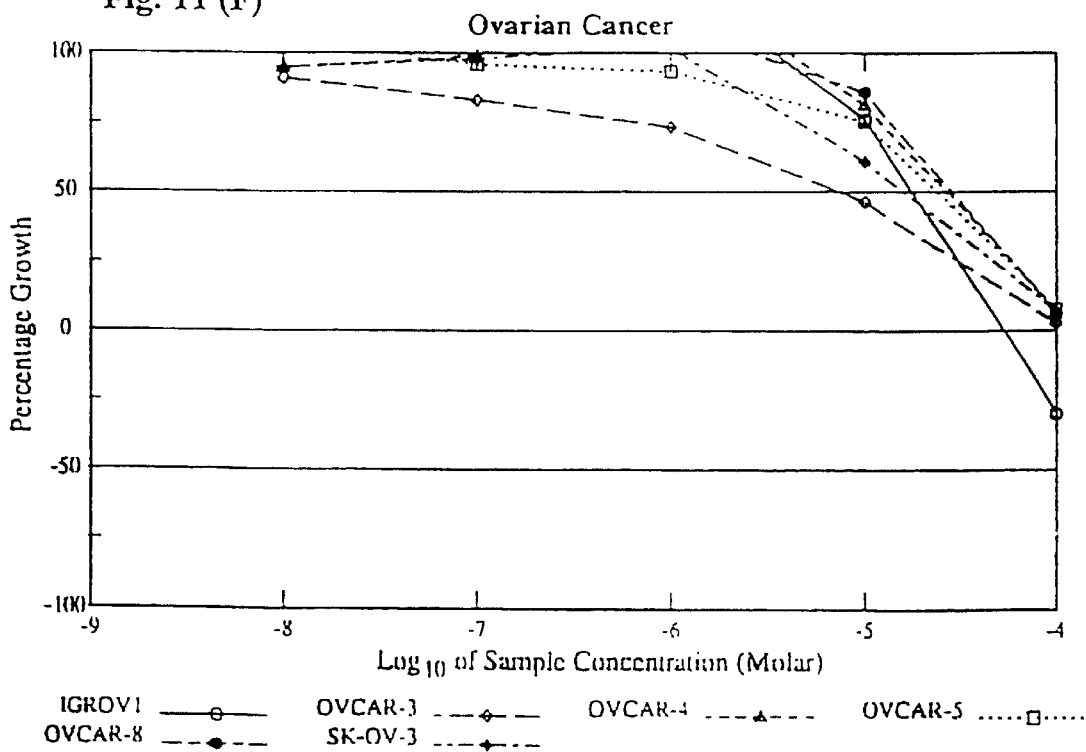
Fig. 11 (F) Ovarian Cancer

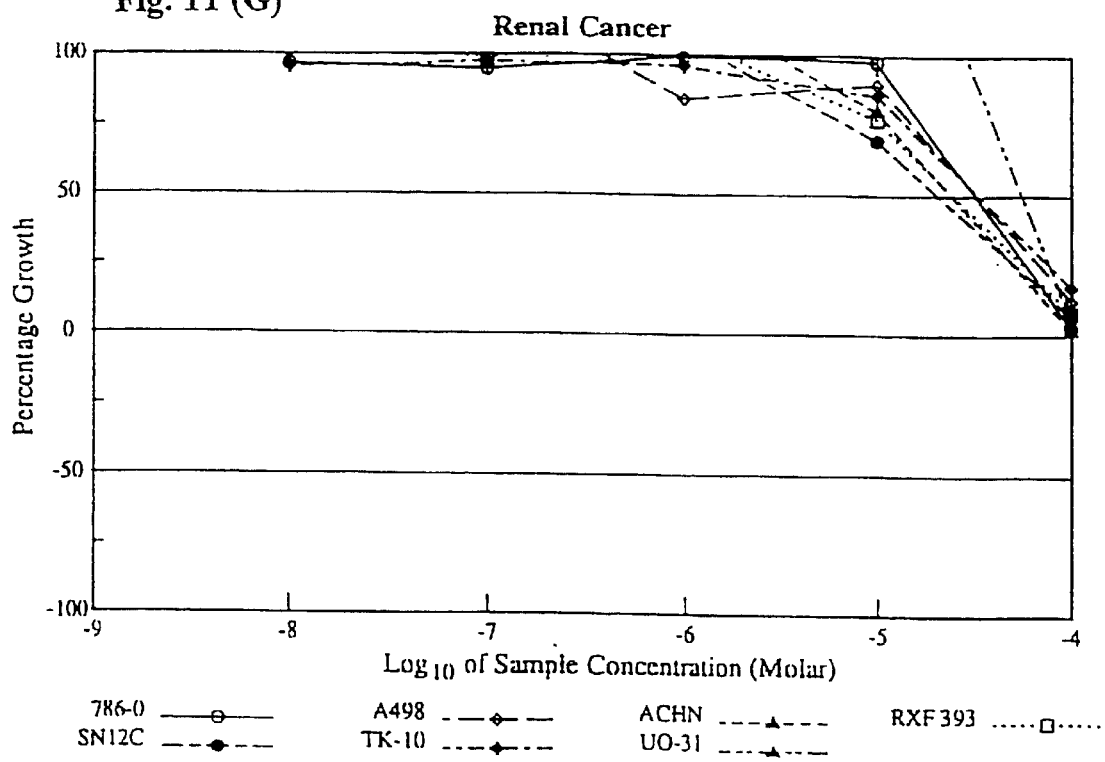
Fig. 11 (G) Renal Cancer
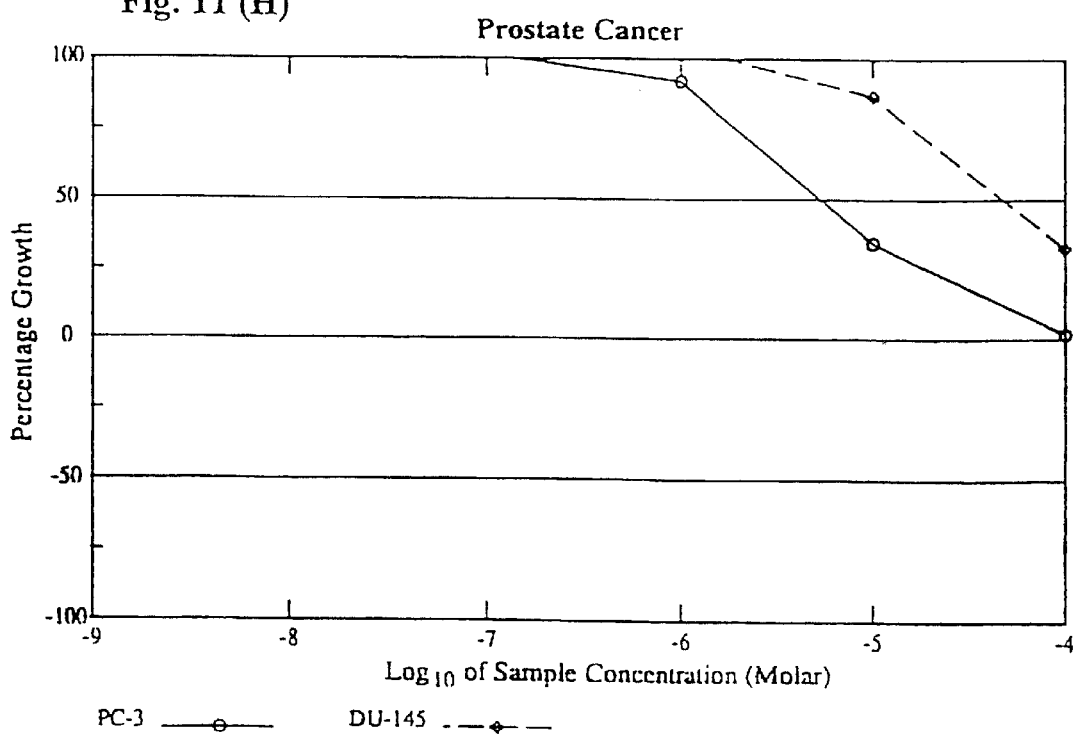
Fig. 11 (H) Prostate Cancer

Fig. 12(C)

| Panel/Cell Line | Log$_{10}$ LC50 | LC50 |
|---|---|---|
| Leukemia | | |
| CCRF-CEM | > -4.00 | |
| HL-60(TB) | > -4.00 | |
| K-562 | > -4.00 | |
| MOLT-4 | > -4.00 | |
| RPMI-8226 | > -4.00 | |
| SR | > -4.00 | |
| Non-Small Cell Lung Cancer | | |
| A549/ATCC | > -4.00 | |
| EKVX | > -4.00 | |
| HOP-62 | > -4.00 | |
| HOP-92 | > -4.00 | |
| NCI-H23 | > -4.00 | |
| NCI-H322M | > -4.00 | |
| NCI-H460 | > -4.00 | |
| NCI-H522 | > -4.00 | |
| Colon Cancer | | |
| COLO 205 | > -4.00 | |
| HCC-2998 | -4.02 | |
| HCT-116 | > -4.00 | |
| HCT-15 | > -4.00 | |
| HT29 | > -4.00 | |
| KM12 | > -4.00 | |
| SW-620 | > -4.00 | |
| CNS Cancer | | |
| SF-295 | > -4.00 | |
| SF-539 | -4.01 | |
| SNB-19 | > -4.00 | |
| SNB-75 | > -4.00 | |
| U251 | > -4.00 | |
| Melanoma | | |
| LOX IMVI | > -4.00 | |
| M14 | > -4.00 | |
| SK-MEL-2 | > -4.00 | |
| SK-MEL-28 | > -4.00 | |
| SK-MEL-5 | > -4.00 | |
| UACC-257 | > -4.00 | |
| UACC-62 | > -4.00 | |
| Ovarian Cancer | | |
| IGROV1 | > -4.00 | |
| OVCAR-3 | > -4.00 | |
| OVCAR-4 | > -4.00 | |
| OVCAR-5 | > -4.00 | |
| OVCAR-8 | > -4.00 | |
| SK-OV-3 | > -4.00 | |
| Renal Cancer | | |
| 786-0 | > -4.00 | |
| A498 | > -4.00 | |
| ACHN | > -4.00 | |
| RXF 393 | > -4.00 | |
| SN12C | > -4.00 | |
| TK-10 | > -4.00 | |
| UO-31 | > -4.00 | |
| Prostate Cancer | | |
| PC-3 | > -4.00 | |
| DU-145 | > -4.00 | |
| Breast Cancer | | |
| MCF7 | > -4.00 | |
| NCI/ADR-RES | > -4.00 | |
| MDA-MB-231/ATCC | > -4.00 | |
| MDA-MB-435 | > -4.00 | |
| MDA-N | -4.08 | |
| BT-549 | > -4.00 | |
| T-47D | > -4.00 | |
| MG_MID | -4.00 | |
| Delta | 0.03 | |
| Range | 0.08 | |

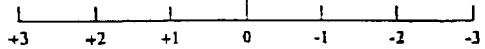

CYCLIN DEPENDENT KINASE (CDK)4 INHIBITORS AND THEIR USE FOR TREATING CANCER

This application claims the benefit of provisional application No. 60/044,256 filed Apr. 28, 1997.

FIELD OF THE INVENTION

The present invention concerns compounds that inhibit cyclin-dependent kinases, particularly the cyclin-dependent kinase CDK4, and methods for treating cancers using such compounds.

BACKGROUND OF THE INVENTION

Physiology

In a normal cell CDK4:cyclin D kinase holoenzyme phosphorylates the retinoblastoma protein (Rb) to form hyperphosphorylated retinoblastoma-phosphate (Rb-p). The hyperphosphorylation of retinoblastoma protein results in the release of Rb-p associated transcription factors that allow cell cycle progression beyond the G1 checkpoint, thereby promoting cell proliferation (Schrr et al., U.S. Pat. No. 5,723,313, (1998)).

The p16 gene (also known as CDKN2, MST1, and CDK4I) encodes the protein p16$^{INK4A}$, which inhibits the cyclin-dependent kinase (CDK)4:cyclin D complex (Serrano, et al., Nature 366: 704–7 (1993)). Defects in the p16/CDK4:cyclinD/Rb pathway may lead to tumor formation. Genetic alteration or over expression of CDK4 and CyclinD1 has been observed in various tumor cell types. In addition, alterations of p16 have been described in various histologic types of human cancers including retinoblastoma, astrocytoma, melanoma, leukemia, breast cancer, head and neck squamous cell carcinoma, malignant mesothelioma, and lung cancer (Kamb et al., Science 264: 436–40 (1994); Noborie et al., Nature 368: 753–56 (1994); Walker et al., Cancer Res. 55: 20–3 (1995) and Nakagawa et al., Oncogene 11: 1843–51 (1995)).

Acridones and Benzothiadiazines

Acridones and benzothiadiazines (BTDs) are classes of known cyclic aryl compounds. Certain known acridones or BTDs have pharmacological effects. For example, BTDs have been investigated as diuretics (See de Tullio et al., *J. Med. Chem*). Fajans and Floyd (*Ann. Rev. Med.* 30:313–329, 1982) disclose the use of "diuretic benzothiadiazine, e.g. trichlormethiazide" as a hyperglycemic in the treatment of insulinomas. Fajans and Floyd, however, do not teach the use of BTDs to affect cancers directly. The prior art, as understood, does not appear to teach the use of BTDs for their direct antineoplastic effect in the specific inhibition of CDK4 dependent tumors.

Particular acridones and acridines are known. For example, ($C_{18}H_{19}N_3O_2$—HCl) has been mentioned in a paper concerned with the anti-tumor activity of linear tricyclic carboxamides (Palmer et al., J. Med. Chem (US) 31 (4) pgs.707–721, 1988). Interestingly, the Palmer et al. paper states that this compound is "inactive" (page 711, column 1, paragraph 3).

The basic thioacridone ring structure was described in DeLeenheer et al., *J. Pharm. Sci.* 60:1238–1239, 1971, and is shown below.

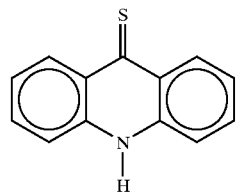

1-nitro-9-acridone, 1-nitro-10-(3-N,N-dimethylaminopropryl)-9-acridone, 1-amino-2,4-diethylthio-9-acridone and a number of acridine derivatives have been disclosed by Weltrowski et al. (*Pol. J. Chem Technol.* 56:77–82, 1982). This paper, however, deals exclusively with the synthesis of nitroacridines and does not discuss any biological activity or mechanism of biological action. But, the title of the Weltrowski article refers to tumor inhibition, and the footnote states that the work was supported by the Polish National Cancer Program.

SUMMARY OF THE INVENTION

The present invention concerns acridones, benzothiadiazines and derivatives thereof that are useful for treating cancers. The invention also concerns methods for using these compounds as CDK4 inhibitors to treat cancers.

There are a number of dreadful and relatively common cancers that have been shown to involve alterations in p16. These cancers include lung cancer, breast cancer, melanoma, leukemia, retinoblastoma, astrocytoma, head and neck squamous cell carcinoma and malignant mesothelioma. Expression of normal p16 protein in tumor cells with alterations of p16 results in restoration of cell-cycle regulation, decreased cell growth and decreased tumorigenicity in vivo. Because the only known function of p16 is inhibition of CDK4 kinase activity, cancers with alterations of p16, including those listed above, are likely to be sensitive to CDK4 inhibitors. Prior inhibitors of cyclin-dependent kinases, such as flavopiridole, staurosporin, and UCN-01, inhibit CDC2 and CDK2 as well as the intended target, CDK4. This lack of specificity produces pathological side effects, such as bone marrow and gastrointestinal toxicities, and limits their clinical application.

As a result, there is a need for drugs for treating CDK4 sensitive neoplasms that minimize toxic side effects caused by concomitant inhibition of CDC2 and CDK2. The compounds claimed in this application inhibit CDK4 to a far greater extent than CDC2 or CDK2 and therefore satisfy this need.

One example of a novel compound of the present invention is 3-amino-9-thio(10H)-acridone. This compound and others can be used to form therapeutic compositions. One embodiment of such a composition comprises a therapeutically effective amount of a compound selected from the group consisting of a benzothiadiazine, a thioacridone, or mixtures thereof. The compound has an $IC_{50}$ for CDK4 of less than about 10 μM, preferably from about 1 μM to about 7 μM, an $IC_{50}$ for CDC2 of greater than about 60 μM, preferably greater than about 100 μM, an $IC_{50}$ for CDK2/A of greater than about 100 μM, an $IC_{50}$ for CDK2/E of greater than about 80 μM, and preferably greater than about 100 μM.

The specificity of the compounds for inhibiting CDK4 can be expressed as a ratio of the $IC_{50}$ values for other enzymes relative to CDK4. Such compositions typically comprise a compound selected from the group consisting of a benzothiadiazine, a thioacridone, or mixtures thereof, the compound having an $IC_{50}$ ratio for CDC2:CDK4 of greater than about 8.5, typcially greater than about 20, preferably greater than about 60; an $IC_{50}$ ratio for CDK2/A:CDK4 of greater than about 14, typically greater than about 20, and preferably greater than about 60; and an $IC_{50}$ ratio for CDC2/E:CDK4 of greater than about 11.5, typically greater than about 20, and preferably greater than about 60.

The invention also provides a composition comprising an effective amount of a compound according to Formula 1

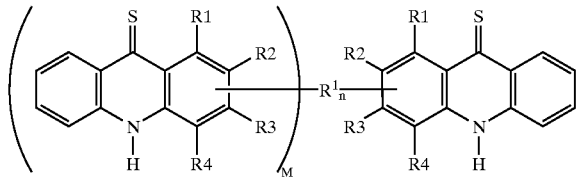

where m is 0 or 1, n=m, $R_1$—$R_4$ are independently selected from the group consisting of H, —$NH_2$ and lower alkoxy, where with m=1 one of $R_1$—$R_4$ is an amine bonded to R' to form an arylamide, or Formula 2

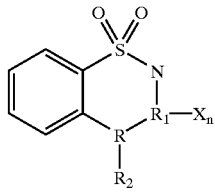

where R and $R_1$ are independently carbon or nitrogen, where if $R_1$=carbon X is hydrogen, halogen, aryl or alkoxy, and $R_2$ is selected from the group consisting of lower alkyl and aryl amino. The composition also can comprise mixtures of compounds satisfying Formula 1 and/or Formula 2. The composition can further include, without limitation, additives selected from the group consisting of carriers, diluents, excipients, diagnostics, direct compression buffers, buffers, stabilizers, fillers, disintegrates, flavors, colors, and mixtures thereof.

A method for inhibiting the growth of living cells also is described. The method comprises providing a compound selected from the group consisting of a benzothiadiazine, a thioacridone, or mixtures thereof, as described above. An effective amount of the compound, a mixture of compounds, or a composition comprising the compound or mixture of compounds, is administered to a subject to inhibit the growth of living cells.

BRIEF DESCRIPTION OF THE DRAWINGS

FIGS. 4(A)–4(C) shows mean plots of data from FIGS. 3A–3I, wherein the left-hand mean plot is of $GI_{50}$ data, the middle mean plot is of TGI data, and the right-hand mean plot is of $LC_{50}$ data.

FIGS. 8(A)–8(C) shows mean plots of data from FIGS. 7A–7I, wherein the left-hand mean plot is of $GI_{50}$ data, the middle mean plot is of TGI data, and the right-hand mean plot is of $LC_{50}$ data.

FIGS. 12(A)–12(C) shows mean plots of data from FIGS. 11A–11I, wherein the left-hand mean plot is of $GI_{50}$ data, the middle mean plot is of TGI data, and the right-hand mean plot is of $LC_{50}$ data.

DETAILED DESCRIPTION OF THE PREFERRED EMBODIMENTS

DEFINITIONS

Figure 1:
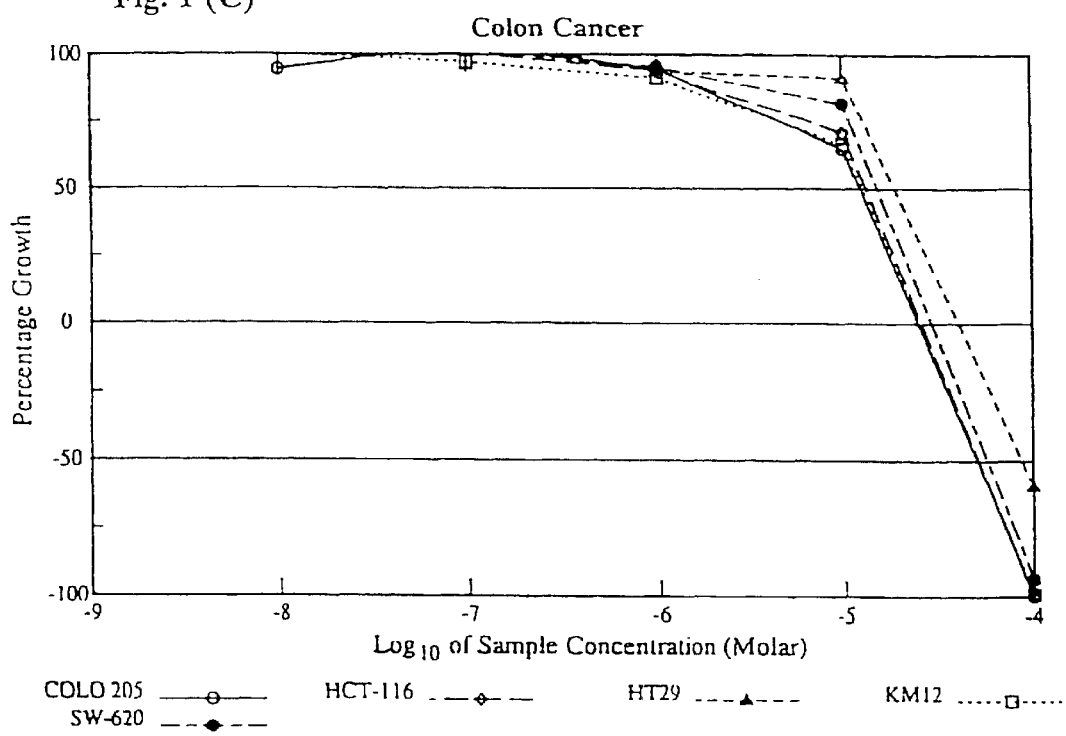
FIGS. 1(A)–1(I) are dose-response curves showing the effect of Compound 5 on various cancer cell lines in culture.
Figure 1:
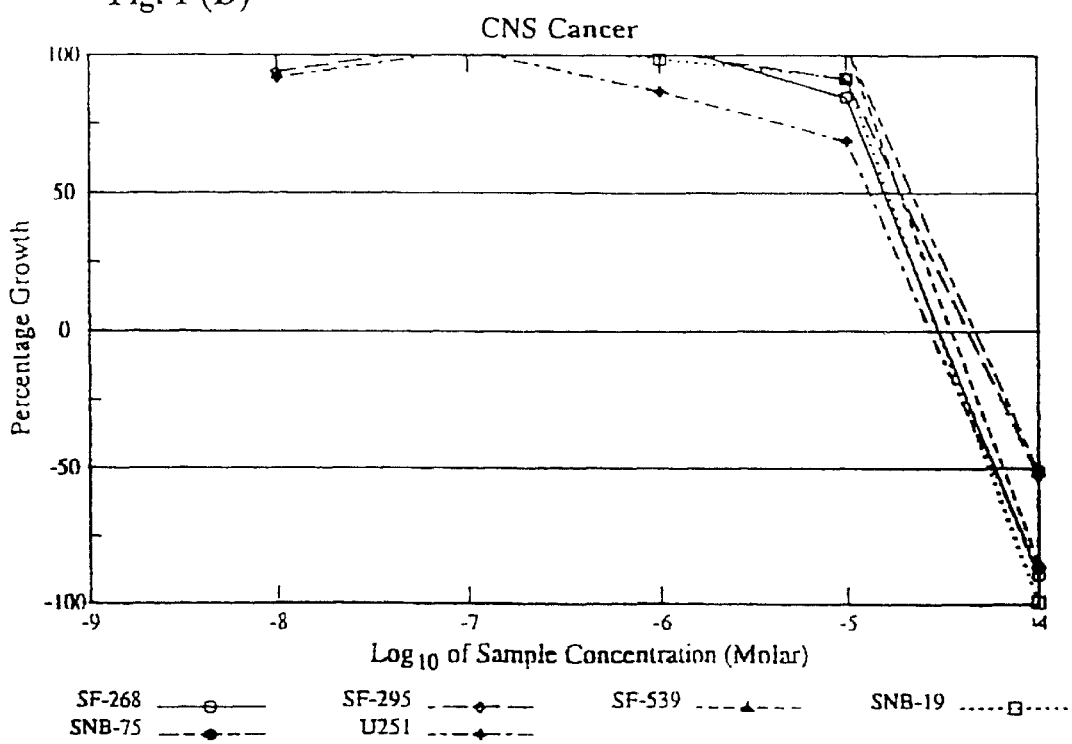
Figure 1:
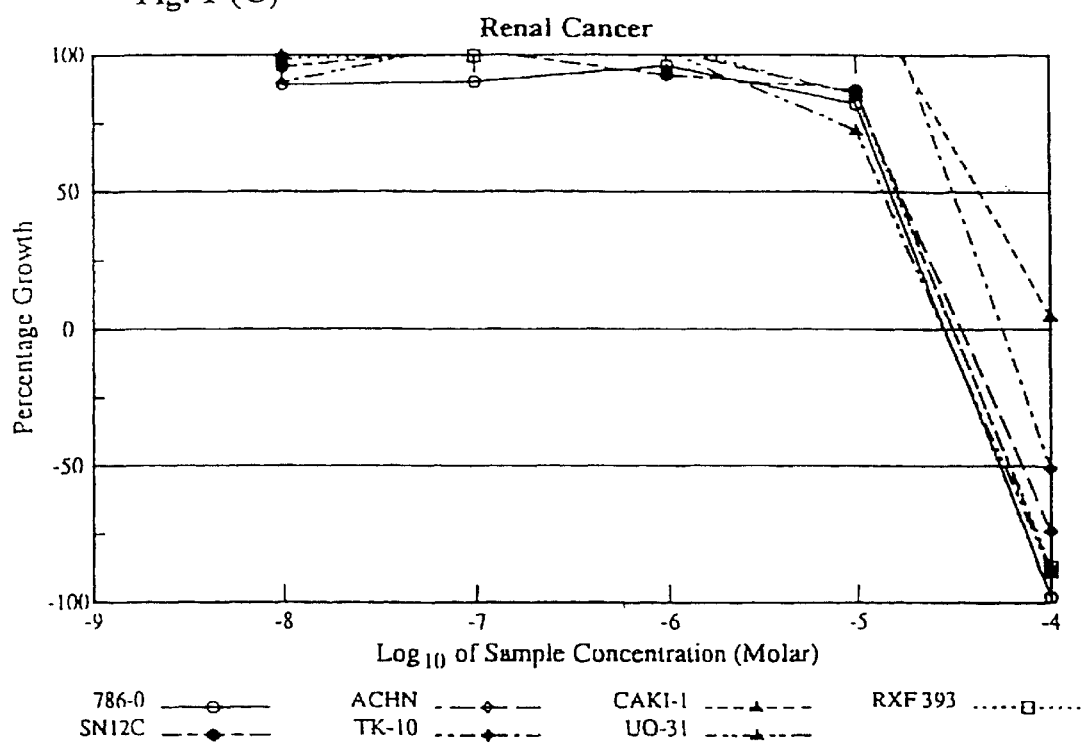
Figure 1:
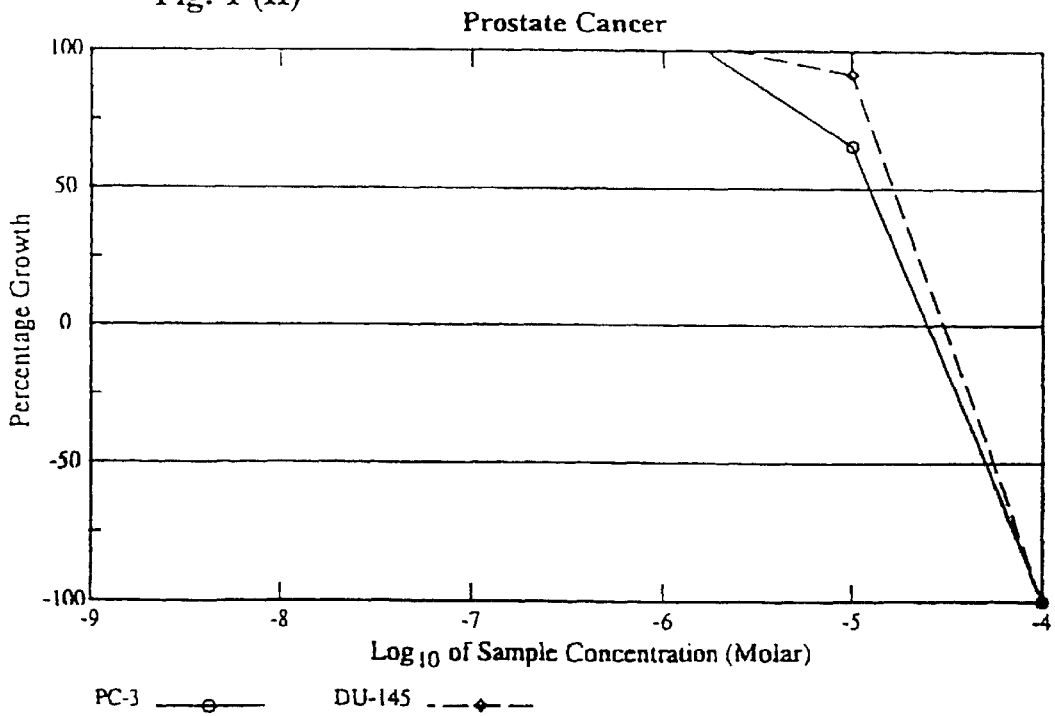

Particular terms and phrases used herein typically have the meanings set forth below. These definitions are provided solely for convenience and should not be interpreted to limit the invention to a scope less than that known to a person of ordinary skill in the art.

"3-ATA" means 3-amino-9-thio(10H)-acridone.

"BTD" means benzothiadiazine.

"Neoplasm" and "cancer" both refer to any cell or tissue wherein growth and cell division have become uncoupled from the normal regulatory constraints of the cell cycle to produce a pathological state.

"Tumor" is any neoplasm and includes both solid and non-solid neoplasms.

"Inhibitory concentration" or "$IC_{50}$" means the drug concentration at 50% inhibition of kinase activity ($\mu M$).

"Therapeutically effective anti-neoplastic amount" means an amount sufficient to prevent advancement, or to cause regression of, a neoplasm.

"CDK4" and "CDK4/A" refer to the CDK4:cyclin D1 kinase holoenzyme.

"CDK4 inhibitor" refers to compounds that inhibit the kinase activity of CDK4.

"CDK4 inhibition" refers to inhibition of the kinase activity of CDK4.

"CDK2", when used alone, refers to both CDK2:Cyclin A and to CDK2:Cyclin E

"CDC2" and "CDC2/A" refer to CDC2:Cyclin A holoenzyme.

"CDK2/A" refers to CDK:Cyclin A holoenzyme.

"CDK2/E" refers to CDK2:Cyclin E holoenzyme.

"Cancers specifically inhibited by CDK4 inhibitors" means all neoplastically transformed cells and tissues, the growth and/or cell cycle of which is affected by a CDK4 inhibitor.

A cell "susceptible to CDK4 inhibitors" or "susceptible to CDK4 inhibition" is a cell for which CDK4 inhibitors alter growth or cell cycle.

"Specific inhibition" or "specific inhibitory activity" of the compounds of the invention means that the compounds inhibit CDK4 to a greater extent than they inhibit CDC2 or CDK2.

"Lower-alkyl" means a single-bonded branched or unbranched hydrocarbon chain having from about one to about ten carbon atoms, including all position and stereoisomers.

Compounds

Compounds of the present invention satisfy either Formula 1 (acridone-like structures) or Formula 2 (benzothiadiazine-like structures) below.

FORMULA 1

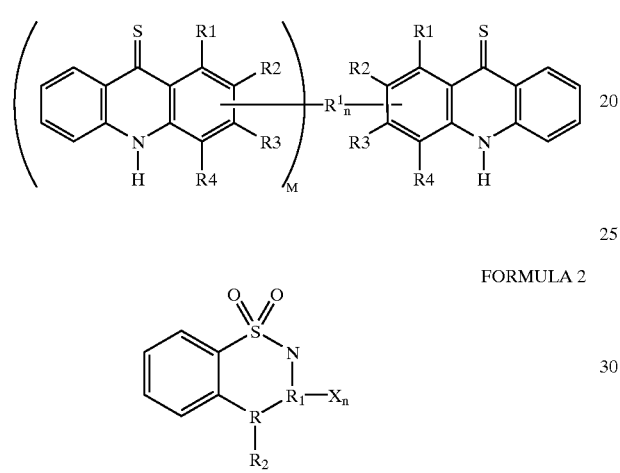

FORMULA 2

With reference to Formula 1, m is 0 or 1, and n=m. $R_1$–$R_4$ are independently selected from the group consisting of H, —$NH_2$ and lower alkoxy. With m=1, at least one of $R_1$–$R_4$ is an amine and R' is bonded to the amine to form an arylamide.

With reference to Formula 2, R and $R_1$ are independently carbon or nitrogen. If $R_1$=carbon X is hydrogen or halogen. $R_2$ is selected from the group consisting of lower alkyl and aryl amino.

Compounds according to both Formula 1 and 2 show specific inhibitory activity against CDK4. This inhibition may be due to inhibition of formation of the CDK4:cyclinD kinase holoenzyme or to competitive binding of the inhibitor with the kinase substrate or to ATP-dependent competitive effects or some other interaction.

Structural formulas for particular compounds of the invention are provided below as Compounds 1–6.

COMPOUND 1

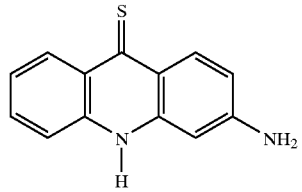

3-Amino-10H-acridine-9-thione

COMPOUND 2

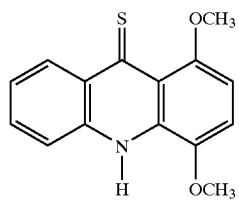

1,4-Dimethoxy-10H-acridine-9-thione

COMPOUND 3

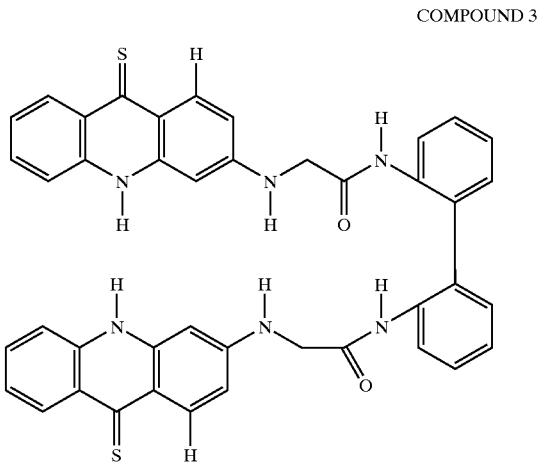

2,2'-Biphenyldiamine, bis[N,N'-[3-(amidonmethylamino)-10H-acridine-9-thione]]

COMPOUND 4

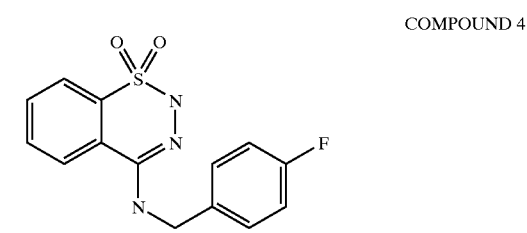

4-(4-Fluorobenzylamino)-1,2,3-benzothiadiazine-1, 1-dioxide

COMPOUND 5

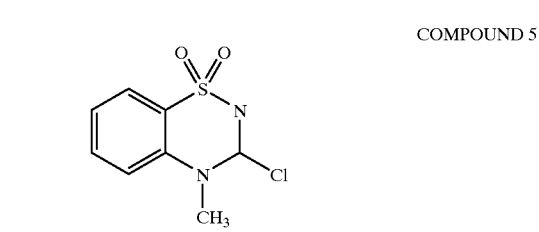

3-Chloro-4-methyl-4H-benzo[e][1,2,4]thiadiazine 1, 1-dioxide

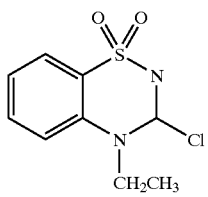

COMPOUND 6

3-Chloro-4-ethyl-4H-benzo[e][1,2,4]thiadiazine 1,1-dioxide

Synthesis of Compounds

The compounds of the invention were obtained from and are maintained at the Drug Synthesis and Chemistry Branch, National Cancer Institute. Syntheses of related compounds are known in the literature. For example, the following references described the syntheses of certain related compounds: Pascal de Tullio et al., "3- and 4-Substituted 4H-Pyrido[4,3-e]-1,2,4-thiadiazine 1,1-Dioxides as Potassium Channel Openers: Synthesis, Pharmacological Evaluation, and Structure—Activity Relationships," *J. Med. Chem.*, Vol. 39, pp. 937–948 (1996); Bernard A. Dumaitre et al., U.S. Pat. No. 5,604,237; Hamprecht et al., U.S. Pat. No. 4,075,004; Magatti U.S. Pat. No. 4,468,396; Brian D. Palmer et al., "Potential Antitumor Agents. 54. Chromophore Requirements for in Vivo Antitumor Activity Among the General Class of Linear Tricyclic Carboxamides," *J. Med. Chem.*, Vol. 31, pp. 707–712 (1988); N. Dodic et al., "Synthesis and Activity Against Multidrug Resistance in Chinese Hamster Ovary Cells of New Acridone-4-Carboxamides," *J. Med. Chem.*, Vol. 38, pp. 2418–2426 (1995); Marek Welt4rowski et al., "Research on Tumour Inhibiting Compounds, Part LXX, Reactions of 1-Nitroacridines with Ethanethiol," *Polish Journal of Chemistry*, pp. 77–82 (1982).

Compositions

Compounds satisfying either Formula 1 or 2 above may be formulated as pharmacological compositions containing a therapeutically effective anti-neoplastic amount of the compound(s). Such compositions may further comprise, without limitation, inert carriers, diluents, excipients, diagnostics, direct compression buffers, buffers, stabilizers, fillers, disintegrates, flavors, colors, other materials conventionally used in the formulation of pharmacological compositions and mixtures thereof.

Method

The method of the present invention comprises administering to a subject a therapeutically effective anti-neoplastic amount of a compound, mixture of compounds, or composition or compositions comprising the compound or compounds; to effect a change in the physiology of a neoplasm. One of ordinary skill in the art will realize that the therapeutically effective anti-neoplastic amount may vary. Antitumor agents generally are dosed as mass-per-unit-body surface area of the subject. It currently is believed that a therapeutically effective anti-neoplastic amount of the disclosed compounds may be from about 1 μg to about 10 g per $m^2$ of body surface area, more preferably from about 1 mg to about 900 mg per $m^2$ of body surface area. Moreover, it typically is desirable to provide as large a dose as a subject will tolerate.

The compound(s) or compositions may be administered by any number of methods including, but not limited to, intravenously, topically, orally, intramuscularly, subcutaneously, intraperitoneally. Currently, intravenous and oral administration are considered the preferable routes of administration.

Biological Methods and Results

Tables 1 and 2 provide $IC_{50}$ data for compounds representative of the present invention. These tables demonstrate that the $IC_{50}$ value of compounds according to the present invention for CDK4 generally is less than about 10 μM, and preferably is less than about 7 μM. The best compound, solely in terms of its $IC_{50}$ value for CDK4, is compound 5 with an $IC_{50}$ of 1.1 μM. But, compounds 7 and 8 also have $IC_{50}$ values of less than 2 μM, namely 1.4 μM and 1.7 μM respectively.

The compounds of the present invention also are quite specific for inhibition of CDK4. This is reflected in the $IC_{50}$ ratios reported in Tables 1 and 2, with the $IC_{50}$ for CDK4 being the denominator in the ratio e.g., ($IC_{50}$ CDC2)/($IC_{50}$ CDK4). Thus, the lower the $IC_{50}$ is for CDK4 and the higher it is for the other complexes, the more specific the compound is for CDK4.

The CDC2/A:CDC4 ratios in Tables 1 and 2 range from about 8 to greater than 72. The best compound with respect to specificity between CDK4 and CDC2 is compound 7, with an $IC_{50}$ for CDK4 of 1.4 μM, an $IC_{50}$ for CDC2 of >100 μM, and an ($IC_{50}$ CDC2):($IC_{50}$ CDK4) of >71.5.

Compound 3 (3-ATA) has an $IC_{50}$ for CDK4 of 6.8 μM, an $IC_{50}$ for CDC2 of 60 μM, and an ($IC_{50}$ CDC2):($IC_{50}$ CDK4) of 8.8.

Compound 4 has an $IC_{50}$ for CDK4 of 2.2 μM, an $IC_{50}$ for CDC2 of >100 μM, and an ($IC_{50}$ CDC2):($IC_{50}$ CDK4) of >45.

Compound 5 has an $IC_{50}$ for CDK4 of 1.1 μM, an $IC_{50}$ for CDC2 of >70 μM, and an ($IC_{50}$ CDC2):($IC_{50}$ CDK4) of >63.6.

Compound 6 has an $IC_{50}$ for CDK4 of 5.0 μM, an $IC_{50}$ for CDC2 of >100 μM, and an ($IC_{50}$ CDC2):($IC_{50}$ CDK4) of >71.5.

Compound 8 has an $IC_{50}$ for CDK4 of 1.7 μM, an $IC_{50}$ for CDC2 of >100 μM, and an ($IC_{50}$ CDC2):($IC_{50}$ CDK4) of >58.8.

$IC_{50}$ and $IC_{50}$ ratio data for other kinases are summarized in Tables 1 and 2 below.

Compounds satisfying Formulas 1 and 2 have been subjected to biological assays to determine inhibition of the cyclin dependent kinases CDK4, CDC2, CDK2/A and CDK2/E. The experimental procedures for these biological methods and assays are provided below in the Examples. Results of these assays for representative compounds are provided below in Tables 1 and 2.

TABLE 1

| Formula Name | CDK4/D1 | CDC2/A | Ratio CDC2A:CDK4 | CDK2/A | Ratio CDK2/A:CDK4 | CDK2/E | Ratio CDK2/E:CDK4 |
|---|---|---|---|---|---|---|---|
| $IC_{50}$ value ($\mu$M) | | | | | | | |
| Compounds structurally related to 3-ATA | | | | | | | |
| Formula 3 | 6.8 | 60 | 8.8 | >100 | >14.7 | 80 | 11.8 |
| Formula 4 | 2.2 | >100 | >45 | >100 | >45 | >100 | >45 |
| Formula 5 | 1.1 | 70 | 63.6 | >100 | >91 | >100 | >91 |

TABLE 2

| Formula Name | CDK4/D1 | CDC2/A | Ratio CDC2A:CDK4 | CDK2/A | Ratio CDK2/A:CDK4 | CDK2/E | Ratio CDK2/E:CDK4 |
|---|---|---|---|---|---|---|---|
| $IC_{50}$ value ($\mu$M) | | | | | | | |
| Compounds structurally related to BTD (NSC645787) | | | | | | | |
| Formula 6 | 5.0 | >100 | >20 | >100 | >20 | >100 | >20 |
| Formula 6 | 1.4 | >100 | >71.5 | >100 | >71.4 | >100 | >71.4 |
| Formula 7 | 1.7 | >100 | >58.8 | >100 | >58.8 | >100 | >58.8 |

An $IC_{50}$ of 10 $\mu$M is generally considered effective for these compounds, but effectiveness should be considered in the light of specificity for CDK4.

EXAMPLES

The following examples are provided to illustrate certain features of the invention and are not meant to limit the invention to any particular embodiment.

Example 1

This example describes in detail how the compounds of the invention were identified and tested to determine their specific inhibitory activity against cyclin dependent kinases. Essentially, the methods of this example include three stages: (1) determining which cell lines contain p16 alterations, (2) determining which drugs are most active against p16 altered cells, and (3) determining the CDK4 kinase inhibitory activity of selected, screened compounds.

Methods

Cell lines, compounds, and in vitro sensitivity testing. Exponentially growing cultures of the nine non-small cell lung, eight melanoma, eight renal, eight breast, seven colon, six brain, six leukemia, six ovarian, and two prostate cancer cell lines from the NCI drug screen panel were used. Compounds were obtained from the Drug Synthesis and Chemistry Branch, National Cancer Institute. In vitro anti-tum or activity of compounds was determined using a sulforhodamine-B assay in the 60 human cancer cell lines of the NCI drug screen panel.

Polymerase chain reaction-single strand conformation polymorphism (PCR-SSCP) and DNA sequence analysis of p16. Approximately $1.5 \times 10^5$ tumor cells were washed with PBS, lysed in 100 $\mu$l proteinase K solution [200 mg/ml, 50 mM Tris-HCl (pH8.5), 1 mM EDTA(pH8.0), and 0.5% Tween, 20], and incubated at 50° C. for 4 h. One microliter of this lysate was used as template in a 10 $\mu$l PCR for each of seven oligonucleotide primer pairs which span the coding region and splice junctions of exons 1 and 2 of p16 twice. SmaI-digested (for primer pair 2D) or undigested PCR products were subjected to SSCP. The presence of bands with an abnormal migration pattern was confirmed by repeating PCR-SSCP at least once prior to extraction of the band, cloning into pT7Blue(R) T-vector (Novagen, Madison, Wis.), and DNA sequence analysis by the dideoxy chain termination method using Sequenase™ (US Biochemical, Cleveland, Ohio). The presence of intact genomic DNA was confirmed by amplification of a 536-bp fragment of the β-globin gene. The p16 sequence published by Okamoto et al. (GenBank accession number L27211) was used as reference for DNA and amino acid numbering.

Reverse Transcription (RT)-PCR and Southern blot hybridization analyses of p16. Total RNA was isolated from $1 \times 10^6$ cells of each cell line using an RNA isolation kit (5' prime 3' prime,Inc., Boulder, Colo.), RT-PCR was performed for the p16 gene as previously described. PCR products were separated by agarose gel electrophoresis, transferred to a nylon membrane, and hybridized with a 388-bp p16 exon 1 genomic fragment defined by oligonucleotides 2F and 1108R. Expression of the glyceraldehyde-3-phosphate (GAPDH) gene was examined to assure the presence of intact mRNA in each sample by addition of a gene-specific oligonucleotide, G3PD-2R (5'-GATACATGACAAGGTGCGGC-3') to the reverse transcriptase reaction followed by 40 cycles of PCR (30 sec at 94° C., 30 sec at 55° C., and 1 min at 72° C. using oligonucleotides, G3PD-1F (5'TCGTGGAAGGACTCATGACC-3') and G3PD-1R (5' ACATGGCAACTGTGAGGAGG-3').

Immunoblot analysis. Cells ($1 \times 10^7$) were washed with PBS, resuspended in 0.4 ml of lysis buffer [50 mM Tris-HCl (pH7.4), 250 mM NaCl, 5 mM EDTA, 0.1% Nonidet P40, 50 mM NaF, and 1 mM PMSF], and centrifuged at 14,000 rpm for 20 min at 4° C. The protein concentration of the supernatant was determined using the Bio-Rad protein assay reagent (Bio-Rad, Hercules, Calif.). Fifty micrograms of total protein were mixed with an equal volume of 2×sample buffer [125 mM Tris-HCl (pH 6.8), 20% glycerol, 4% (w/v) SDS, 0.005% bromophenol blue, and 5% 2-mercaptoethanol], loaded on a 14% Tris-glycine gel, and subjected to electrophoresis at 125 V for 90 min in 1×running buffer (25 mM Tris-base, 192 mM glycine, and 0.1% SDS). The separated proteins were transferred to a nitrocellulose membrane at 25 V for 2 h in transfer buffer (12 mM Tris-base, and 96 mM glycine, 20% methanol). After 30 min incubation at room temperature in blocking solution (1×PBS, 5% powdered dry milk, and 1% BSA), the membrane was incubated at 4° C. with 1:1000 dilution of polyclonal anti-human p16 antiserum (PharMingen, San Diego, Calif.) overnight, rinsed 5 times with PBS, incubated with a mixture of 40 µl $^{125}$I-Protein A (>30 mCi/mg) in 20 ml blocking solution at 4° C. for one hour, washed again with PBS, air dried for 15 min, and subjected to autoradiography.

COMPARE analysis. The COMPARE algorithm was performed. For the identification of agents with differential activity, "GI50" values of 0 and 1 were used for p16-normal and for p16-altered cell lines, respectively. p16-altered cell lines were those with biallelic deletion, intragenic mutation, or transcriptional suppression of p16 and p16-normal cell lines were those without these abnormalities. Pearson correlation coefficients were calculated by the SAS procedure PROC CORR (SAS Institute Inc., Cary, N.C.).

GST fusion proteins. Full length p16 cDNA from cell lines containing intragenic mutations (NCI-H69, MDA-MB-435, UACC-257, and DU-145) were produced by RT-PCR using oligonucleotides MK52 (5'CGTG AATTCAAGCTTCCTCTCTGGTTCTTTCAATCGGG-3') and MK68 (5'GATGGGATCCCGGCGGC GGGGAGCAGC-3'), cloned into pGEX-5X-1 plasmid (Pharmacia Biotech, Piscataway, N.J.) and sequenced. A GST-Rb fusion plasmid encoding the larger "pocket" domain of Rb was used and GST-fusion proteins were expressed in E. coli (DH5α) and purified using glutathione sepharose (Pharmacia Biotech, Piscataway, N.J.) according to manufacturers recommendations.

In vitro kinase assay. Seventy-two hours after infection of 1×10$^7$ Sf9 cells with baculovirus containing a human CDK gene and/or a cyclin gene, cells were lysed in 250 µl of lysis buffer [50 mM HEPES (pH 7.5), 10 mM MgCl$_2$, 1 mM DTT, 5 ig/ml of aprotinin, 5 µg/ml of leupeptin, 0.1 mM NaF, 0.2 mM phenylmethylsulfonyl fluoride (PMSF), and 0.1 mM sodium orthovanadate], centrifuged, and lysates stored at −70° C. Five microliters of CDK:cyclin lysate were mixed with test compounds in 40 µl of kinase buffer (200 mM Tris-HCl, pH 8.0, 100 mM MgCl$_2$, 10 mM EGTA) and incubated at 30° C. for 30 min. About 400 ng of purified GST-Rb fusion protein and 5 µCi of γ-[$^{32}$P]ATP were added to the mixture and incubated at 30° C. for 15 min. Reactions were stopped by the addition of 250 µl of IP buffer (50 mM Tris-HCl, pH 8.0; 150 mM NaCl, 0.5% NP-40) and 15 µl glutathione sepharose. After one hour incubation at 4° C., sepharose beads were washed four times with IP buffer, mixed with 18 µl of 2×sample buffer and electrophoresed on an 8% Tris-glycine gel (Novex, San Diego, Calif.) at 125 V for 90 min. Equal recovery of GST-Rb fusion protein was confirmed by Coomassie blue staining prior to autoradiography.

CDK4 binding assay. Sf9 cells (1×10$^7$) were co-infected with baculovirus containing a cloned human CDK4 gene and/or a cyclin D1 gene in 12.5 ml of Grace's insect medium (Paragon, Baltimore, Md.) containing 10% FBS. After 40 h, cells were washed and placed in 5 ml of methionine-free medium containing 200 µCi/ml of [$^{35}$S]methionine (1000 Ci/mmole) for 4 h, followed by lysis in 250 µl. Cleared cell lysate (10 µl) was incubated with 400 ng of wildtype or mutant GST-p16 fusion proteins using the same conditions as the in vitro kinase assay. After a 30 min incubation, GST-p16 fusion protein was separated using glutathione sepharose according to manufacturer's recommendations, and electrophoresed on a 14% Tris-glycine gel (Novex, San Diego, Calif.). The gel was stained using Coomassie blue, dried, and autoradiography was performed. Equal recovery of GST-p16 fusion protein was confirmed by Coomassie blue staining. To test the effect of compounds on p16 binding to CDK4, 100 µM of each compound was incubated with CDK4:cyclin D1 lysate for 30 min prior to adding GST-p16 fusion protein.

Results

Characterization of the p16 status of the cell lines of the NCI drug screen panel. To detect genetic alternations of p16 in the 60 cell lines of the NCI drug screen panel, polymerase chain reaction-single strand conformation polymorphism (PCR-SSCP) analysis was performed for exons 1 and 2 of the p16 gene using genomic DNA. Exon 3, which encodes only four amino acids, was not examined as mutations limited to exon 3 have not been described. Among the 60 cell lines, 29 cell lines were found to lack amplifiable genomic sequences of one or both exons, indicative of a biallelic deletion involving p16. The presence of amplifiable genomic DNA in each sample was confirmed by amplification of a 536 bp fragment of the β-globin gene. Eight of the 60 cell lines contained a reproducible abnormally migrating SSCP band. DNA sequence analysis of clones of these eight abnormally migrating SSCP fragments revealed alteration of the primary sequence in each. One of these eight cell lines, HL-60, had two sites of sequence variation in exon 2 of p16, one of which was a common polymorphism at codon 148 (A148T). This polymorphism, which does not affect p16 function, was also present in the colon carcinoma cell line, KM12. Additional sequence variants not known to be polymorphisms were observed in seven (12%) of the 60 cell lines. HL-60 contained a nonsense mutation at codon 80 and HCT-116 contained a one bp insertion at codon 22–23, which results in a frameshift at codon 22 and termination after codon 42. Both of these mutations were reasoned to cause loss of p16 function. Three cell lines (MDA-MB-435, MDA-N, and M14) contained the same splice site mutation [T to C substitution at nucleotide 2 of intron 1 (I1+2$^{T-C}$)], and 2 cell lines (UACC-257 and DU-145) had distinct missense mutations. The splice site mutation resulted in aberrant splicing creating a shortened mRNA that had deletion of codons 28 to 50. The functional effect of the splice site and missense mutations was assessed by measuring the binding of GST-p16 fusion proteins to CDK4. Binding of mutant GST-p16 fusion proteins (I1+2$^{T-C}$, D84Y, and P81L) to CDK4 was 3.2%, 4.9%, and 34% of the binding ability of normal p16, respectively (p<0.0001 for each comparison, 2-tailed Student t-test). Thus, 36 of 60 (60%) cell lines of the NCI drug screen panel contained a genetic alteration (homozygous deletion or intragenic mutation) of p16 that disrupted the function of p16$^{INK4A}$.

To detect non-genetic alterations associated with loss of p16 function, p16 mRNA and protein expression were examined. Using RT-PCR and subsequent Southern blot hybridization analyses, p16 mRNA expression was undetectable in 41 of 60 (68%) cell lines examined, including 11 of 24 (46%) without detectable genetic alteration. The amplified p16 cDNAs in two cell lines (MDA-MB435 and MDA-N) were smaller than expected, consistent with altered mRNA splicing as a result of the I1+2$^{T-C}$ mutation. p16 mRNA was not detected in the third cell line (M14) with this splice site mutation. A protein of 16 kd was detected in 17 of the 60 (28%) cell lines by Western blot analysis using p16 polyclonal antiserum. The cell line with a nonsense mutation (HL60) expressed p16 mRNA but not p16 protein. The two cell lines with missense mutations (UACC-257 and DU-145) expressed both mRNA and protein. In UACC-257, a protein smaller than 16 kd was detected, perhaps the result of altered susceptibility to proteolysis of p16$^{P81L}$. A protein of 16 kd was detected in two cell lines with the splice site mutation (MDA-MB435 and MDA-N) but was absent in the third cell line with the I1+2$^{T-C}$ mutation, M14. In each cell line, absent or altered p16 protein could be attributed to mutation or transcriptional suppression. In total, 47 of the 60 (78%) cell lines of the NCI drug screen panel had an alteration of p16.

Comparison of p16 status with growth inhibitory activity. To identify compounds more active against p16-altered cells than p16-normal cells, the p16 status of the 60 cell lines was matched to the growth inhibitory (GI$_{50}$) activity of the compounds of the NCI drug screen program and ranked according to Pearson correlation coefficients using the COMPARE algorithm. The growth inhibitory activity of cephalostatin 1, a disteroidal alkaloid extracted from the marine worm, *Cephalodiscus gilchristi,* correlated best with p16 status (r=0.599). The growth inhibitory activity of five related compounds [cephalostatins 7, 9, 8, 4 and 3 were also positively correlated with p16 status (r=0.504, 0.493, 0.491, 0.461, and 0.458, respectively). Bryostatin 1, a protein kinase C activator isolated from the marine bryozoan, *Bugula neritina,* had a correlation coefficient of 0.469.

Aliquots of 26 of the 40 compounds with the highest Pearson correlation rankings were available for further in vitro analysis. These compounds were assessed for CDK4:cylin D kinase inhibitory activity using baculovirus-expressed human CDK4 and cyclin D1, and a GST-Rb fusion protein as substrate. Six of the 26 compounds examined inhibited phosphorylation of Rb protein by CDK4:cyclin D1 complex with IC$_{50}$ values ranging from 6.8 to more than 100 µM. No inhibition of GST-Rb phosphorylation by CDK4:cyclin D1 was observed in the presence of the other 20 compounds at concentrations up to 100 µM. The most potent inhibitor was 3-amino-9-thio(10H)-acridone (3-ATA; Formula 3) with an IC$_{50}$ of 6.8 µM, a value similar to the mean GI$_{50}$ (30 µM) observed for this compound in the 2 day growth assay of the NCI drug screen. Cephalostatin 1, which has potent antitum or activity in vitro (ED$_{50\ 10}$$^{-7}$ to 10$^{-9}$ µg/ml), had an IC$_{50}$ for CDK4:cyclin D1 of 20 µM and bryostatin 1 had no inhibitory activity at the highest concentration examined (100 µM).

Characterization of 3-ATA. To examine the specificity of 3-ATA inhibitory activity for CDK4:cyclin D1 kinase, we performed in vitro kinase assays using baculovirus-expressed human CDC2:cyclin A, CDK2:cyclin A, and CDK2:cyclin E complexes. 3-ATA was a less potent inhibitor of CDC2 and CDK2 kinase activities with IC$_{50}$ values at least nine-fold higher compared to the IC$_{50}$ for CDK4. The addition of 100 µM 3-ATA decreased the binding of CDK4 to normal p16 by 70% in the p16-CDK4 binding assay (p<0.0001, 2-tailed Student t-test), suggesting that 3-ATA may be acting by a mechanism similar to p16. In the CDK4 kinase assay, the addition of exogenous ATP (0 to 600 µM) did not alter the inhibitory activity of 3-ATA, suggesting that 3-ATA was not competing with ATP. Thus, 3-ATA appears to inhibit cyclin-dependent kinase activity by a mechanism distinct from that of the flavone L86827 and butyrolactone I, which are known to compete with ATP.

Identification of CDK4-specific inhibitors. To identify compounds in the NCI drug screen that may have a similar mechanism of action as 3-ATA, the pattern of growth inhibitory activity (GI$_{50}$) of 3-ATA with the GI$_{50}$ of all previously tested compounds as compared. Six compounds not previously examined for CDK4 kinase inhibitory activity had similar patterns of growth inhibitory activity with correlation coefficients greater than 0.6. Among these six, two benzothiadiazine (BTD) compounds (Compound 6) and NSC 645788) inhibited CDK4:cyclin D1 kinase activity in vitro with IC$_{50}$'s (5.0 and 17 µM, respectively) similar to the IC$_{50}$ of 3-ATA (6.8 µM).

An additional 45 compounds with structural similarity to 3-ATA and (Compound 6) were available for analysis. Nineteen of these compounds inhibited CDK4 kinase activity with IC$_{50}$'s ranging from 1.1 to more than 100 µM. Four compounds, 2 structurally related to 3-ATA (Compound 4) and NSC 645153), and 2, Compound 7 and Compound 8, were more potent CDK4 kinase inhibitors than the parent compounds. Compound 4, Compound 7, and Compound 8 also had no CDC2 or CDK2 kinase inhibitory activity at concentrations up to 100 µM. However, two of these compounds, Compound 4 and Compound 7, did not inhibit p16$^{INK4A}$ binding to CDK4, suggesting that their mechanism of inhibition of CDK4 kinase activity is distinct from 3-ATA.

Example 2

This example describes a method for treating cancer using the compounds of the invention. Thioacridones or benzothiadiazines satisfying Formulas 1 and 2 above are obtained that specifically inhibit CDK4:cyclin kinase such that these compounds have an IC$_{50}$ for CDK4 that is smaller than their IC$_{50}$ for CDC2 or CDK2. These compounds are administered intravenously or orally to humans at a dose of between 1 µg and 10 grams, preferable between 1 mg and 900 mg per m$^2$ of body surface of the patient. The compounds also can be mixed with at least one additive selected from the group consisting of carriers, diluents, excipients, diagnostics, direct compression buffers, buffers, stabilizers, fillers, disintegrates, flavors, colors, and mixtures thereof to form pharmaceutical compositions. The compositions are administered intravenously or orally to humans at a dose of between 1 µg and 10 grams, preferable between 1 mg and 900 mg per m$^2$ of body surface of the patient.

Cell Line Data

Figure 2A:
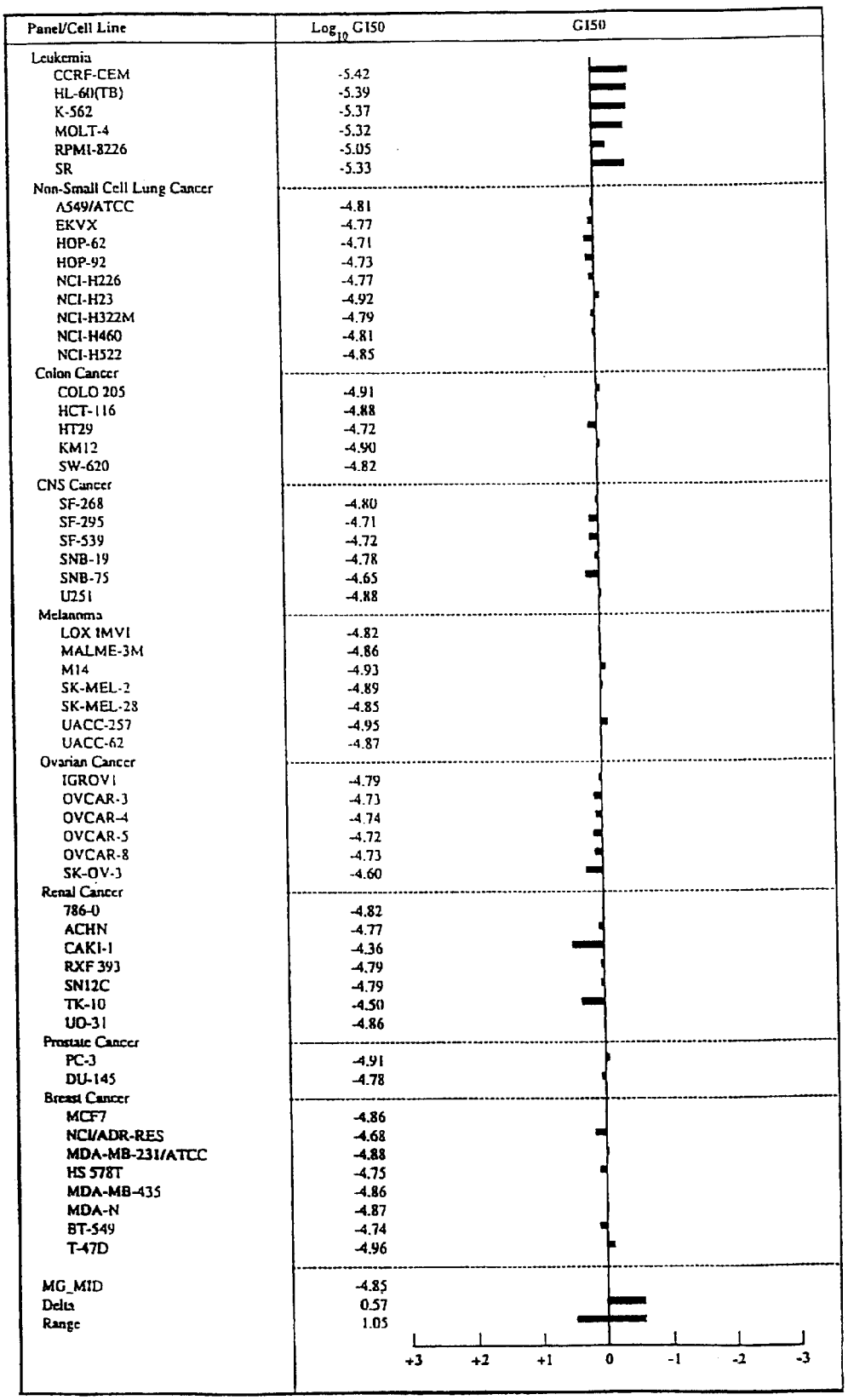
FIGS. 2(A)–2(C) shows mean plots of data from FIGS. 1A–1I, wherein the left-hand mean plot is of $GI_{50}$ data, the middle mean plot is of TGI data, and the right-hand mean plot is of $LC_{50}$ data.
Figure 2B:
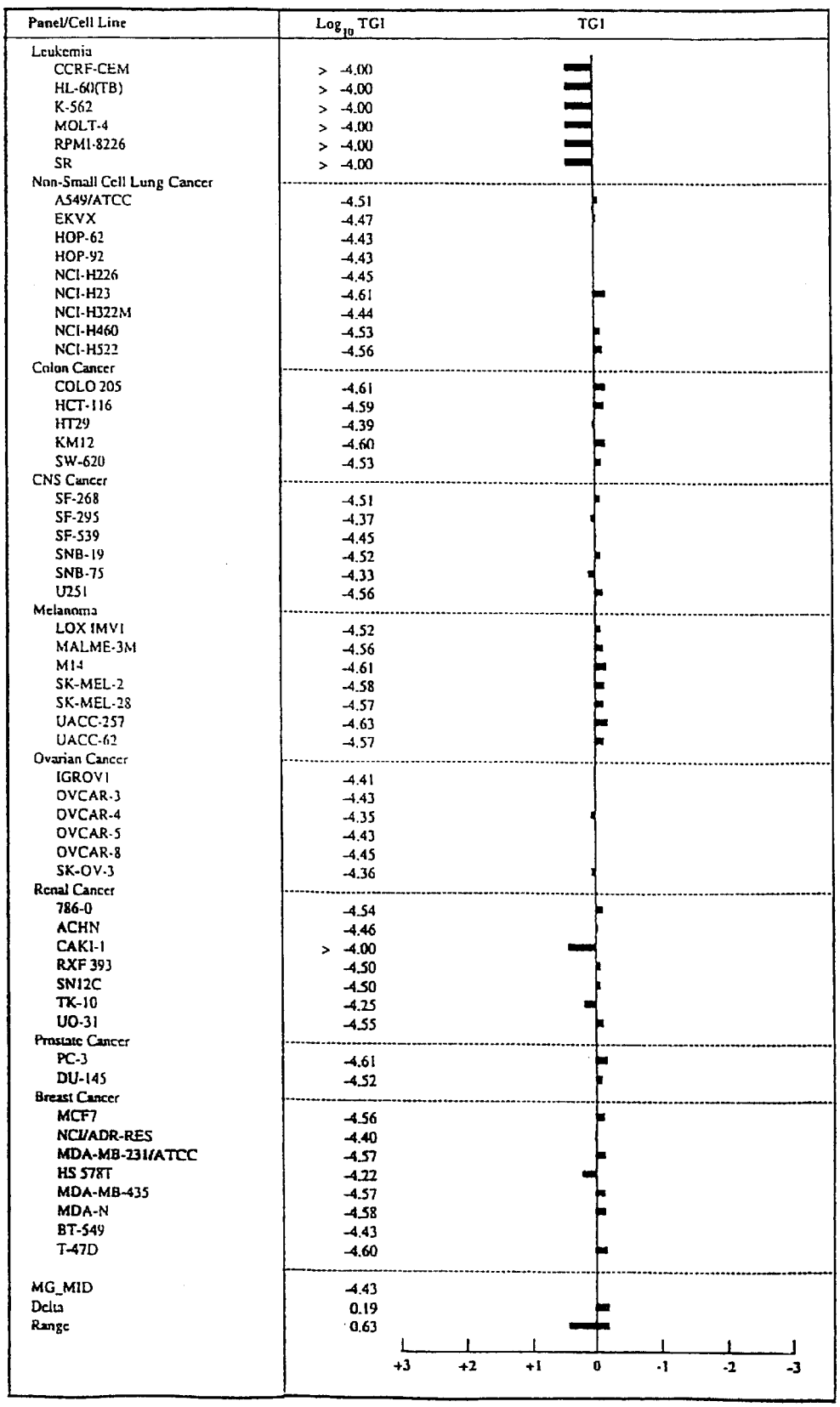
Figure 2C:
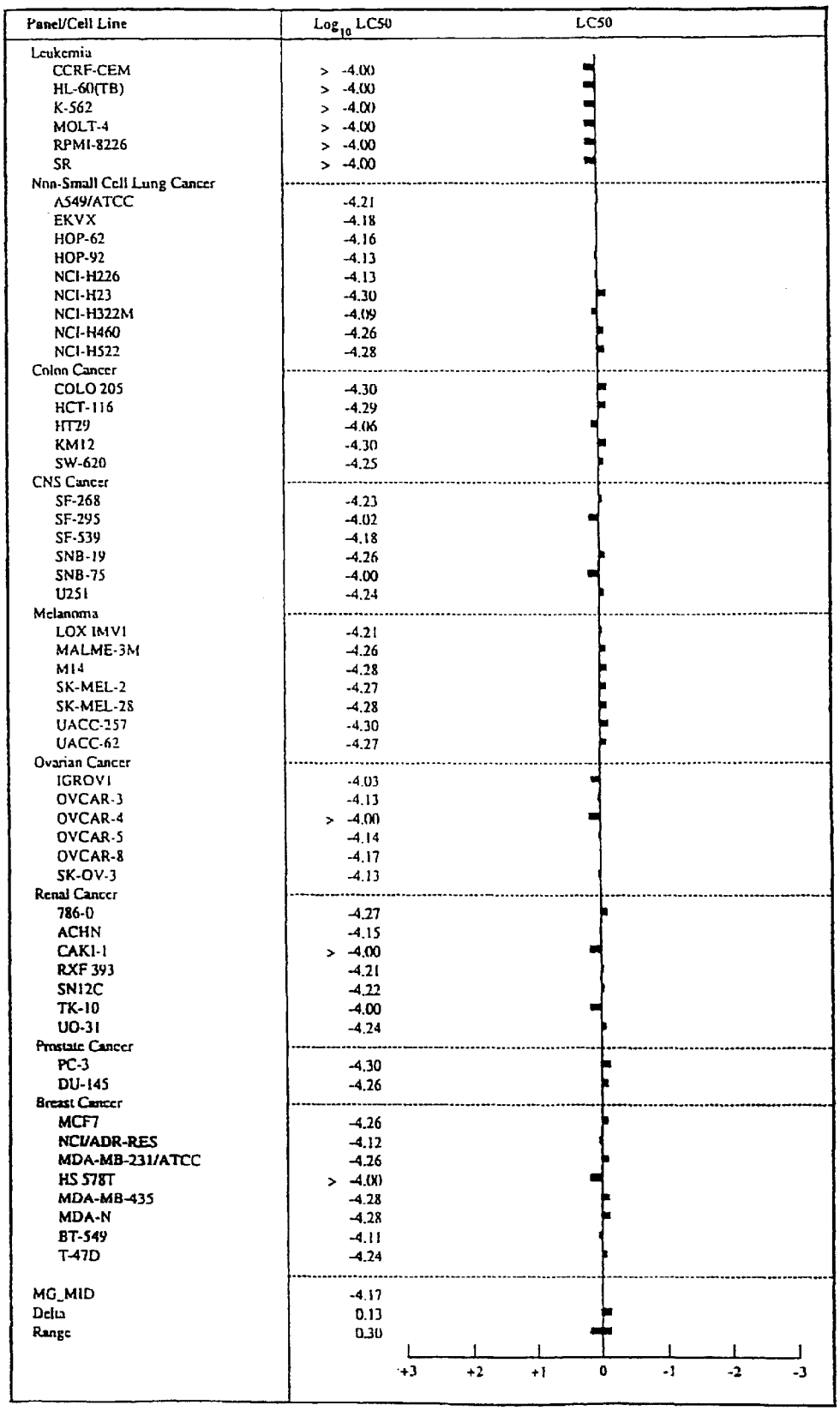
Figure 3:
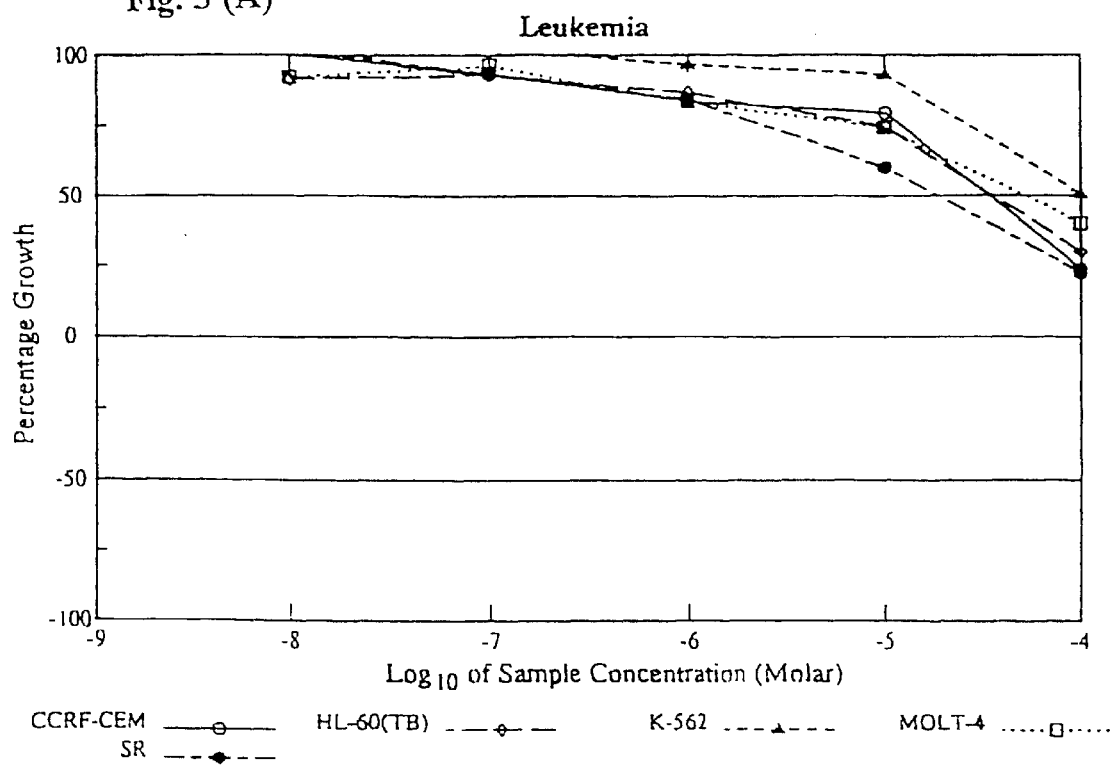
FIGS. 3(A)–3(I) are dose-response curves showing the effect of Compound 7 on various cancer cell lines in culture.
Figure 3:
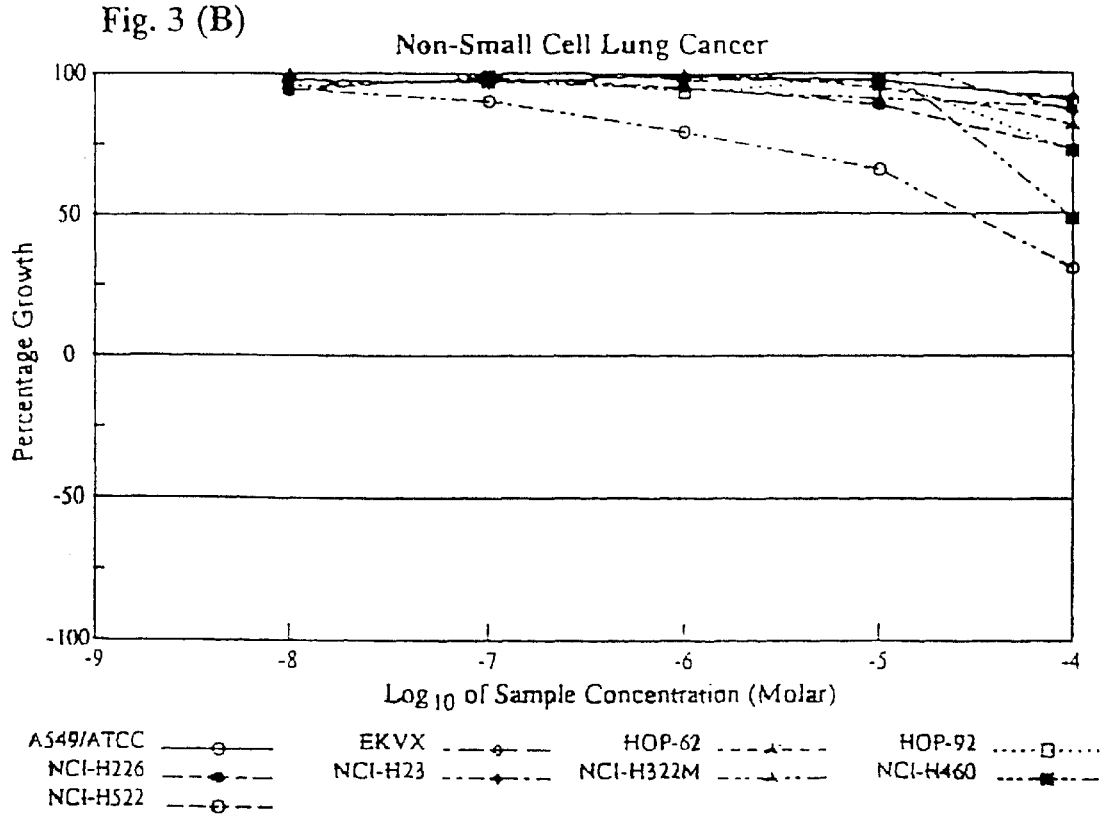
Figure 3:
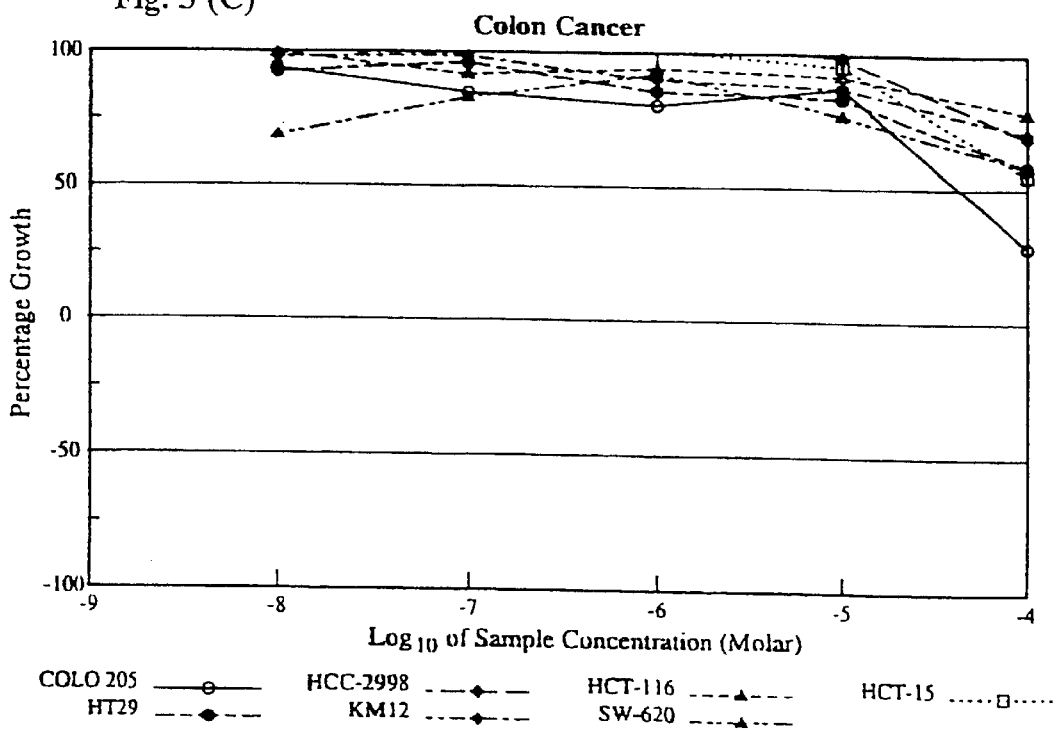
Figure 3:
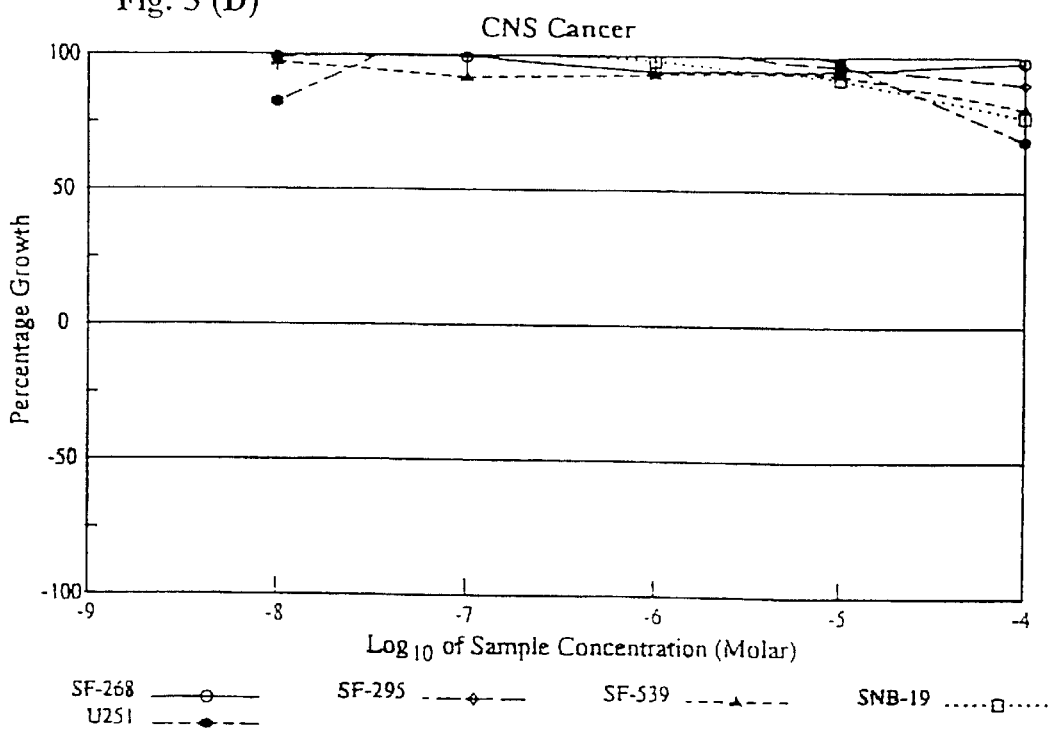
Figure 3:
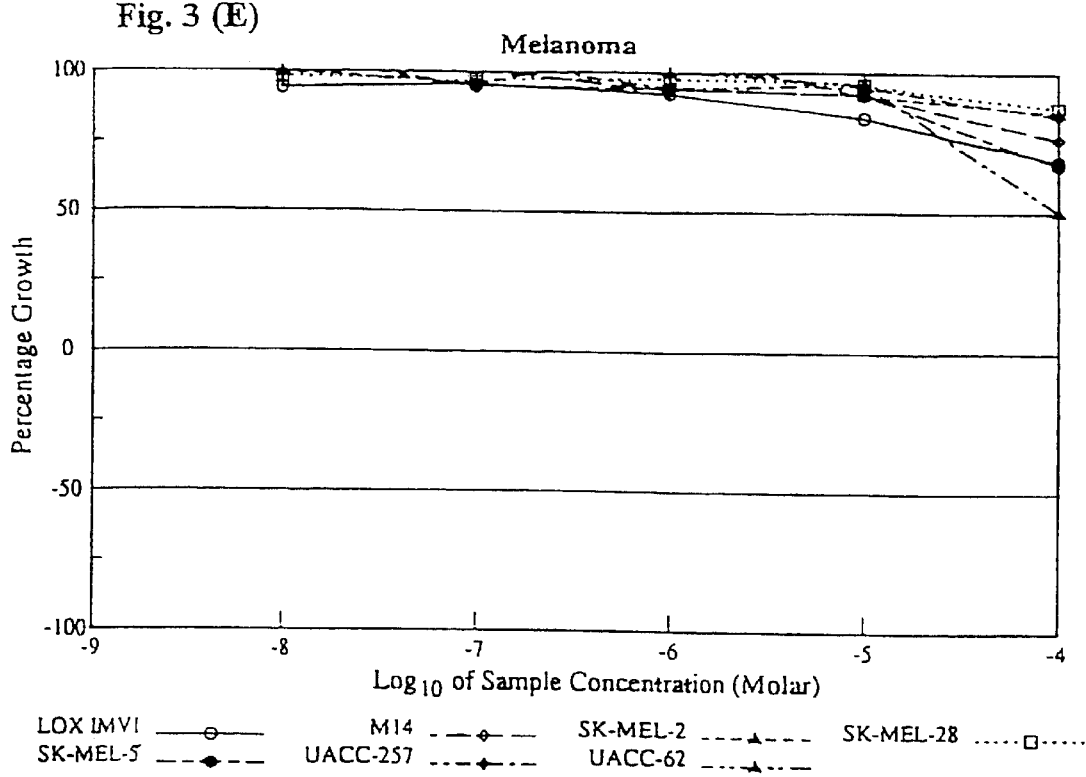
Figure 3:
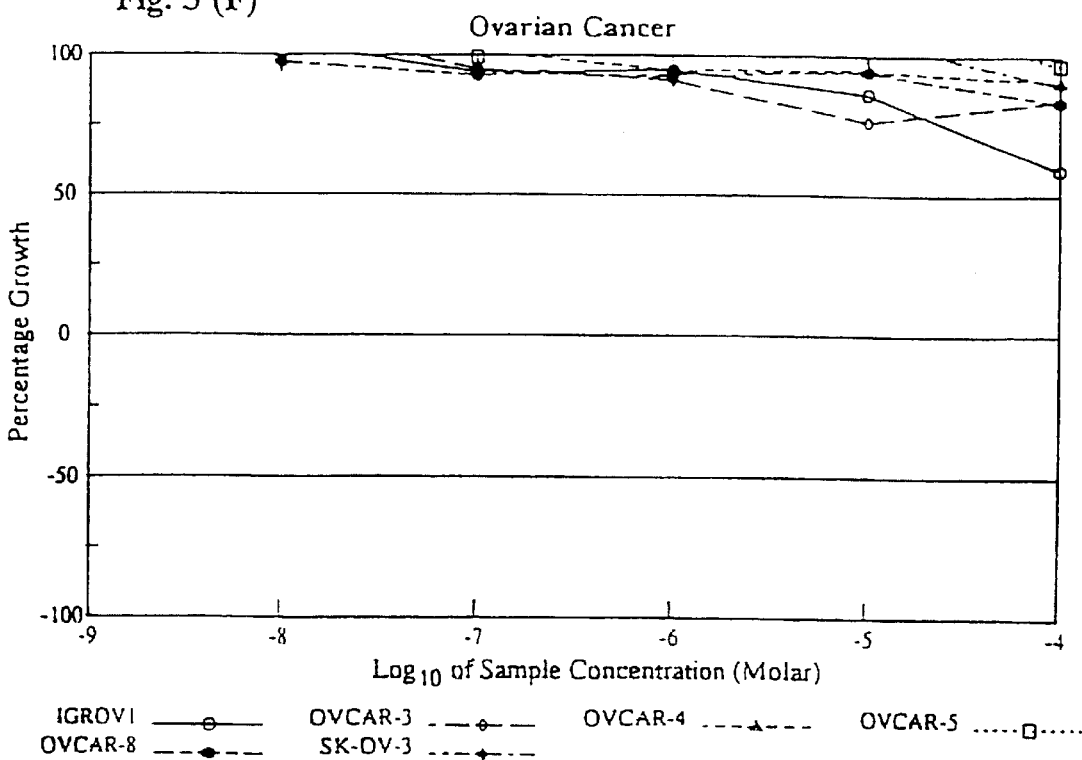
Figure 3:
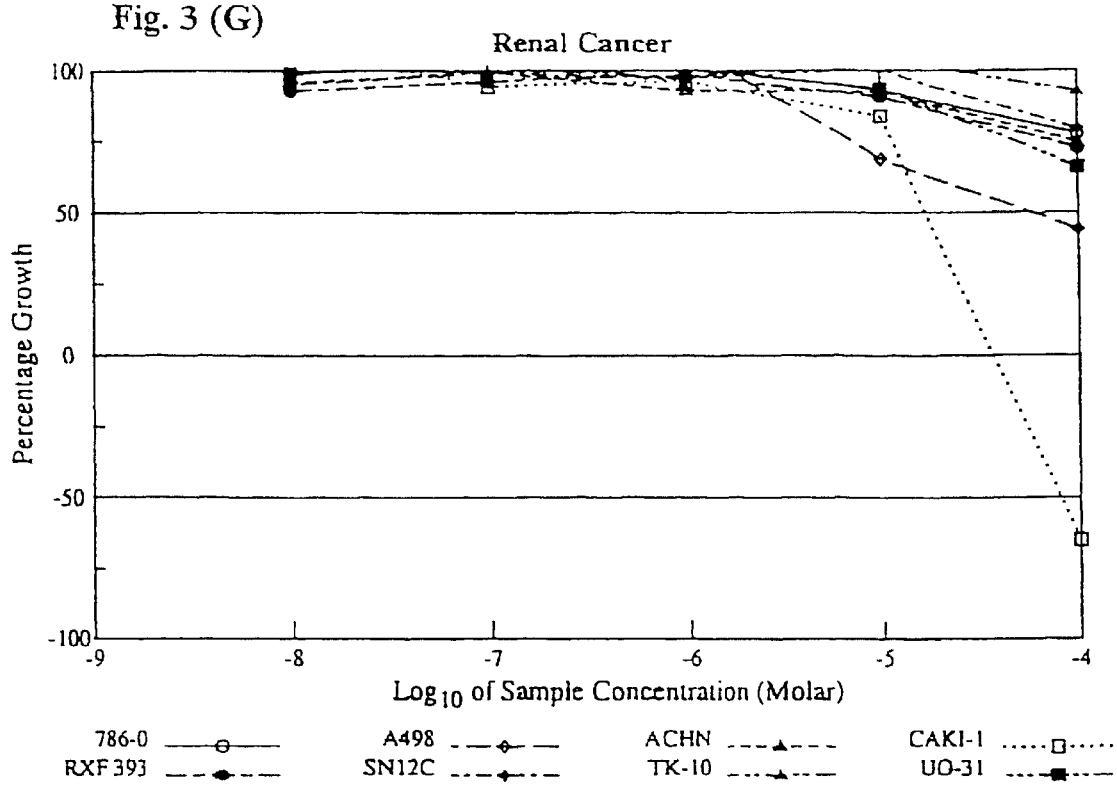
Figure 3:
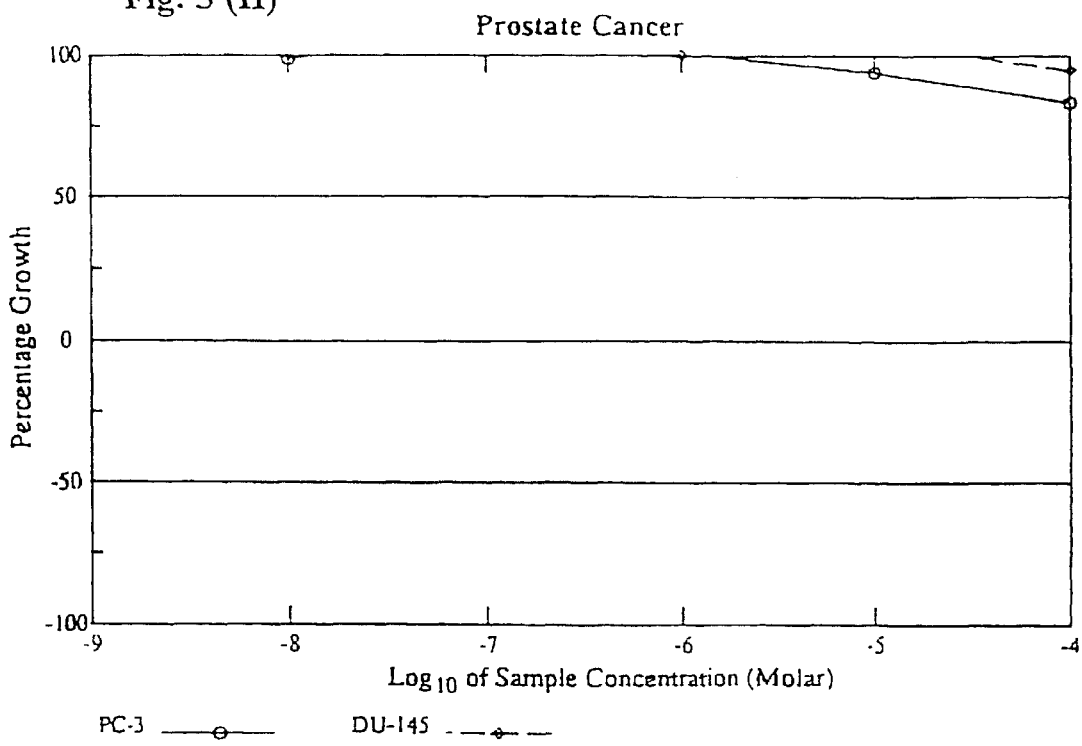
Figure 4A:
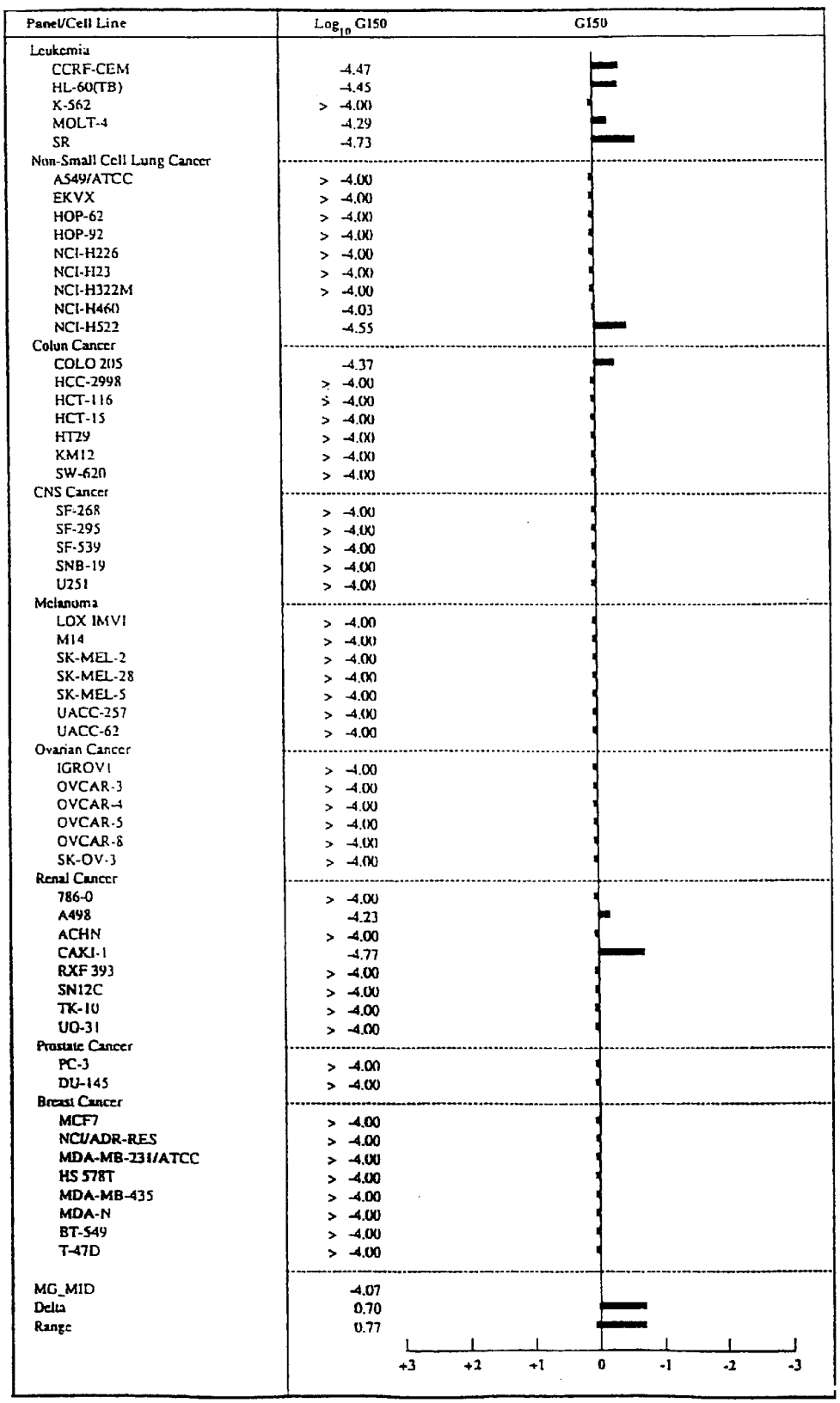
Figure 4B:
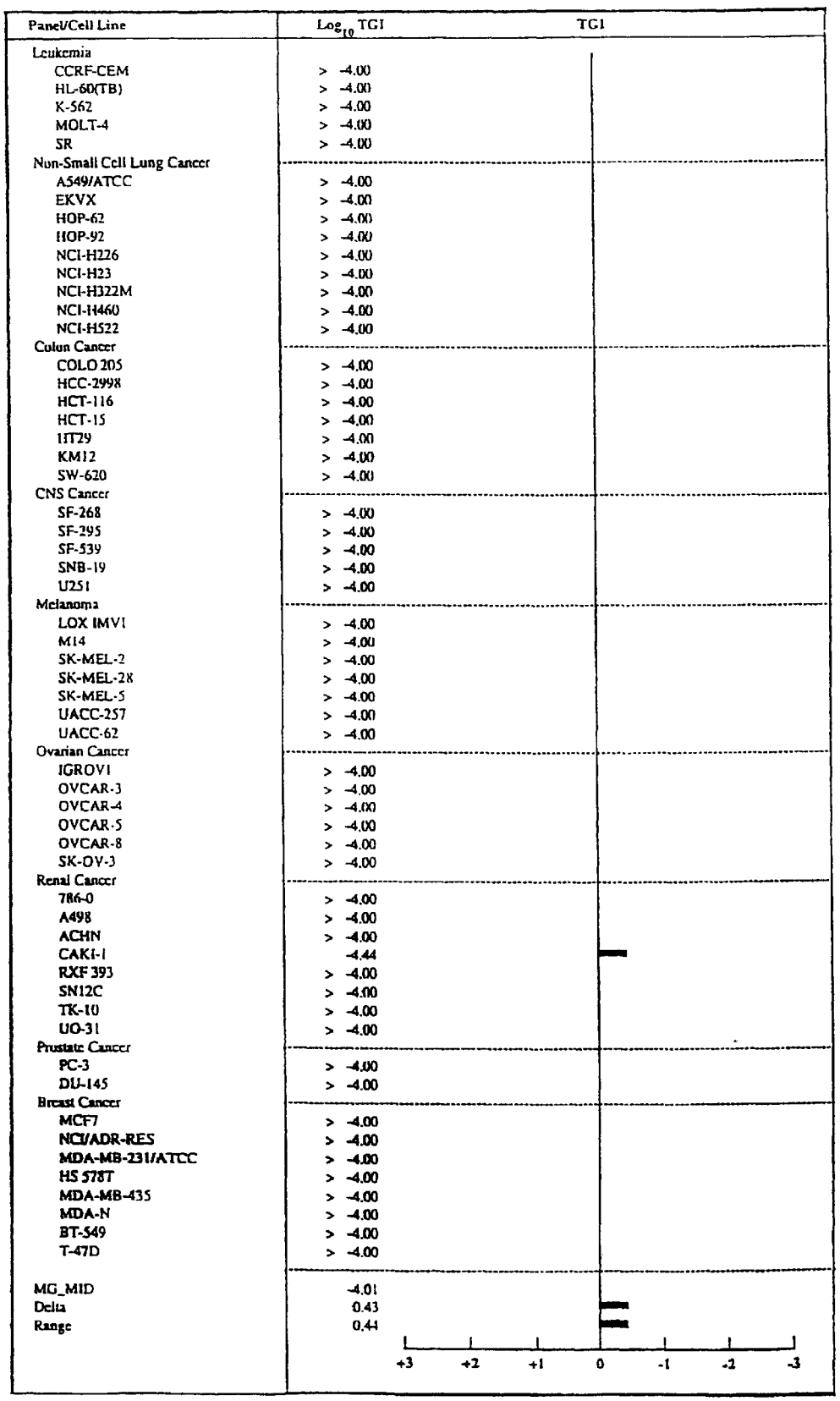
Figure 5:
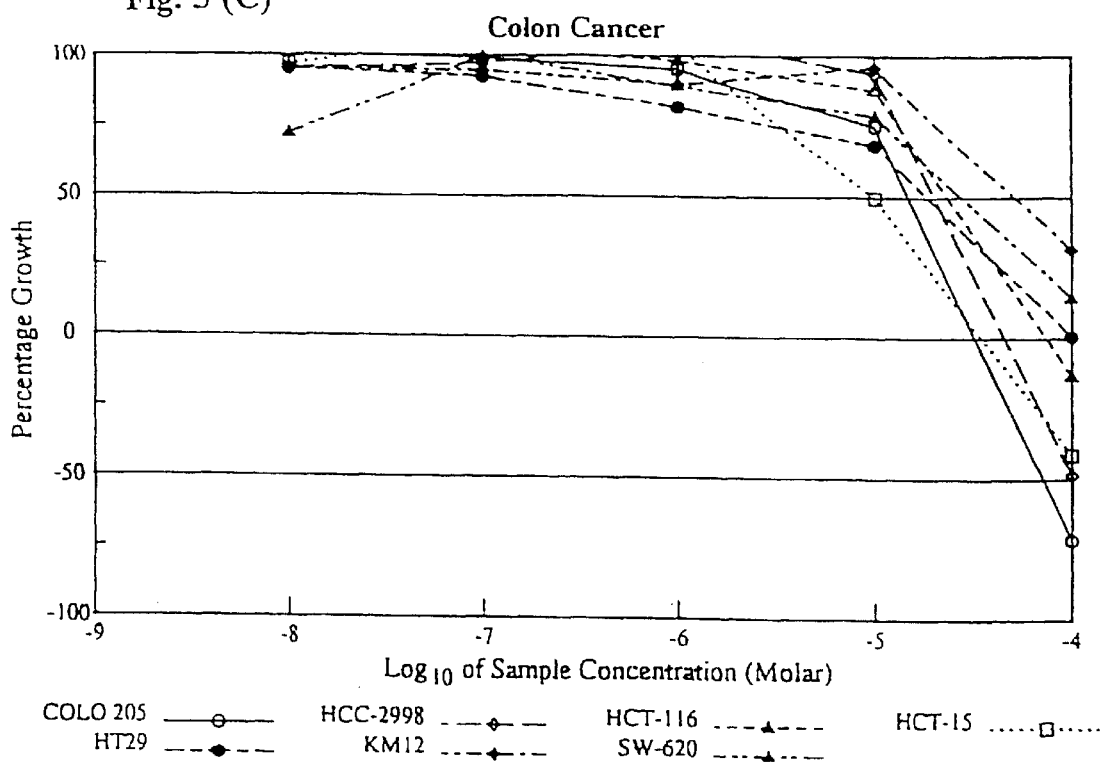
FIGS. 5(A)–5(I) are dose-response curves showing the effect of Compound 8 on various cancer cell lines in culture.
Figure 5:
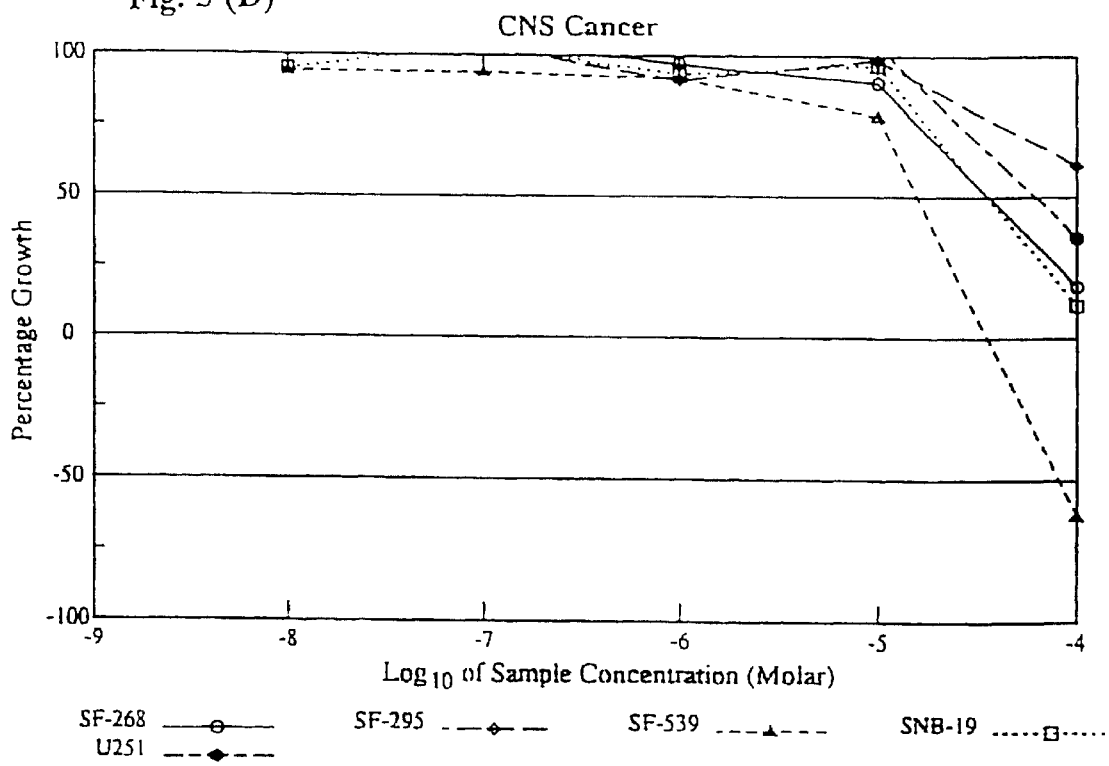
Figure 5:
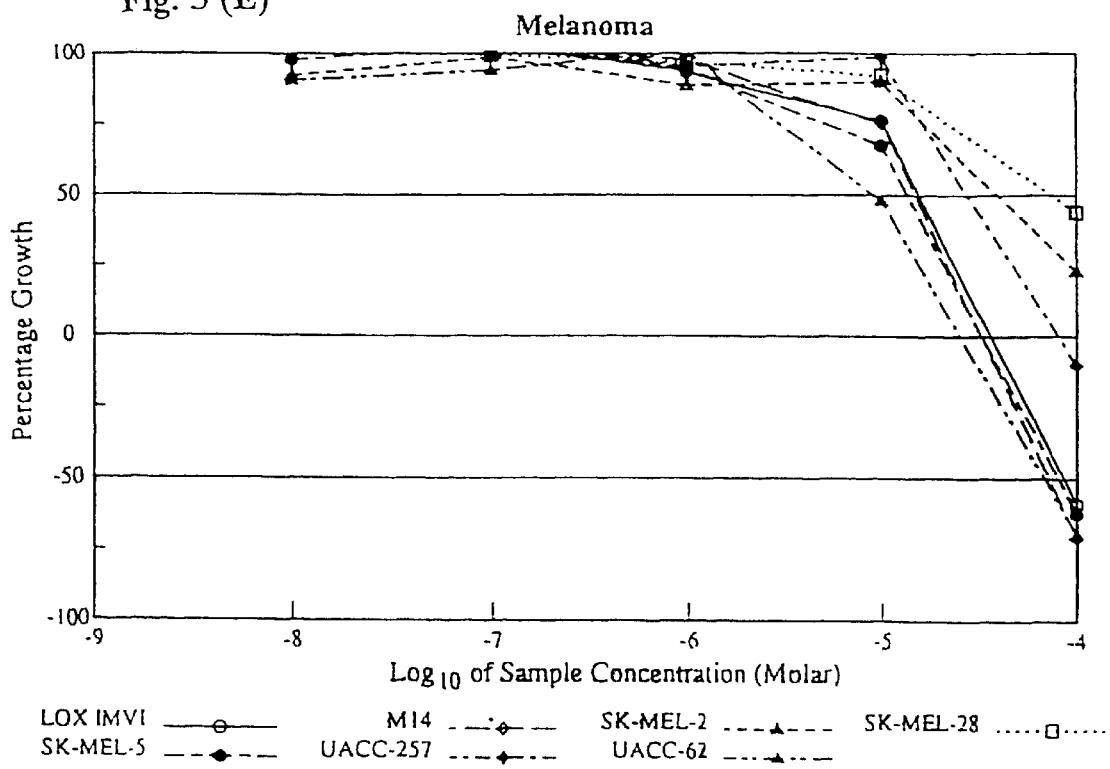
Figure 5:
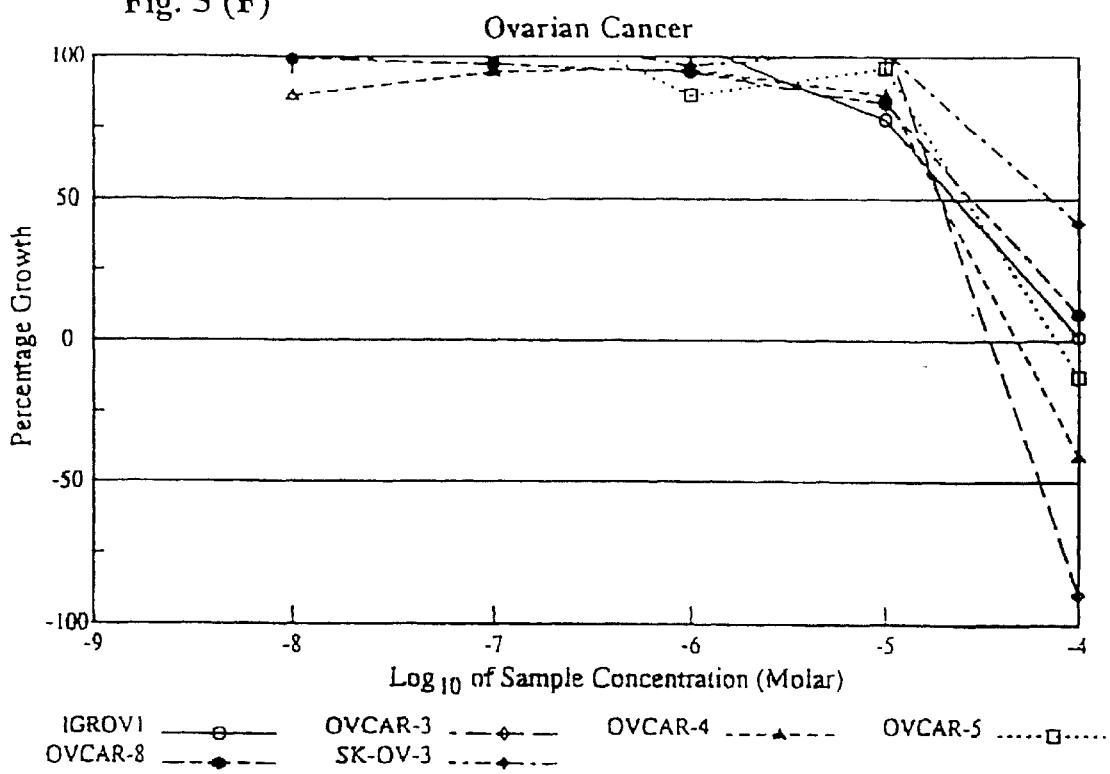
Figure 5:
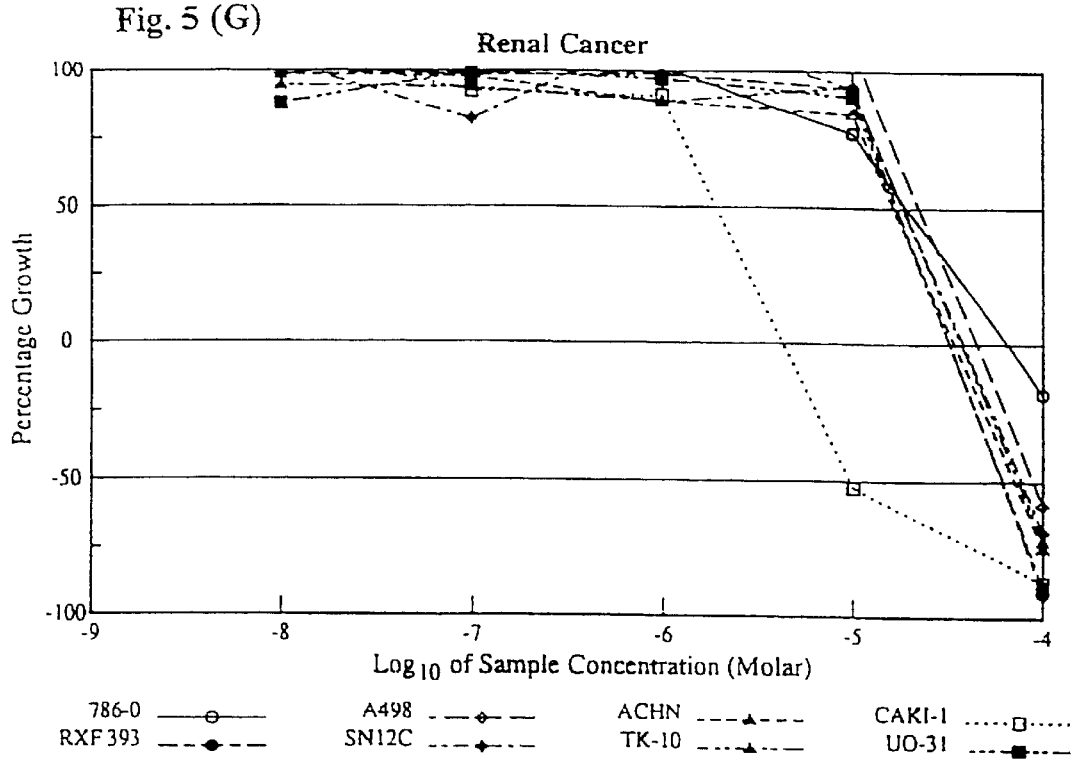
Figure 5:
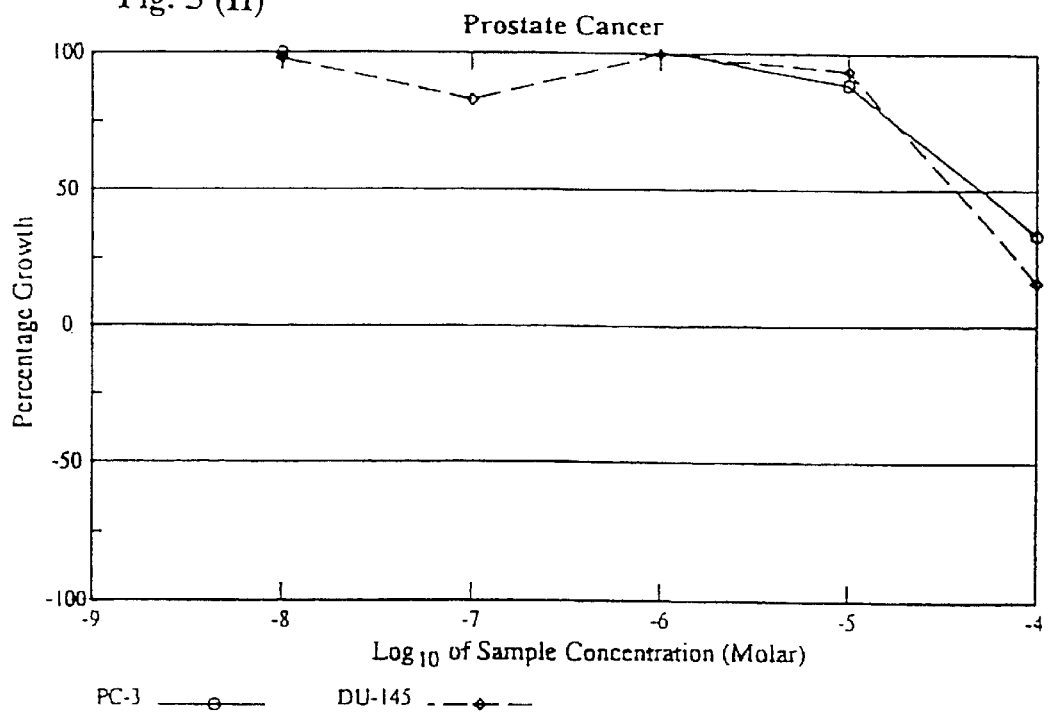
Figure 6A:
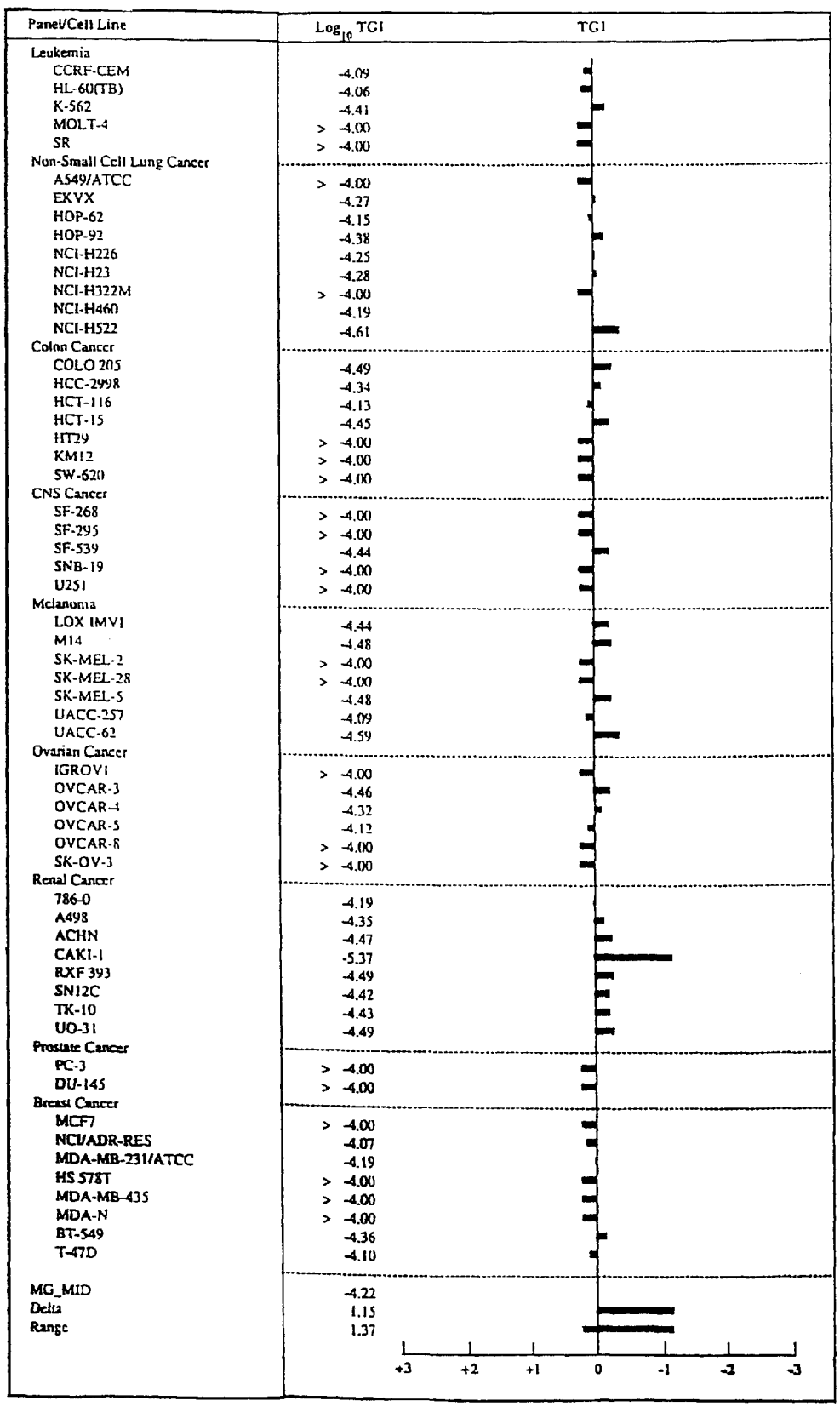
FIGS. 6(A)–6(C) shows mean plots of data from FIGS. 5A–5I, wherein the left-hand mean plot is of $GI_{50}$ data, the middle mean plot is of TGI data, and the right-hand mean plot is of $LC_{50}$ data.
Figure 6B:
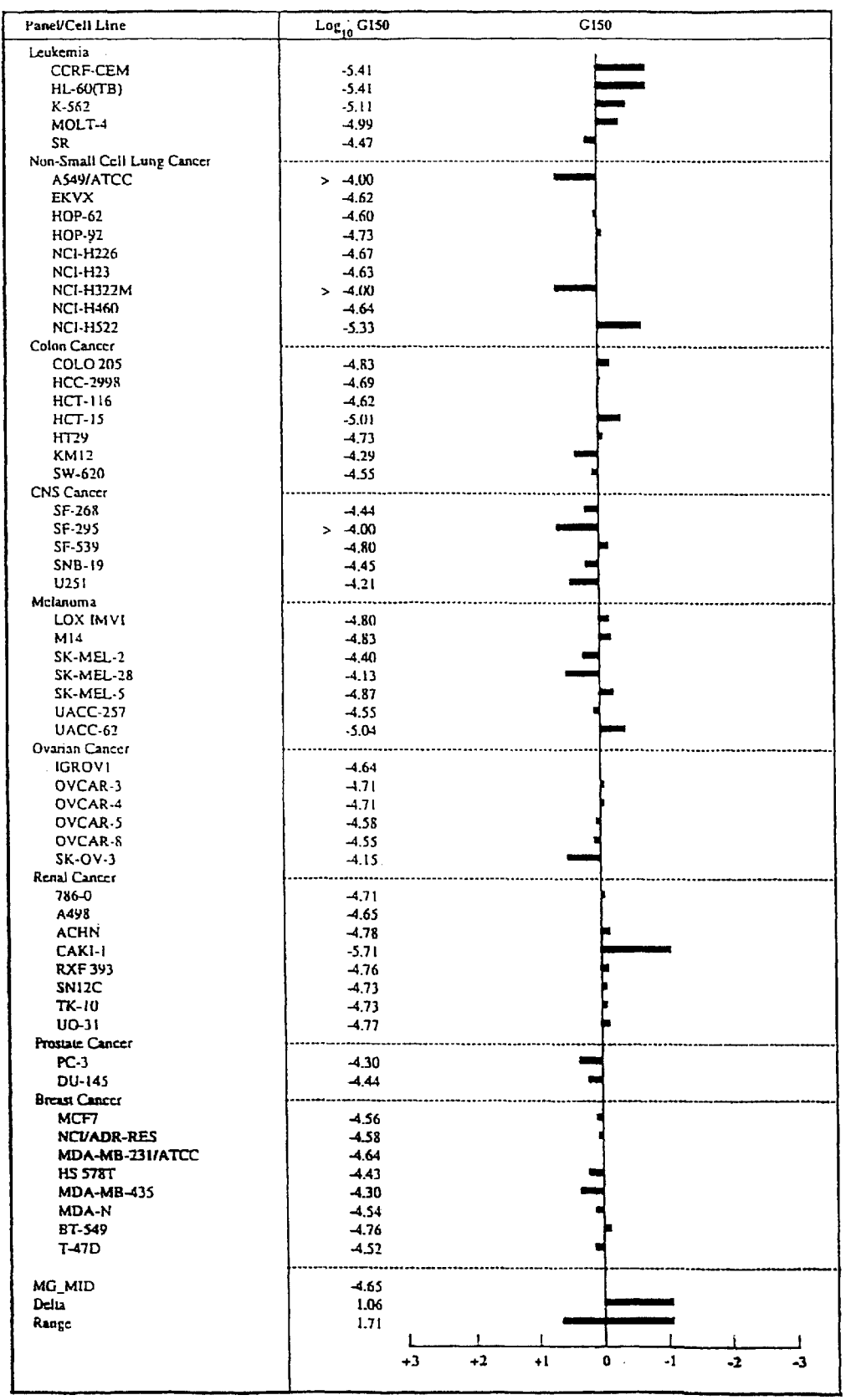
Figure 6C:
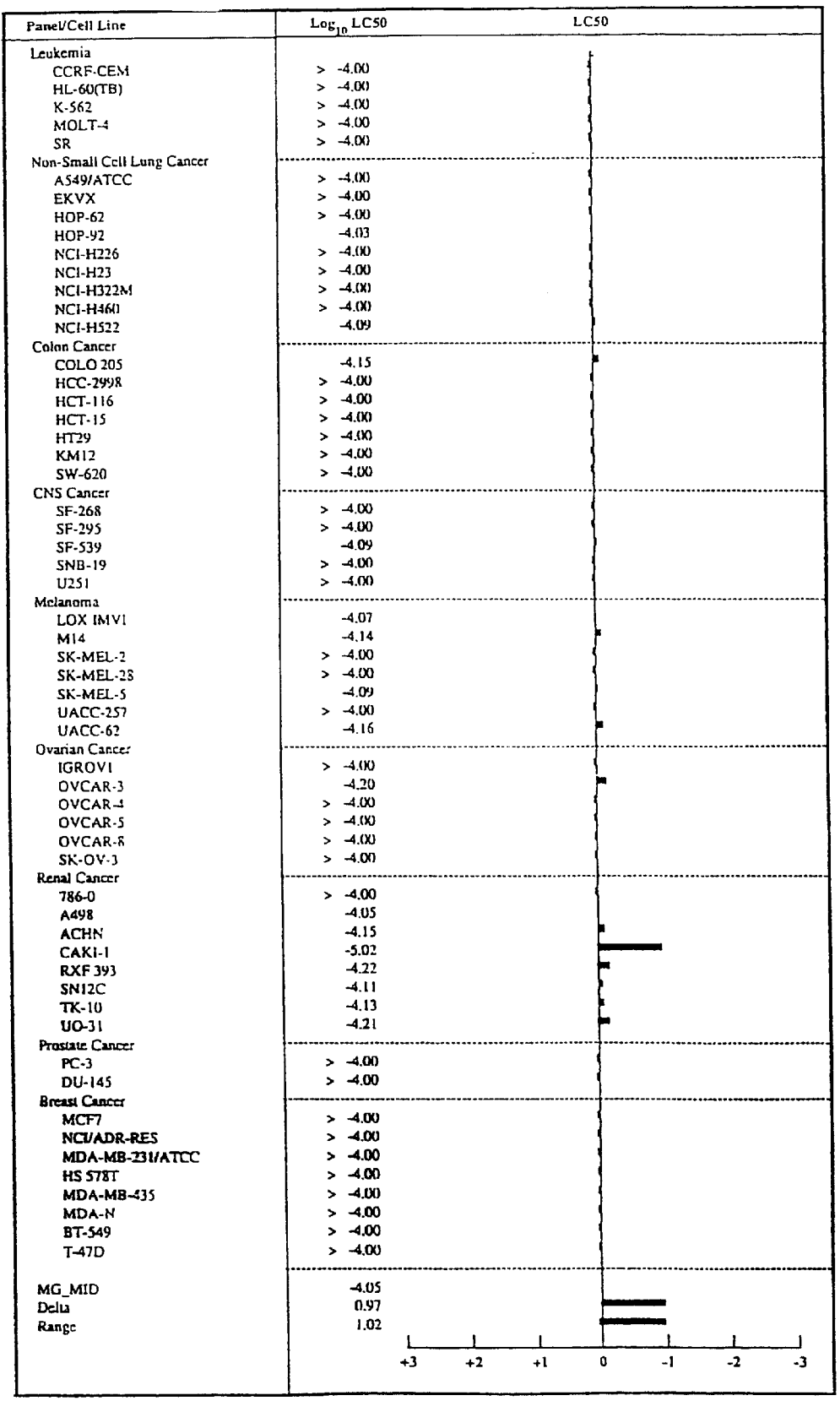
Figure 7:
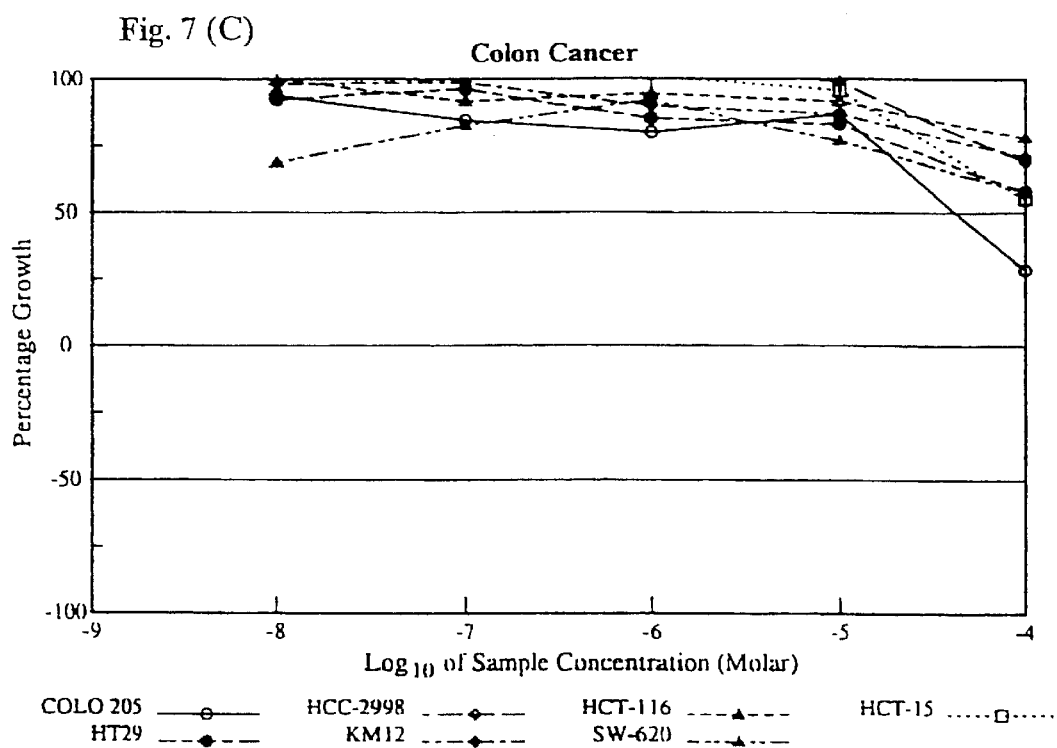
FIGS. 7(A)–7(I) are dose-response curves showing the effect of Compound 4 on various cancer cell lines in culture.
Figure 7:
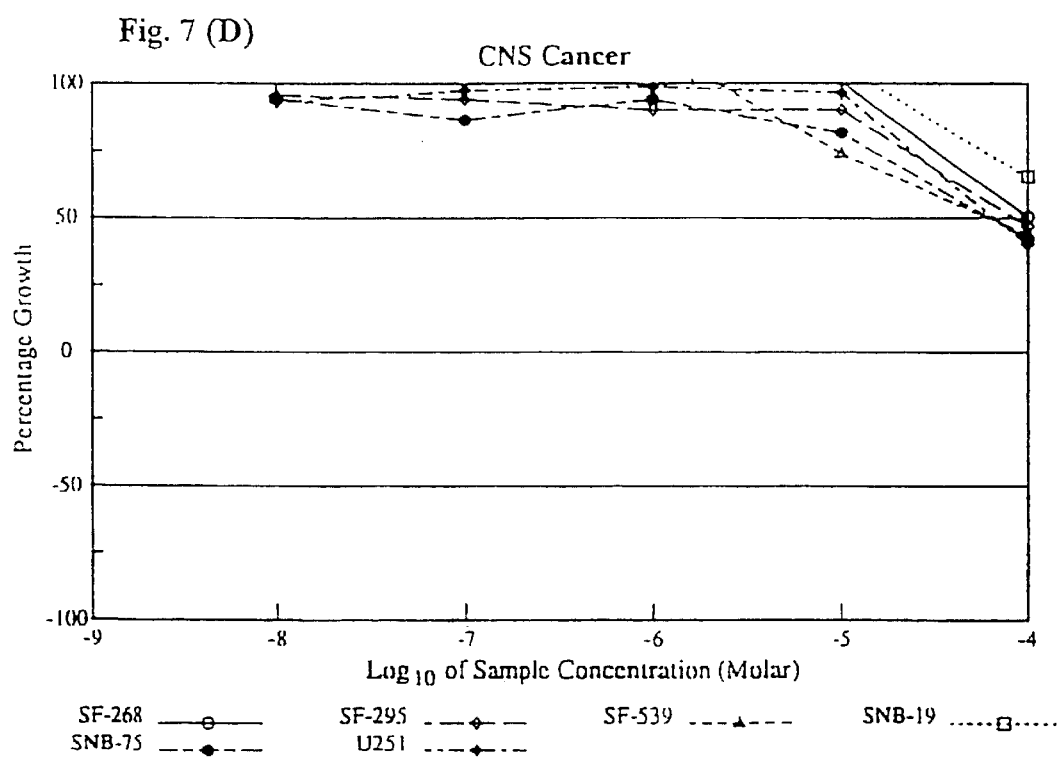
Figure 8A:
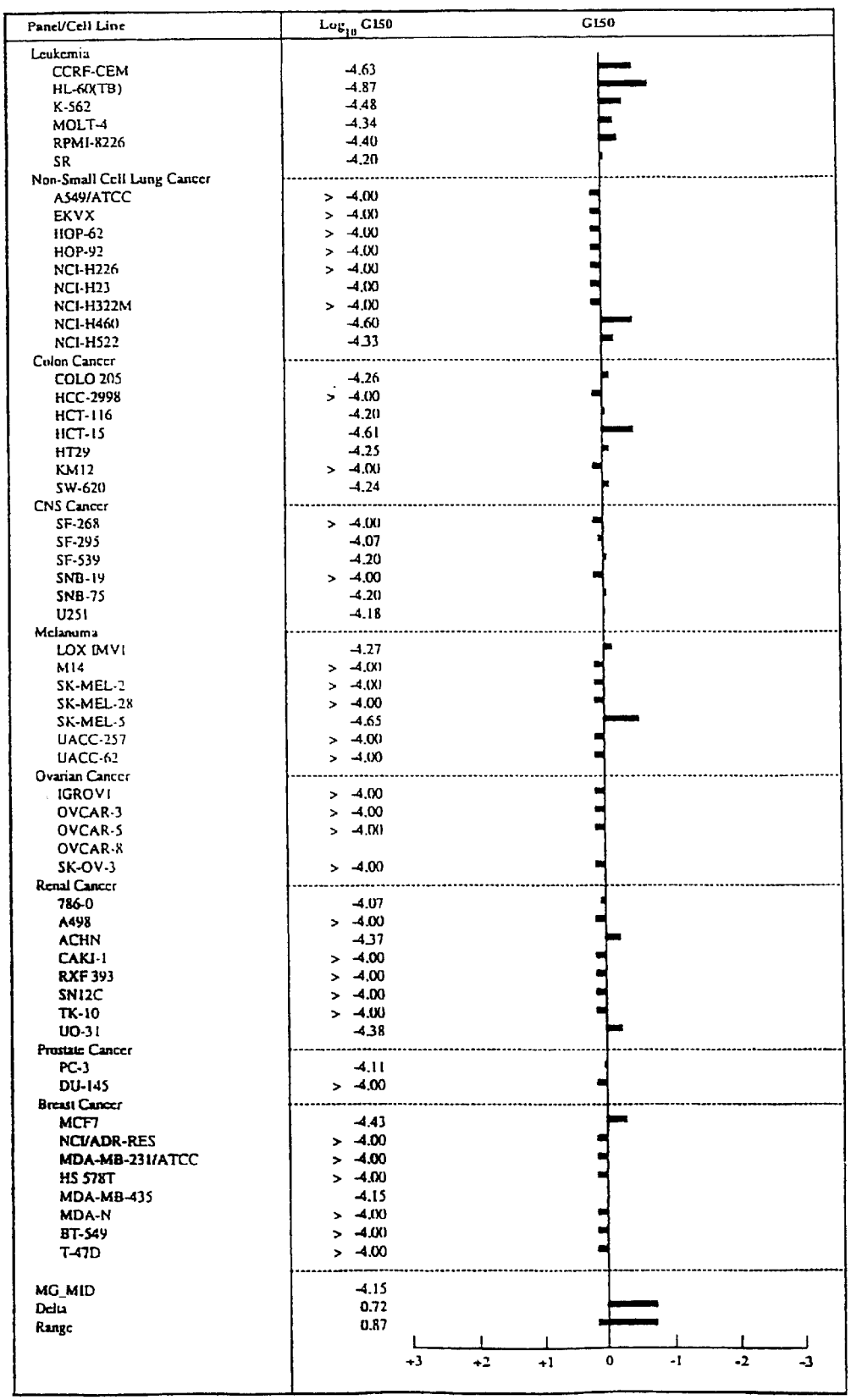
Figure 8B:
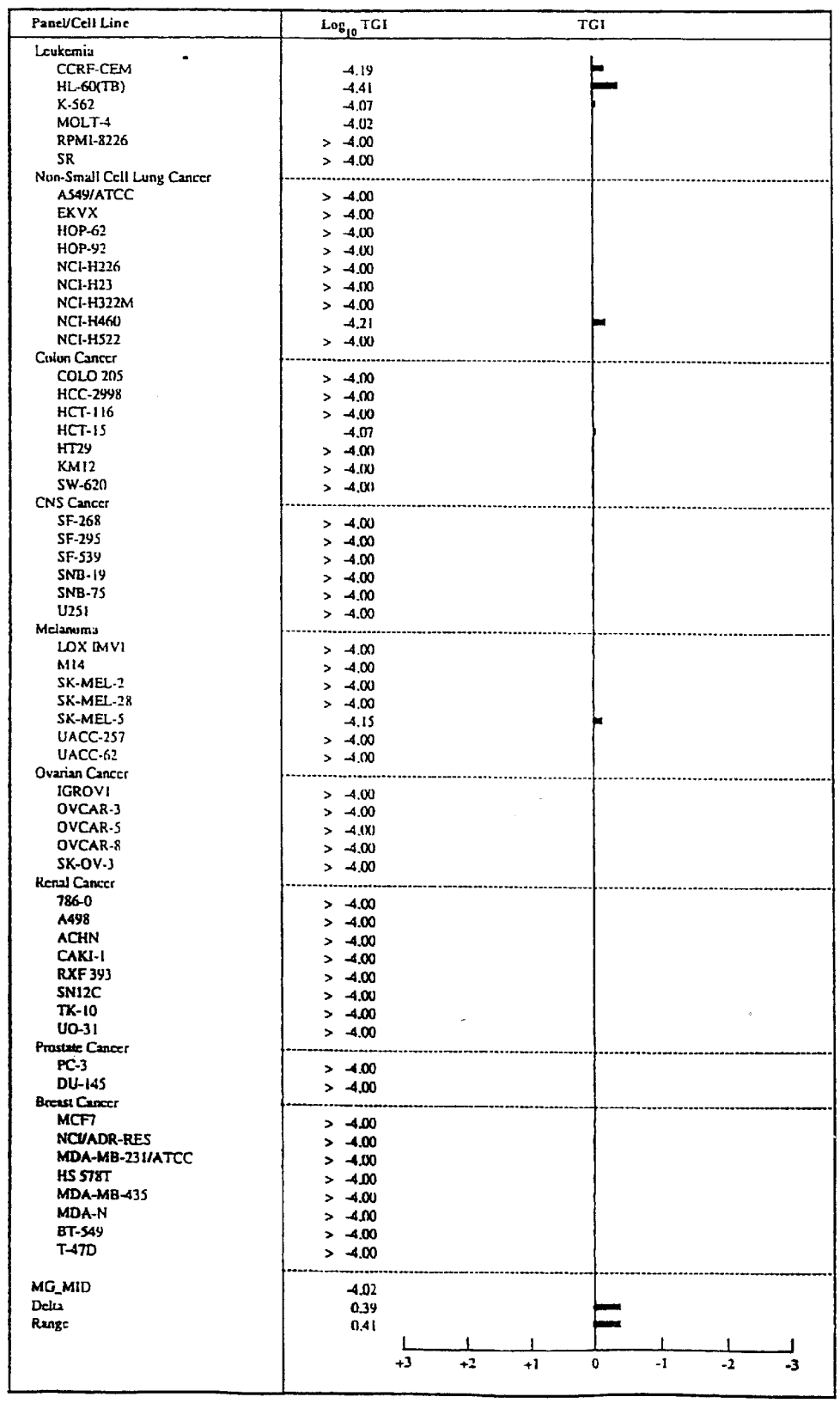
Figure 9:
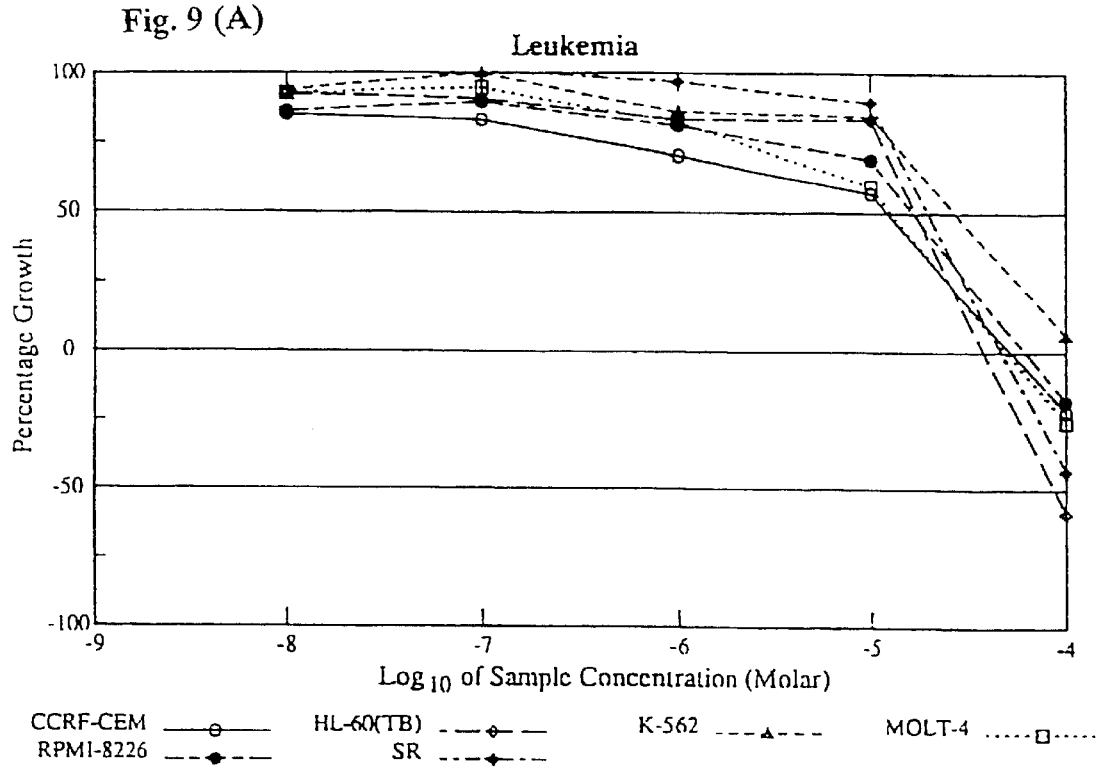
FIGS. 9(A)–9(I) are dose-response curves showing the effect of Compound 6 on various cancer cell lines in culture.
Figure 9:
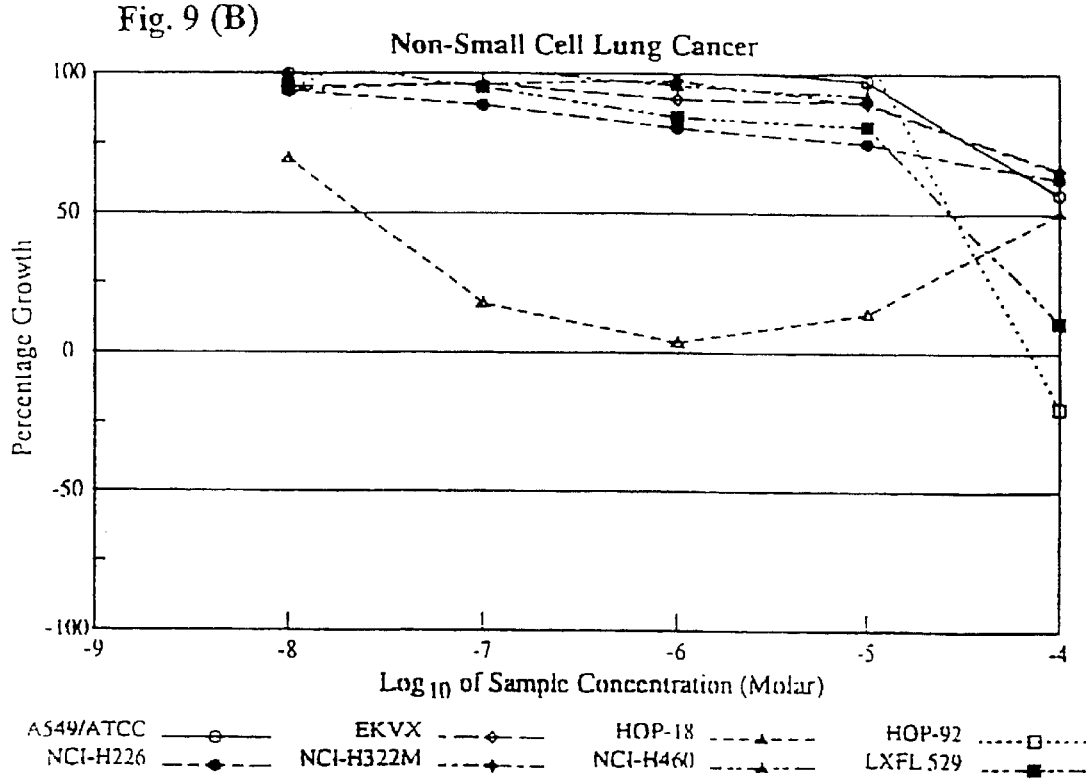
Figure 9:
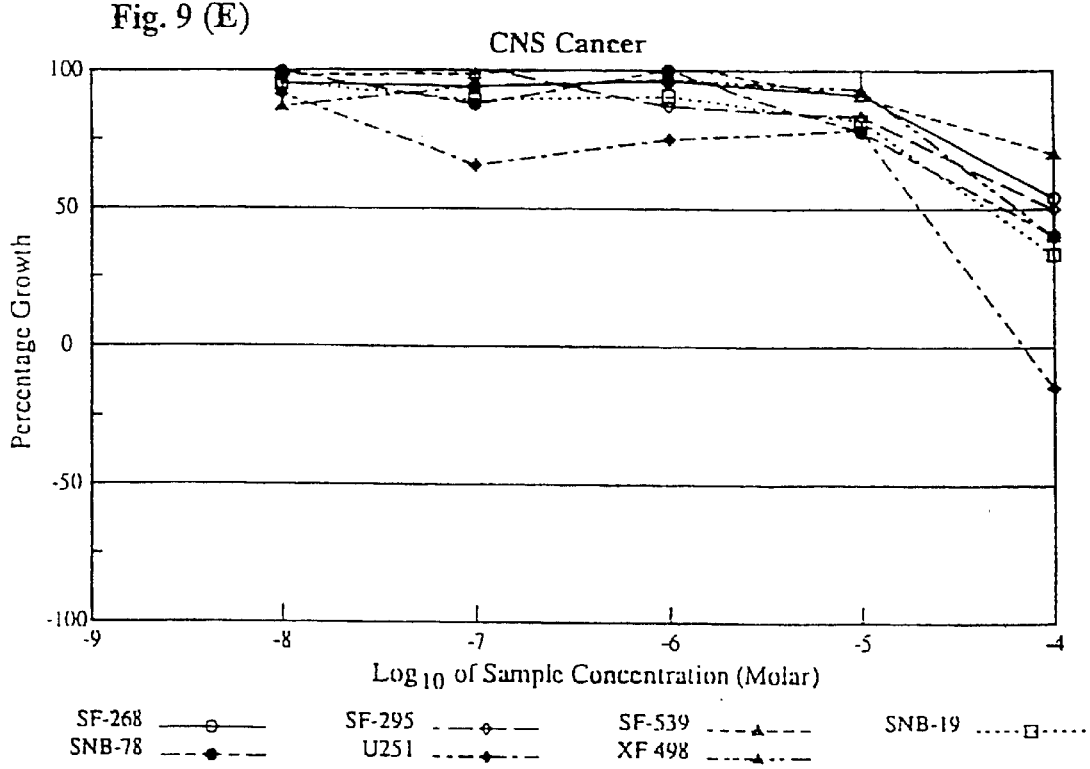
Figure 9:
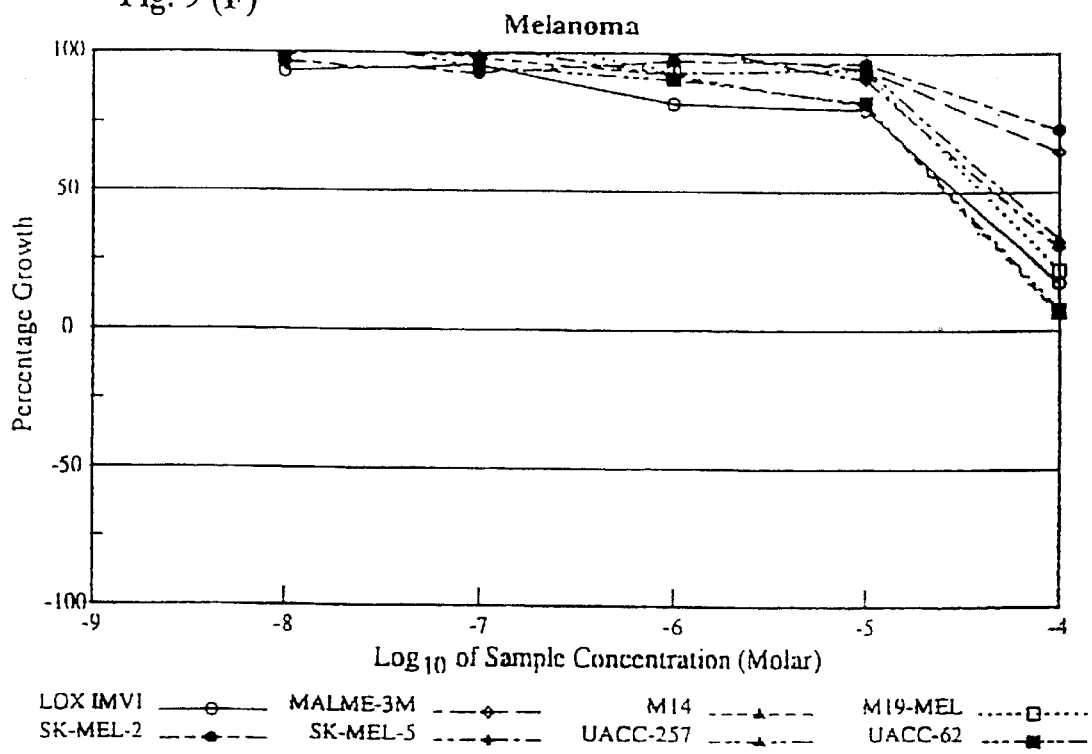
Figure 10A:
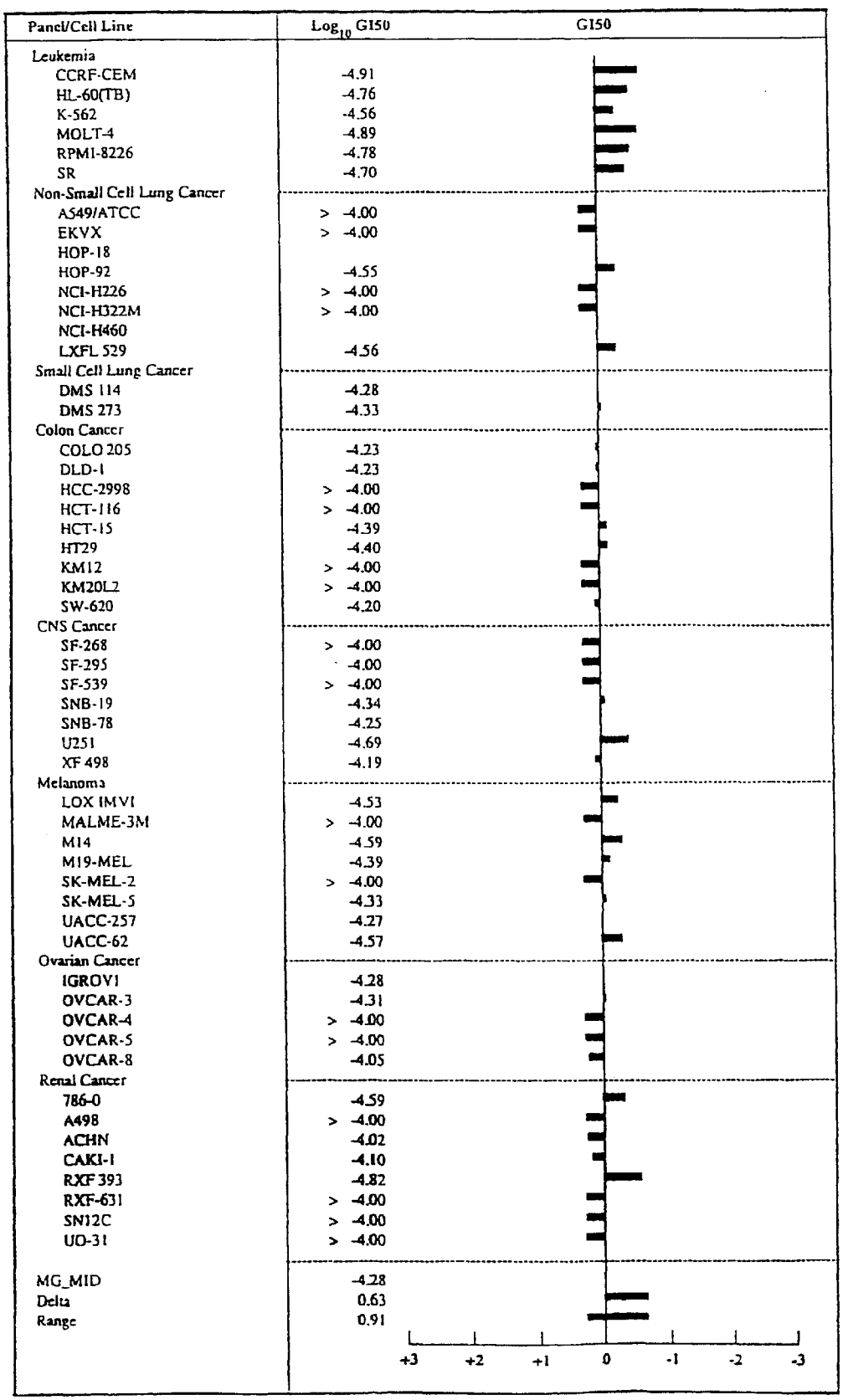
FIGS. 10(A)–10(C) shows mean plots of data from FIGS. 9A–9I, wherein the left-hand mean plot is of $GI_{50}$ data, the middle mean plot is of TGI data, and the right-hand mean plot is of $LC_{50}$ data.
Figure 10B:
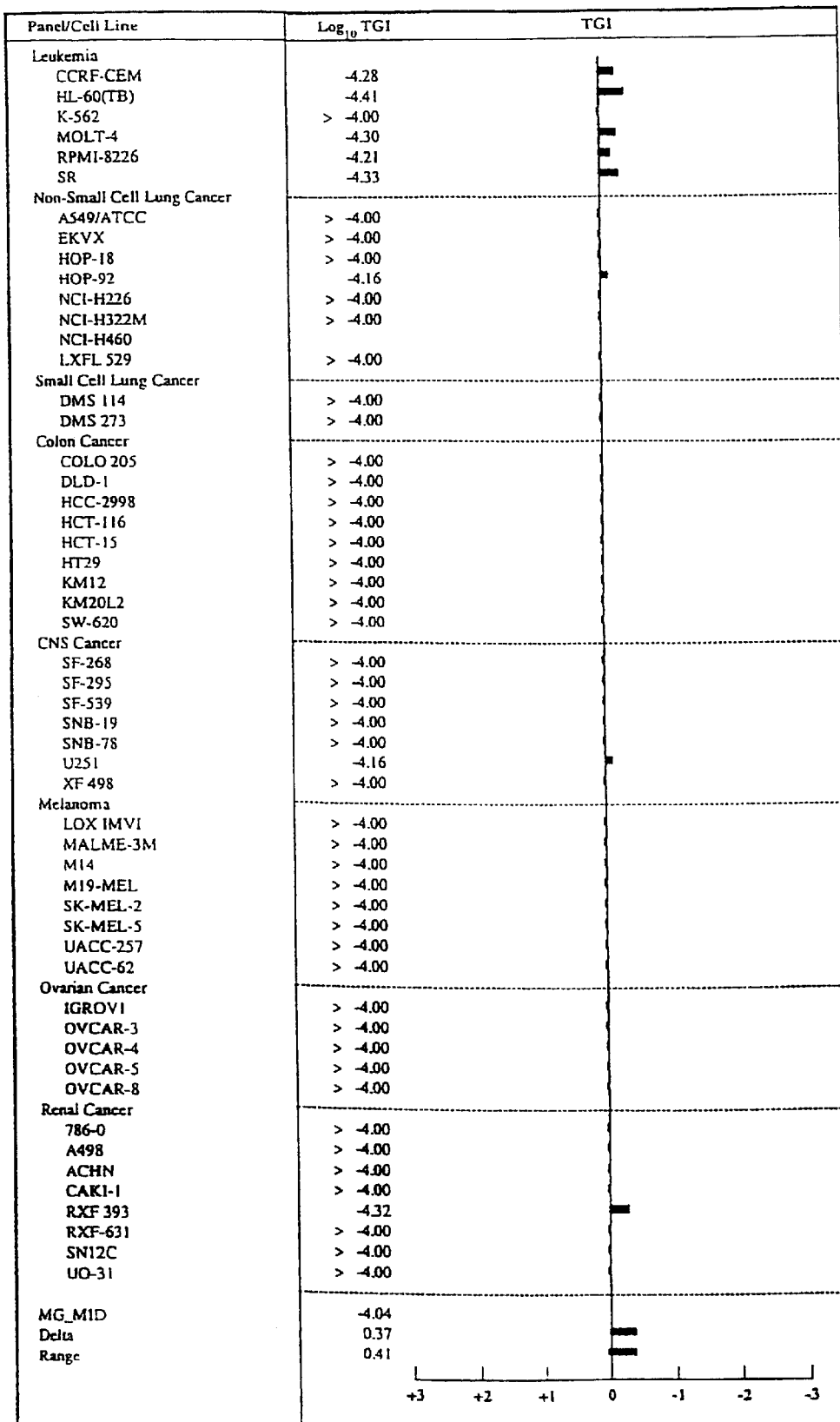
Figure 10C:
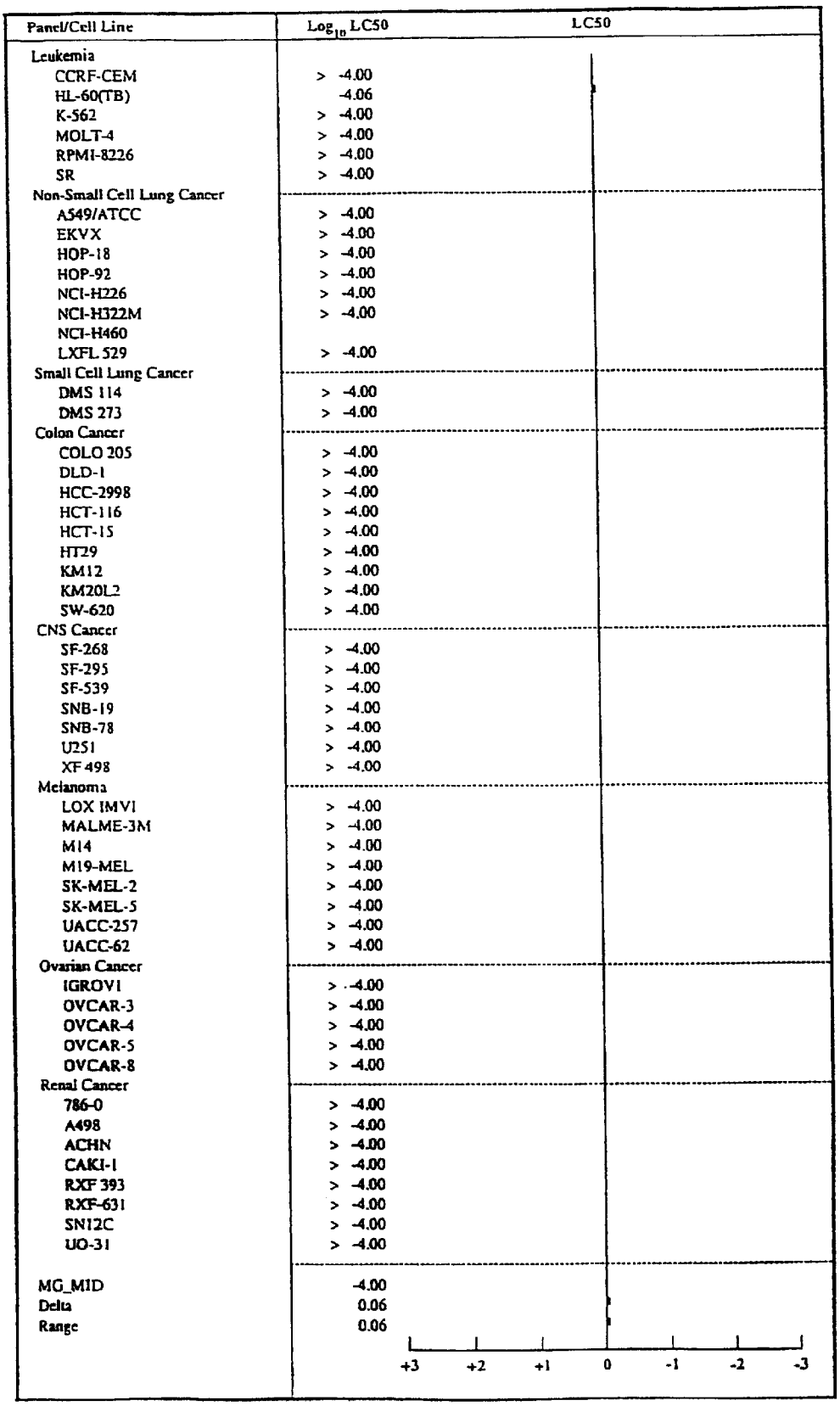
Figure 11:
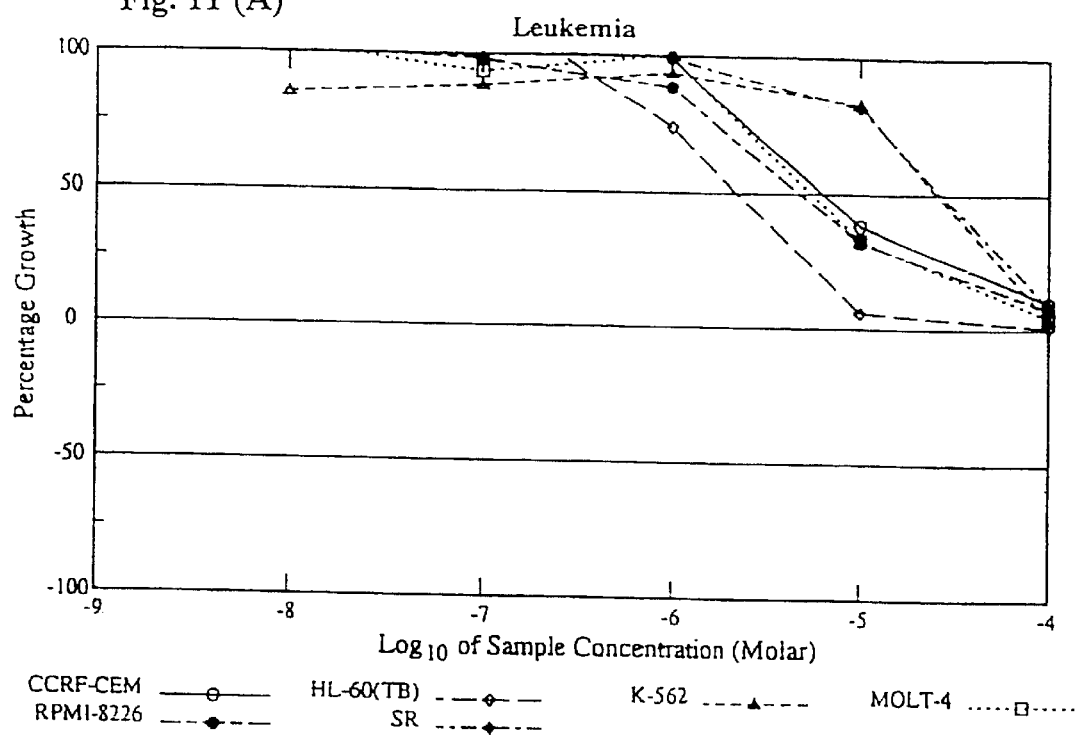
FIGS. 11(A)–11(I) are dose-response curves showing the effect of Compound 3 on various cancer cell lines in culture.
Figure 11:
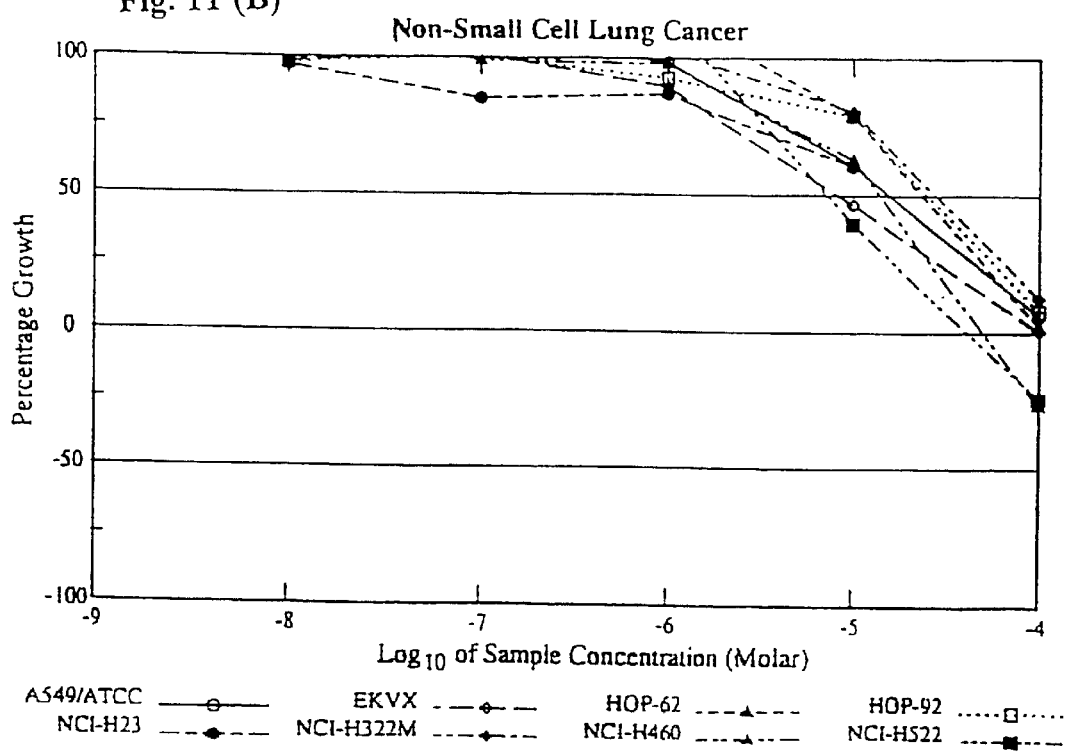
Figure 11:
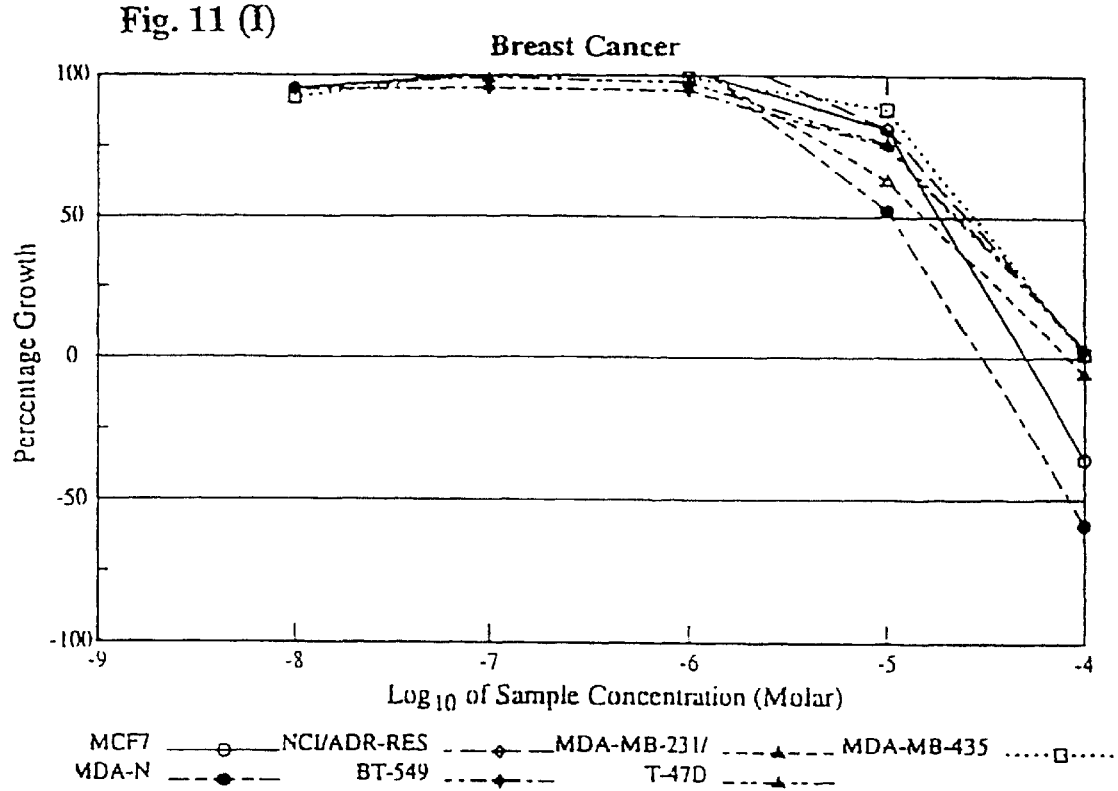
Figure 12A:
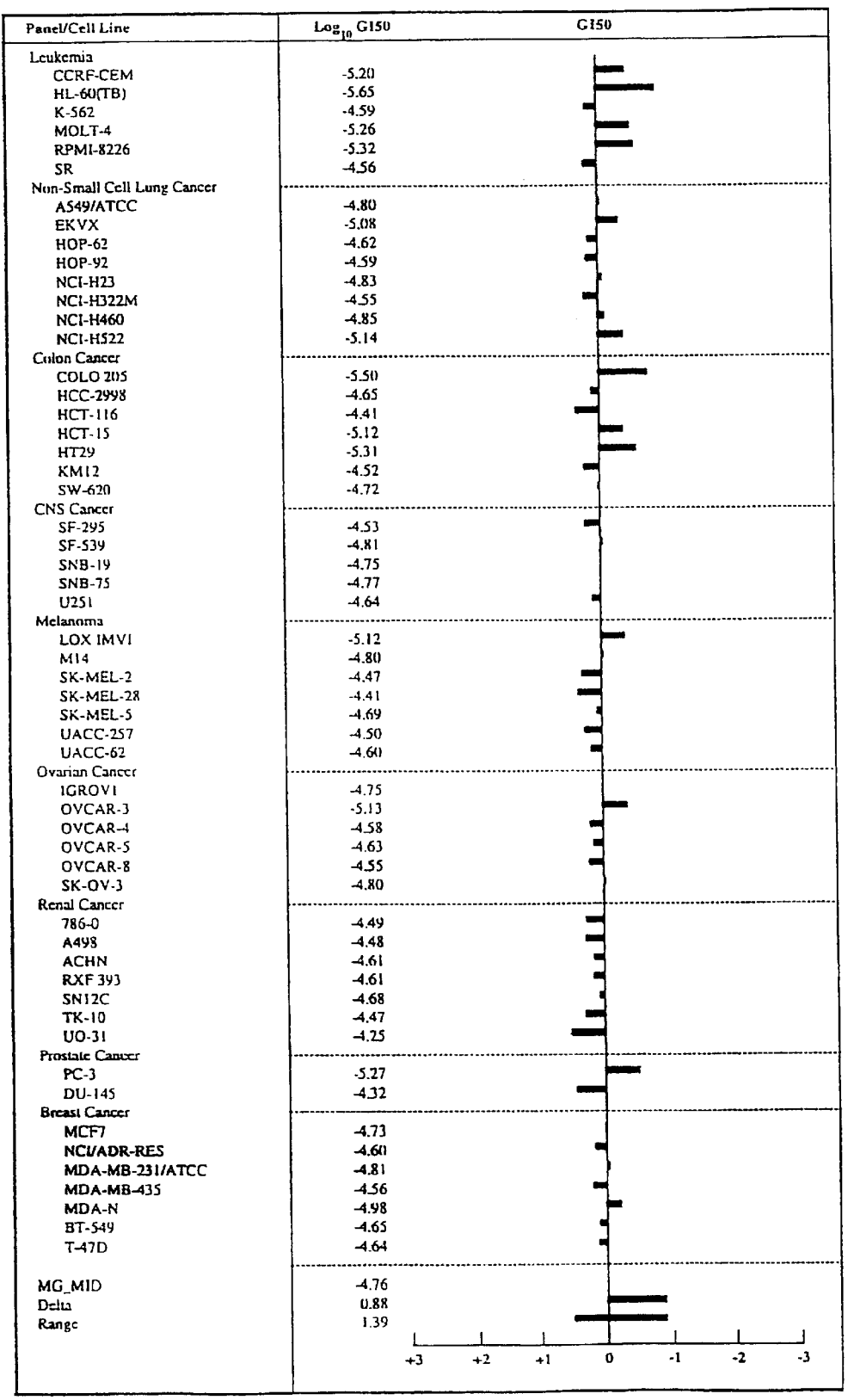
Figure 12B:
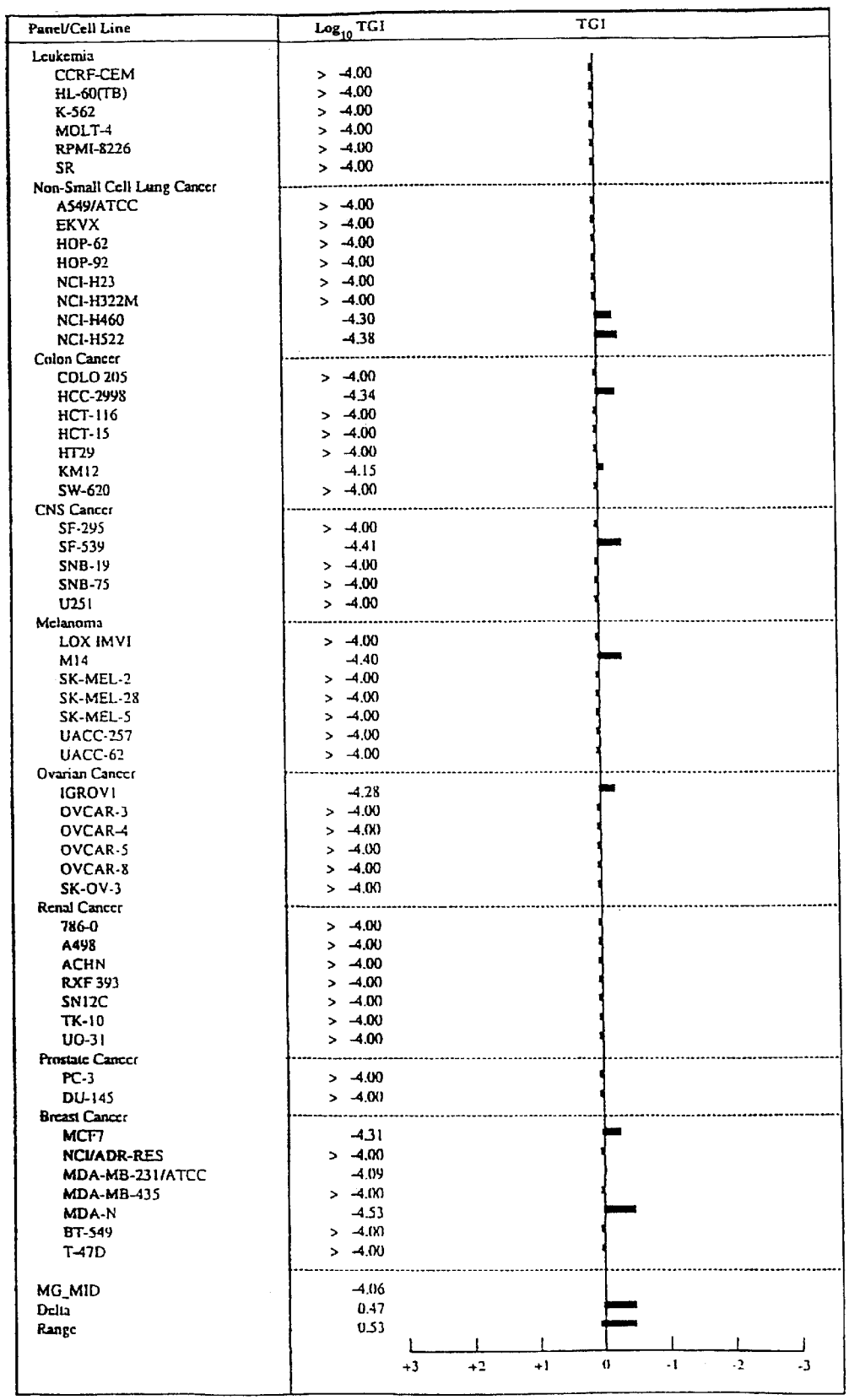

Compounds of the present invention have been subjected to the drug screening procedure employed by the National Cancer Institute for the screening of drugs having possible anticancer utility. The screening procedure uses a diverse, disease-oriented panel consisting of different human tumor cell lines organized into disease-specific subpanels. The compounds of the present invention were tested over a range of concentrations for cytotoxic or growth-inhibitory effects against cell lines comprising the panel. The subpanels represented diverse histologies (leukemias, melanomas, and tumors of the lung, colon, kidney, breast, ovary, and brain). The tests produced individual dose-responses, one for each cell line (i.e., one for each example), and the data are disclosed in dose-response curves, e.g., FIGS. 1(A)–1(I). The data provided by these dose response curves are summarized using a mean-graph format, e.g., FIG. 2.

To produce data for the mean-graph format, a compound concentration that produced a target level response was calculated for each cell line. Three different response parameters were evaluated. The first response parameter was the growth inhibition ("$GI_{50}$"). $GI_{50}$ is the concentration of compounds made according to the present invention that produced an apparent 50% decrease in the number of tumor cells relative to the appropriate control (not exposed to the compounds of the present invention) at the end of the incubation period.

The second response parameter was the total growth inhibition ("TGI"). TGI is the concentration at which the number of tumor cells remaining at the end of the incubation period substantially equal the number of tumor cells existing at the start of the incubation period.

The third response parameter was the lethal concentration ("$LC_{50}$"). $LC_{50}$ is the concentration of compounds made according to the present invention that caused an apparent 50 percent reduction in the number of tumor cells relative to the appropriate control (not exposed to the compounds of the present invention) at the start of the incubation period.

In a typical $GI_{50}$ mean graph the relative position of the vertical reference line along the horizontal concentration axis was obtained by averaging the negative $log_{10}GI_{50}$ values for all the cell lines tested against the compound. Horizontal bars were then plotted for the individual negative $log_{50}GI_{50}$ values of each cell line relative to the vertical reference line. The $GI_{50}$ graph thus provides a characteristic fingerprint for the compound, displaying the individual cell lines that are proportionately more sensitive than average (bars extending to the right of the reference line) or proportionately less sensitive than average (bars extending to the left of the reference line). The length of a bar is proportional to the difference between the $log_{10}GI_{50}$ value obtained with the particular cell line and the mean (represented by the vertical reference line).

The data obtained using the cell line procedures referred to above are provided by FIGS. 1–12. This data shows that the compounds of the present invention inhibit the growth of living cells.

What is claimed is:

1. A method for treating a mammalian subject having leukemia, lung cancer, colon cancer, central nervous system cancer, melanoma, ovarian cancer, renal cancer, prostate cancer and/or breast cancer, comprising:

providing at least one compound selected from the group consisting of compounds having Formula 2

Formula 2

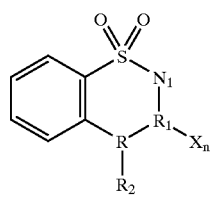

where R and $R_1$ are carbon or nitrogen, and with $R_1$=carbon $R_1$ is bonded to $N_1$ by a double bond, R is nitrogen, X is hydrogen or halogen, and $R_2$ is selected from the group consisting of alkyl and aryl amino, the compound having an $IC_{50}$ for CDK4 of less than about 10 μM, and having an $IC_{50}$ for CDC2 of more than about 60 μM and having an $IC_{50}$ for CDK2/A of more than about 100 μM, and having an $IC_{50}$ for CDK2/E of more than about 80 μM; and administering an effective amount of the compound to the mammalian subject having the cancer.

2. A method for inhibiting the growth of living cancer cells in a mammalian subject having leukemia, lung cancer, colon cancer, central nervous system cancer, melanoma, ovarian cancer, renal cancer, prostate cancer and/or breast cancer, comprising:

providing at least one compound selected from the group consisting of compounds having Formula 2

Formula 2

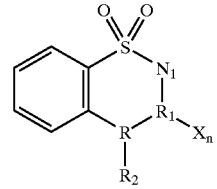

where R and $R_1$ are carbon or nitrogen, and with $R_1$=carbon $R_1$ is bonded to $N_1$ by a double bond and R is nitrogen, X is hydrogen or halogen, and $R_2$ is selected from the group consisting of alkyl and aryl amino, the compound having an $IC_{50}$ ratio for CDC2:CDK4 of more than 8.5, and having an $IC_{50}$ ratio for CDK2/A:CDK4 of more than about 14, and having an $IC_{50}$ ratio for CDC2/E:CDK4 of more than about 11.5; and contacting the living cancer cells of the mammalian subject in vivo, ex vivo or both with an amount of the compound effective to inhibit the growth of the cells.

3. The method according to claim 2 where providing a compound comprises providing a composition comprising the compound and additives selected from the group consisting of carriers, diluents, excipients, diagnostics, direct compression buffers, buffers, stabilizers, fillers, disintegrates, flavors, colors, and mixtures thereof.

4. The method according to claim 2 where, with respect to Formula 2, R is nitrogen.

5. The method according to claim 4 where $R_2$ is alkyl.

6. The method according to claim 4 where $R_2$ is selected from the group consisting of methyl and ethyl.

7. The method according to claim 4 where X is halogen.

8. The method according to claim 4 where X is chlorine.

9. The method according to claim 2 where the compound is

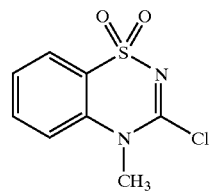

10. The method according to claim 2 where the compound is

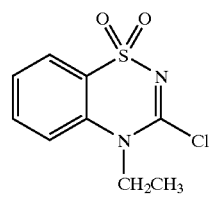

11. A method for treating a mammalian subject having leukemia, lung cancer, colon cancer, central nervous system cancer, melanoma, ovarian cancer, renal cancer, prostate cancer and/or breast cancer, comprising:

providing a compound having a formula

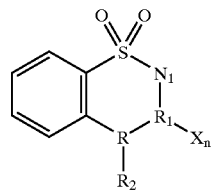

Formula 2 where R and $R_1$ are carbon or nitrogen, and with $R_1$=carbon $R_1$ is bonded to $N_1$ by a double bond and R is nitrogen, X is hydrogen or halogen, and $R_2$ is selected from the group consisting of alkyl and aryl amino; and contacting living cancer cells of the mammalian subject having the cancer in vivo, ex vivo or both with an effective amount of the compound.

12. A method for treating a mammalian subject having leukemia, lung cancer, colon cancer, central nervous system cancer, melanoma, ovarian cancer, renal cancer, prostate cancer and/or breast cancer, comprising:

providing a compound having a formula

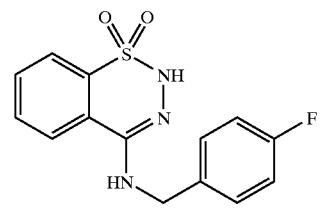

and contacting living cancer cells of the mammalian subject in vivo, ex vivo or both with an effective amount of the compound.

* * * * *